United States Patent [19]

Takiguchi et al.

[11] Patent Number: 5,595,685
[45] Date of Patent: Jan. 21, 1997

[54] MESOMORPHIC COMPOUND, LIQUID CRYSTAL COMPOSITION CONTAINING SAME, LIQUID CRYSTAL DEVICE USING SAME AND DISPLAY APPARATUS

[75] Inventors: Takao Takiguchi, Tokyo; Takashi Iwaki, Machida; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 460,790

[22] Filed: Jun. 2, 1995

Related U.S. Application Data

[63] Continuation of Ser. No. 65,690, May 25, 1993, abandoned, which is a continuation of Ser. No. 645,458, Jan. 24, 1991, abandoned.

[30] Foreign Application Priority Data

| Jan. 25, 1990 | [JP] | Japan | 2-016811 |
| Jun. 5, 1990 | [JP] | Japan | 2-147034 |
| Nov. 29, 1990 | [JP] | Japan | 2-332677 |

[51] Int. Cl.⁶ .................... C09K 19/34; C07D 285/12
[52] U.S. Cl. .................... 252/299.61; 548/146
[58] Field of Search ............ 252/299.61; 548/146

[56] References Cited

U.S. PATENT DOCUMENTS

| 4,282,364 | 8/1981 | Amato et al. | 548/202 |
| 4,367,924 | 1/1983 | Clark et al. | 359/53 X |
| 4,977,171 | 12/1990 | Suzuki et al. | 514/365 |
| 5,034,151 | 7/1991 | Shinjo et al. | 252/299.6 |
| 5,250,218 | 10/1993 | Mori et al. | 252/299.61 |
| 5,262,083 | 11/1993 | Mori et al. | 252/299.61 |
| 5,269,964 | 12/1993 | Yamashita et al. | 252/299.61 |

FOREIGN PATENT DOCUMENTS

| 8808019 | 4/1988 | Germany . |
| 56-107216 | 8/1981 | Japan . |
| 0008019 | 10/1988 | WIPO . |

OTHER PUBLICATIONS

Schadt et al. "Applied Physics Letters", vol. 18, No. 4, pp. 127–128 (1971).
Zaschke et al., "J. Prake. Chem." vol. 321, pp. 643–654 (1979).
"Organic Synthesis–Coll. vol. 6" p. 34 (1988).
Suzuki et al. "J. Org. Chem." vol. 38, No. 20 pp. 3571–3575 (1973).
"Organic Synthesis–Coll. vol. 3" pp. 28–31 (1986).
J. Practical Chemistry, vol. 321, No. 4 (1979) 643–54.

*Primary Examiner*—Cynthia Harris
*Attorney, Agent, or Firm*—Fitzpatrick, Cella, Harper & Scinto

[57] ABSTRACT

A mesomorphic compound represented by:

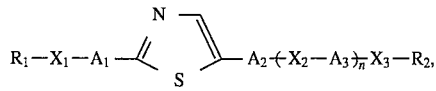

where $R_1$ and $R_2$ are alkyl; $X_1$ and $X_3$ are a single bond, $$-O-, -\underset{\underset{O}{\parallel}}{O}C-, -\underset{\underset{O}{\parallel}}{C}O-, -\underset{\underset{O}{\parallel}}{C}-;$$

$X_2$ is a single bond, $$-\underset{\underset{O}{\parallel}}{O}C- \text{ or } -\underset{\underset{O}{\parallel}}{C}O-;$$

$A_1$, $A_2$ and $A_3$ are a single bond, aryl, heteroaryl, pyrimidyl or cyclohexyl, $X_{4a}$, $X_{5a}$, $X_{4b}$, $X_{5b}$, $X_{4c}$ and $X_{5c}$ are H, F, Cl, Br, $-CH_3$, $-CN$ or $-CF_3$; and n is 0 or 1.

22 Claims, 4 Drawing Sheets

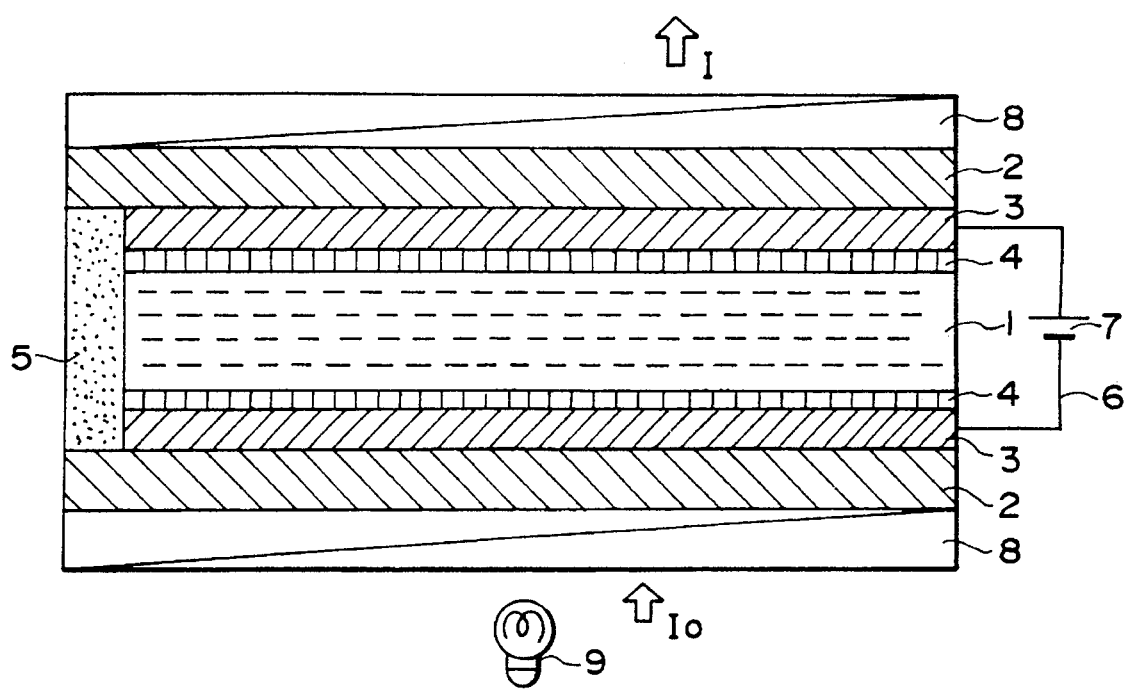
F I G. 1 the compound, a liquid crystal composition containing the compound, a liquid crystal device using the composition and a display apparatus, and more particularly to a novel liquid crystal composition with improved responsiveness to an electric field and a liquid crystal device using the liquid crystal composition for use in a liquid crystal display apparatus, a liquid crystal-optical shutter, etc.

MESOMORPHIC COMPOUND, LIQUID CRYSTAL COMPOSITION CONTAINING SAME, LIQUID CRYSTAL DEVICE USING SAME AND DISPLAY APPARATUS

This application is a continuation of application Ser. No. 08/065,690, filed May 25, 1993, now abandoned which is a continuation of application Ser. No. 07/645,458, filed Jan. 24, 1991, now abandoned.

FIELD OF THE INVENTION AND RELATED ART

The present invention relates to a novel mesomorphic compound, a liquid crystal composition containing the compound, a liquid crystal device using the composition and a display apparatus, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed and a smaller temperature-dependence of the response speed, and a display apparatus.

According to the present invention, there is provided a mesomorphic compound represented by the following formula (I):

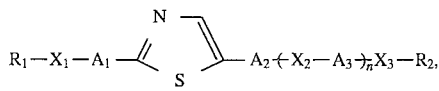

[I]

wherein $R_1$ and $R_2$ respectively denote an alkyl group having 2–16 carbon atoms capable of having a substituent; $X_1$ and $X_3$ respectively denote a single bond,

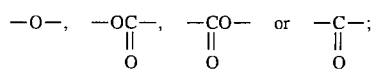

$X_2$ denotes a single bond,

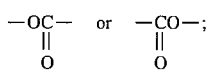

$A_1$ and $A_2$ respectively denote a single bond,

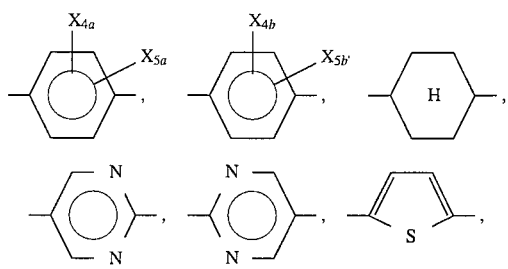

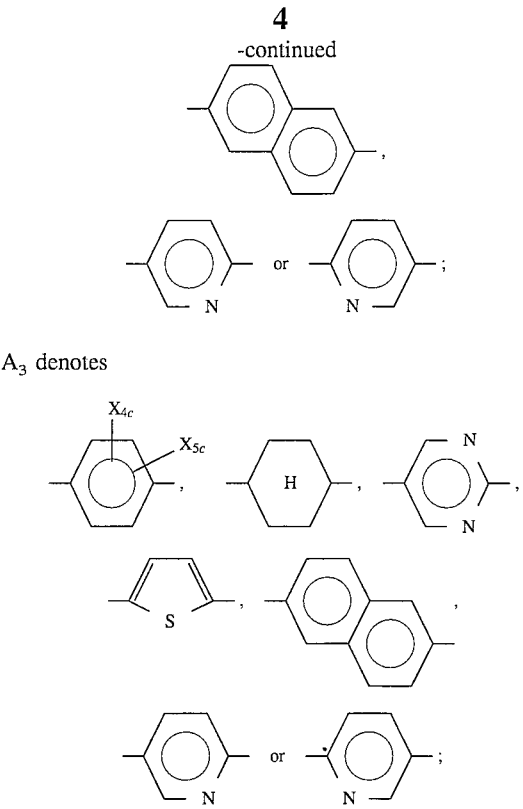

$A_3$ denotes $X_{4a}$, $X_{5a}$, $X_{4b}$, $X_{5b}$, $X_{4c}$ and $X_{5c}$ respectively denote hydrogen, fluorine, chlorine, bromine, —$CH_3$, —$CN$ or —$CF_3$; and n is 0 or 1, with proviso that: $X_1$ always denotes a single bond when $A_1$ denotes a single bond, $X_3$ always denotes a single bond when $A_2$ denotes a single bond and n is 0; $A_1$ and $A_2$ cannot be single bonds simultaneously; $X_3$ cannot be —O— when $X_1$ denotes a single bond or —O—, $A_1$ denotes a single bond or

and —$A_2$—($X_2$—$A_3$)$_n$— denotes

and $X_1$ cannot be a single bond when $A_1$ denotes and $A_2$ denotes a single bond and n is 0.

According to the present invention, there is further provided a chiral smectic liquid crystal composition containing at least one species of the mesomorphic compound as described above.

The present invention further provides a liquid crystal device comprising a pair of substrates and such a liquid crystal composition as described above disposed between the electrode plates, and a display apparatus comprising the liquid crystal device.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic sectional view of a liquid crystal display device using a liquid crystal composition assuming a chiral smectic phase;

DETAILED DESCRIPTION OF THE INVENTION

Figure 2:
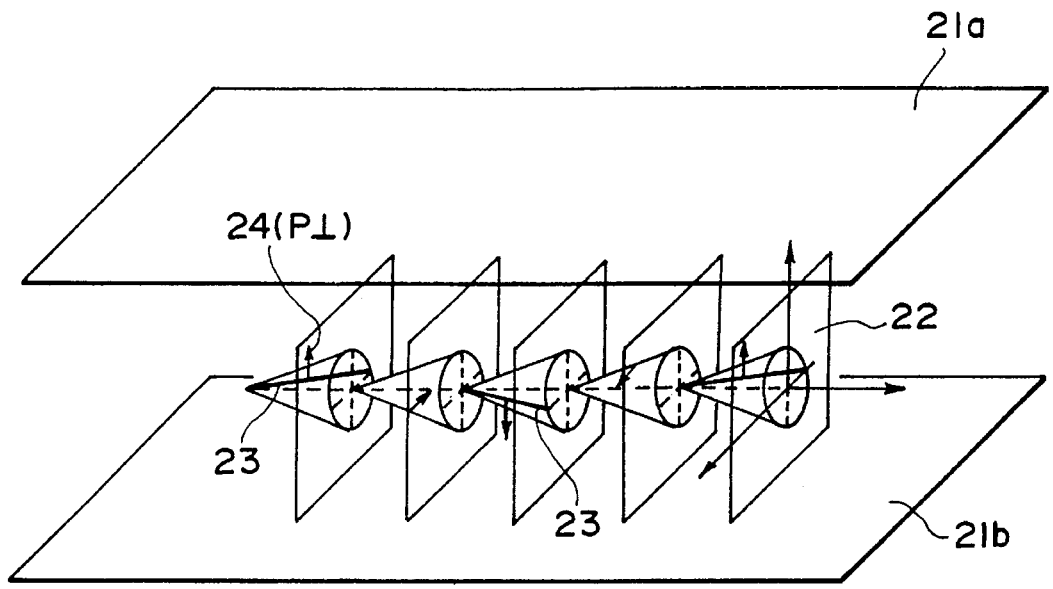
FIGS. 2 and 3 are schematic perspective views of a device cell embodiment for illustrating the operation principle of a liquid crystal device utilizing ferroelectricity of a liquid crystal composition.

Preferred examples of the mesomorphic compound of the formula (I) may include those represented by the following formulas [Ia]–[Iq]:

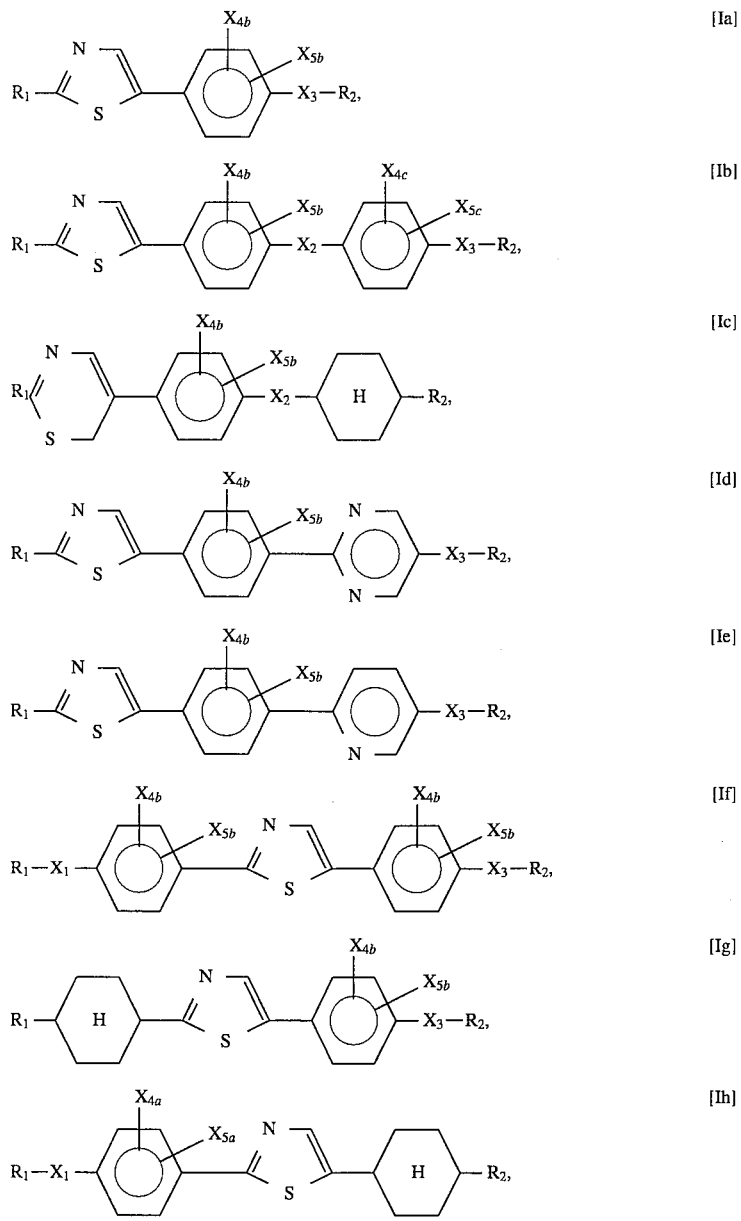

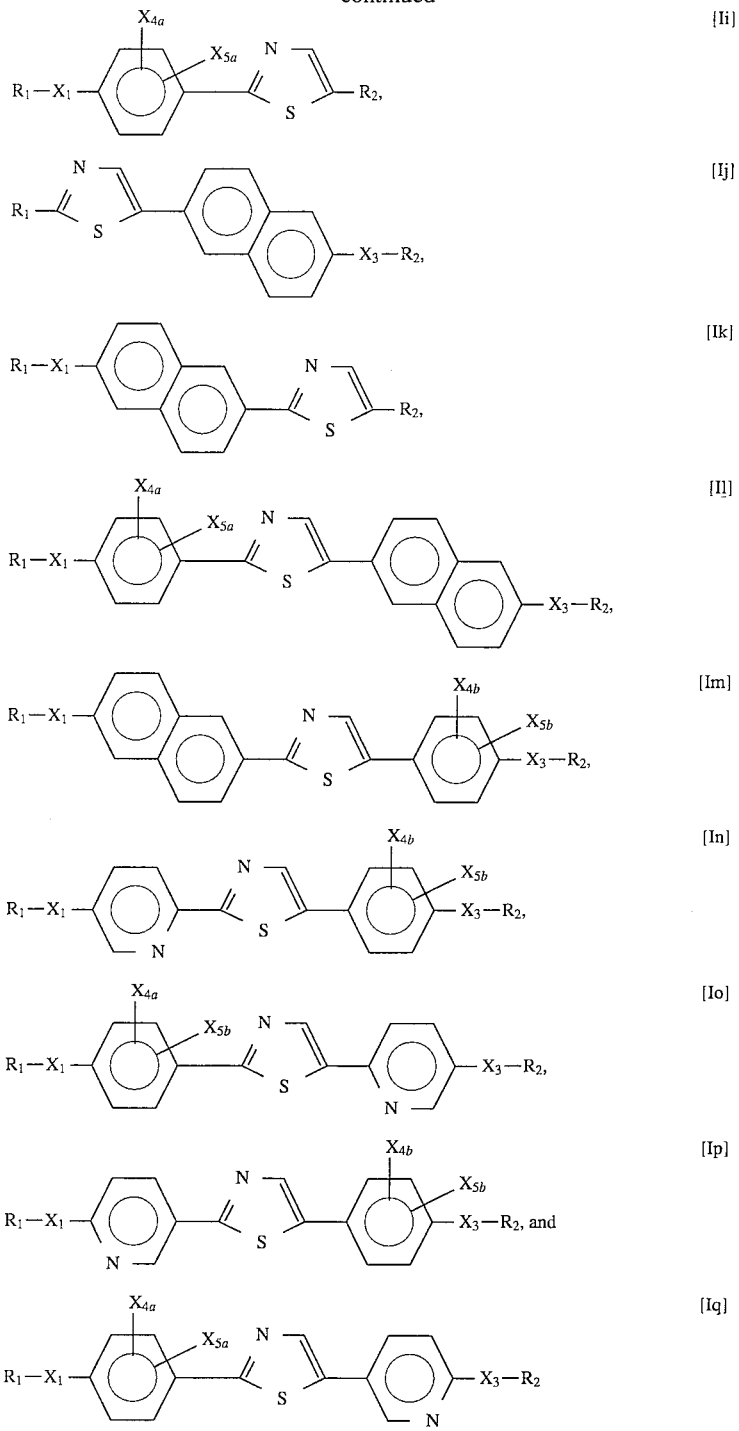

with proviso that $X_3$ cannot be —O— when $X_{4b}$ and $X_{5b}$ are both hydrogen in the formula [Ia]; and when $X_{4a}$, $X_{5a}$, $X_{4b}$ and $X_{5b}$ and all hydrogen in the formula [If]; and $X_1$ cannot be a single bond when $X_{4a}$ and $X_{5a}$ are both hydrogen in the formula [Ii]. In the above, $R_1$, $R_2$, $X_1$, $X_2$, $X_3$, $X_{4a}$, $X_{5a}$, $X_{4b}$, $X_{5b}$, $X_{4c}$ and $X_{5c}$ respectively denote the same as defined above.

Further, preferred examples of the mesomorphic compound of the formula (I) may include those represented by the following formulas [Iaa]–[Ina]:

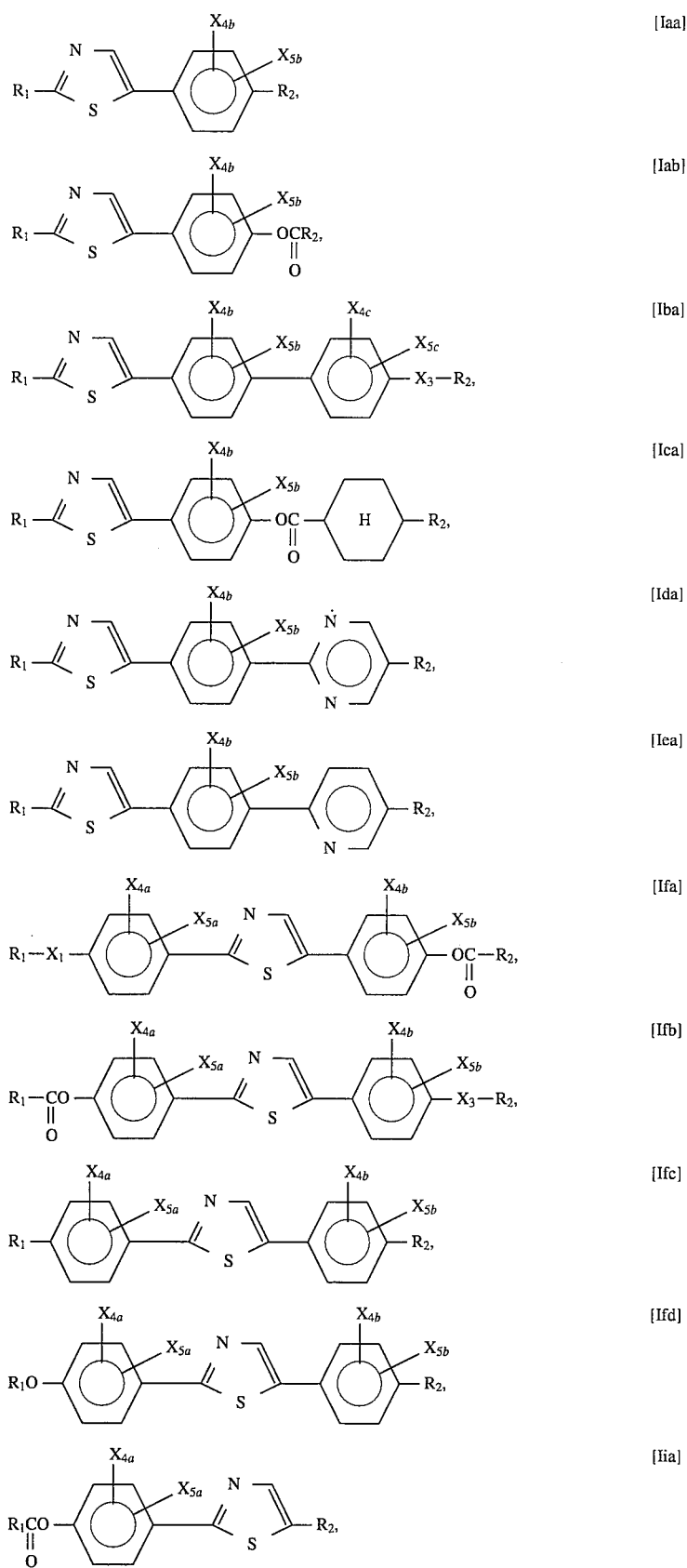

-continued

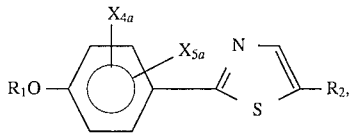
[Iib]

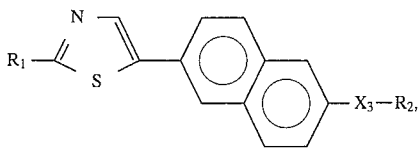
[Ija]

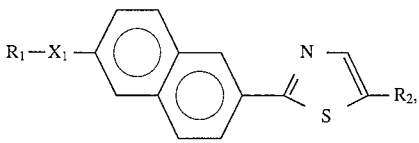
[Ika]

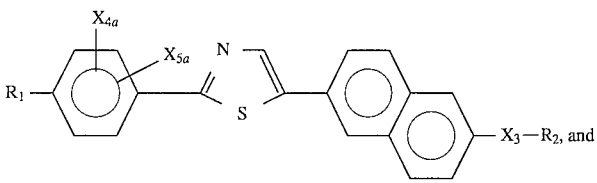
[Iia]

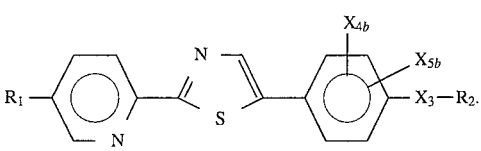
[Ina]

In the above, $R_1$, $R_2$, $X_1$, $X_3$, $X_{4a}$, $X_{5a}$, $X_{4b}$, $X_{5b}$, $X_{4c}$ and $X_{5c}$ respectively denote the same as defined above.

Preferred examples of $R_1$ and $R_2$ in the formula (I) may respectively include the following groups (i)–(iv):

(i) an n-alkyl group having 2–16 carbon atoms, particularly having 4–14 carbon atoms;

(ii)

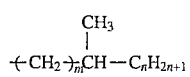

wherein m is an integer of 0–6 and n is an integer of 2–8 (optically active or inactive);

(iii)

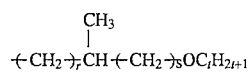

wherein r is an integer of 0–6, s is 0 or 1 and t is an integer of 1–12 (optically active or inactive); and (iv)

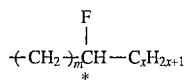

wherein m is 0 or 1 and x is an integer of 1–14. Here, * denotes an optically active center.

Heretofore, liquid crystals containing or capable of containing thiazole rings have been disclosed in H. Zaschke et al , "J. Prake. Chem.", 321, 643–654 (1979) and WO 88/08019. However, the former does not disclose a mesomorphic compound comprising a thiazole-2,5-diyl derivative as is represented by the formula (I) according to the present invention. In the latter, there is no disclose of even a specific embodiment of the thiazole-2,5-diyl derivative.

We have found that the thiazole-2,5-diyl derivative of the formula (I) has a lower viscosity than that of a 1,3,4-thiadiazole-2,5-diyl derivative disclosed in WO 88/08019 as is understood from Example 13 and Comparative Example 1 appearing hereinafter, so that the thiazole-2,5-diyl derivative of the formula (I) can provide a ferroelectric chiral smectic liquid crystal composition having high speed responsiveness. We have also found that such a liquid crystal composition improves an operation characteristic at a lower temperature and decreases temperature dependence of response speed. As a result, a liquid crystal device comprising such a liquid crystal composition and a display apparatus using the liquid crystal device showed good display characteristics.

The compounds represented by the general formula (I) may be synthesized through the following reaction schemes A and B.

Reaction Scheme A

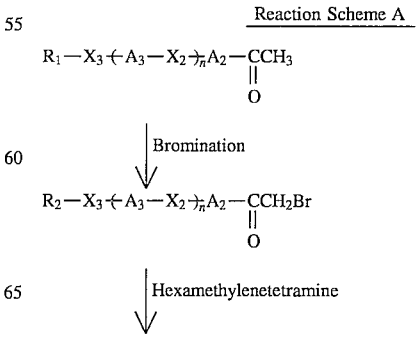

-continued
Reaction Scheme A

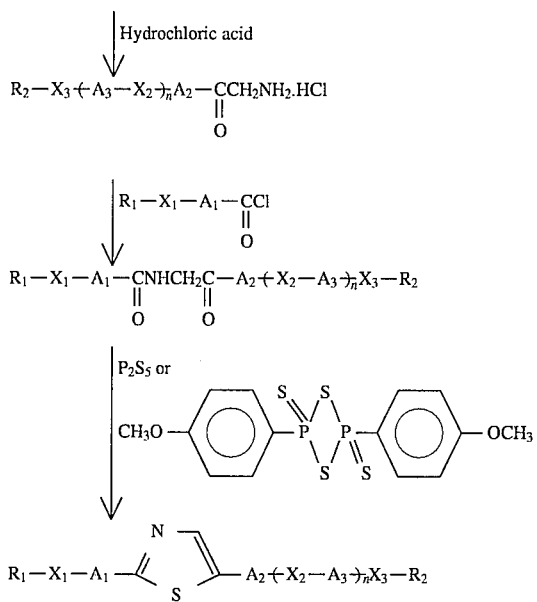

Reaction Scheme B

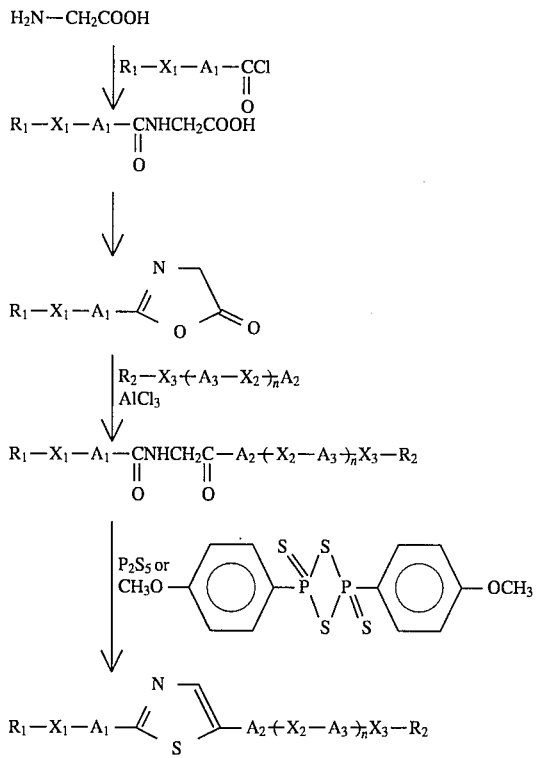

In a case where $X_1$ and $X_3$ are respectively $-O-$, $-OC(=O)-$ or $-CO(=O)-$ or $X_2$ is $-OC(=O)-$ or $-CO(=O)-$, it is also possible to form a group of $R_1-X_1-A_1-$ or $R_2-X_3-(A_3-X_2)_nA_2-$ through the following steps (a) to (c):

(a) Hydroxyl group or carboxyl group combined with $A_1$ or $A_2$ is modified with addition of a protective group into a non-reactive or less reactive group such as

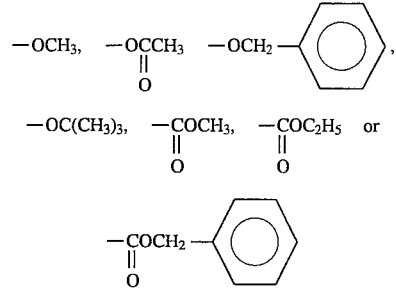

capable of elimination reaction.

(b) Ring closure is effected to form a thiazole ring.

(c) The protective group is eliminated and then the $R_1-X_1-A_1-$ or $R_2-X_3-(A_3-X_2)_nA_2-$ structure is formed. Specific examples of the mesomorphic compounds represented by the above-mentioned general formula (I) may include those shown by the following structural formulas.

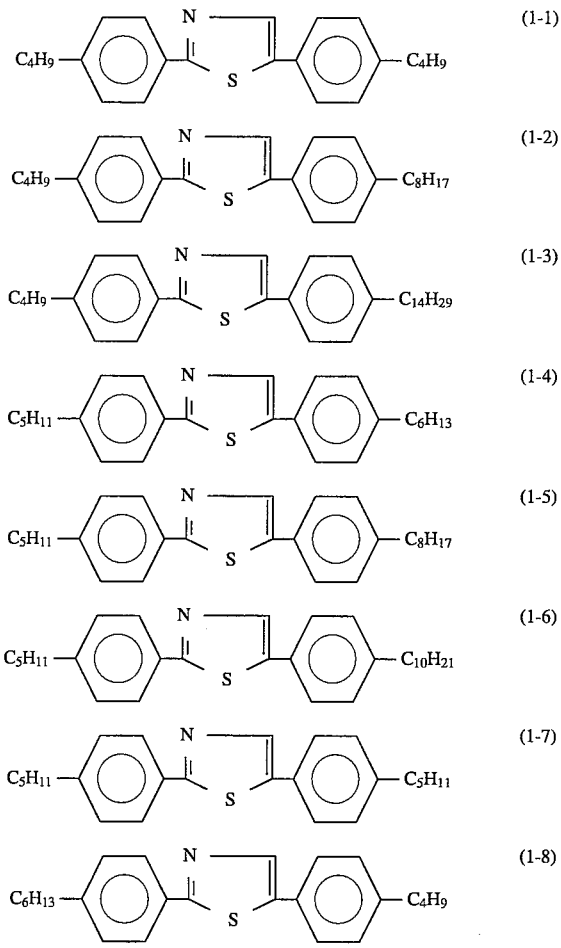

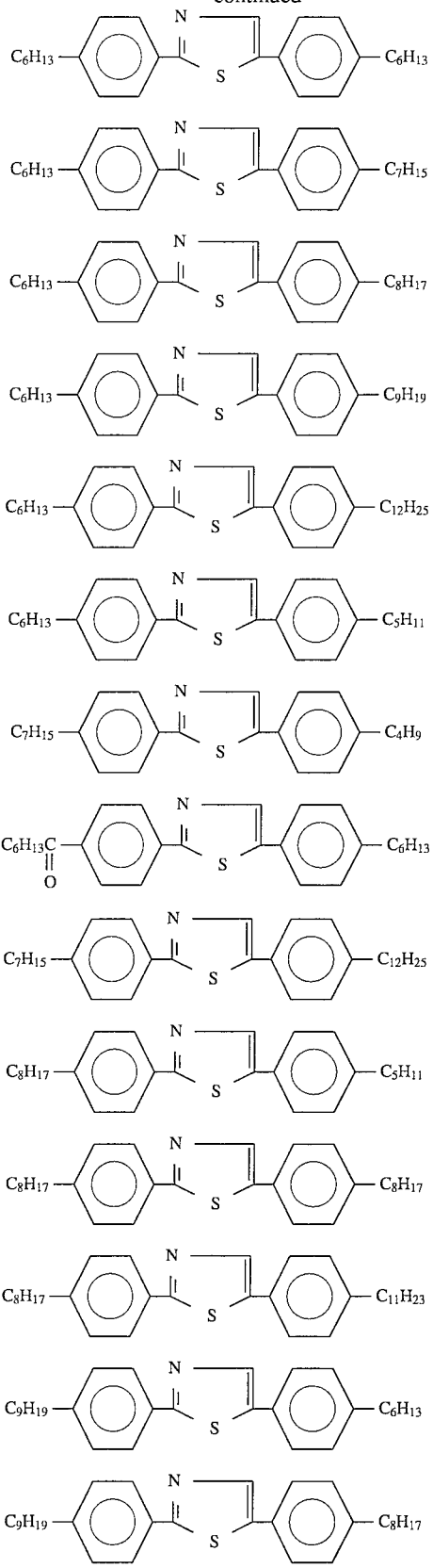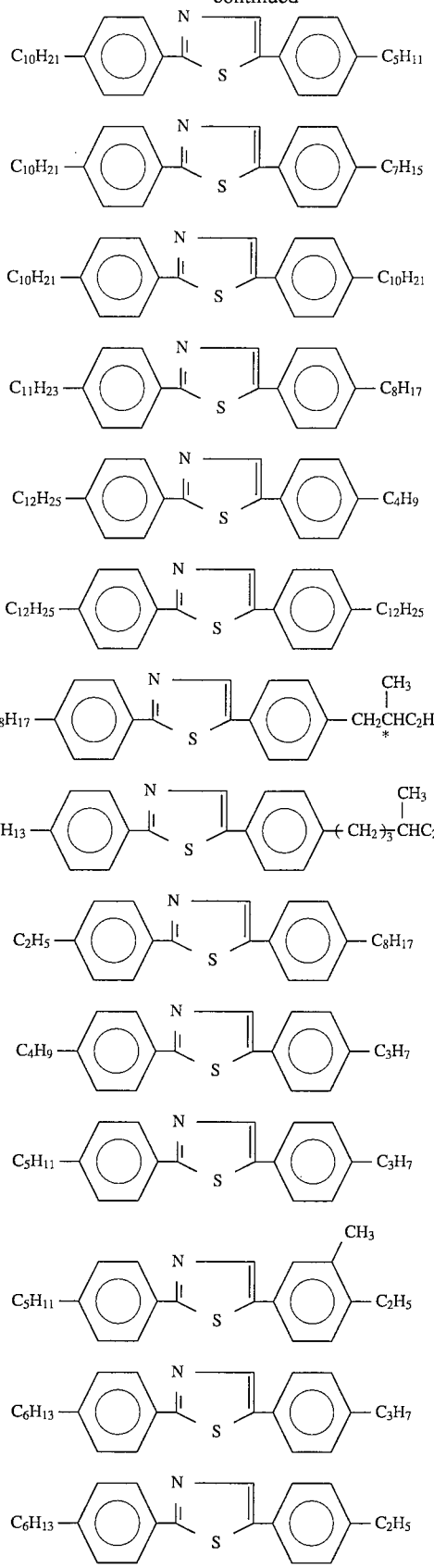

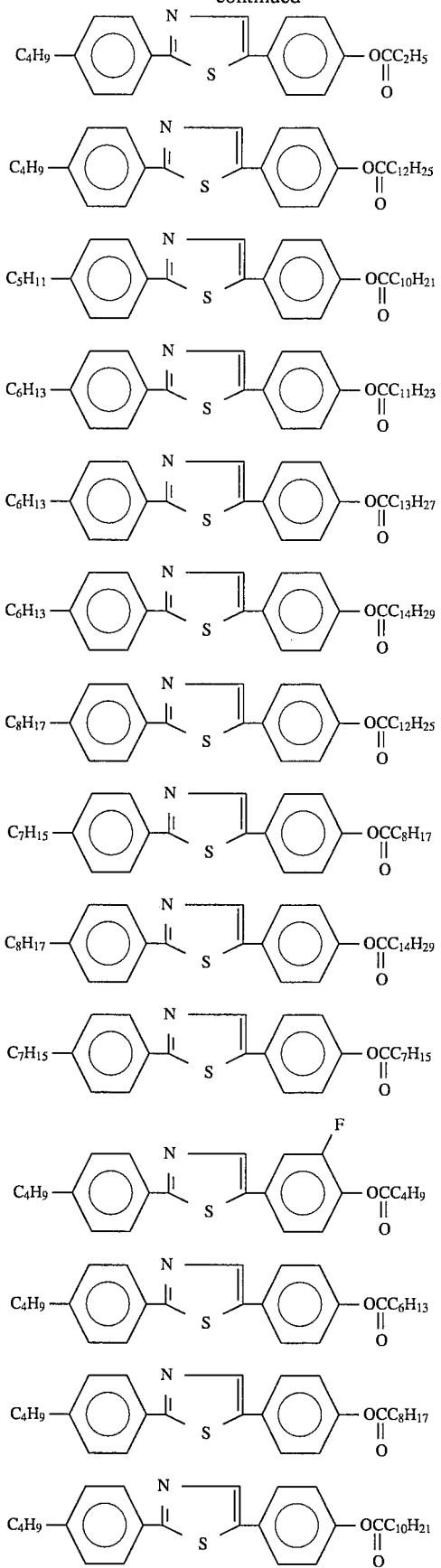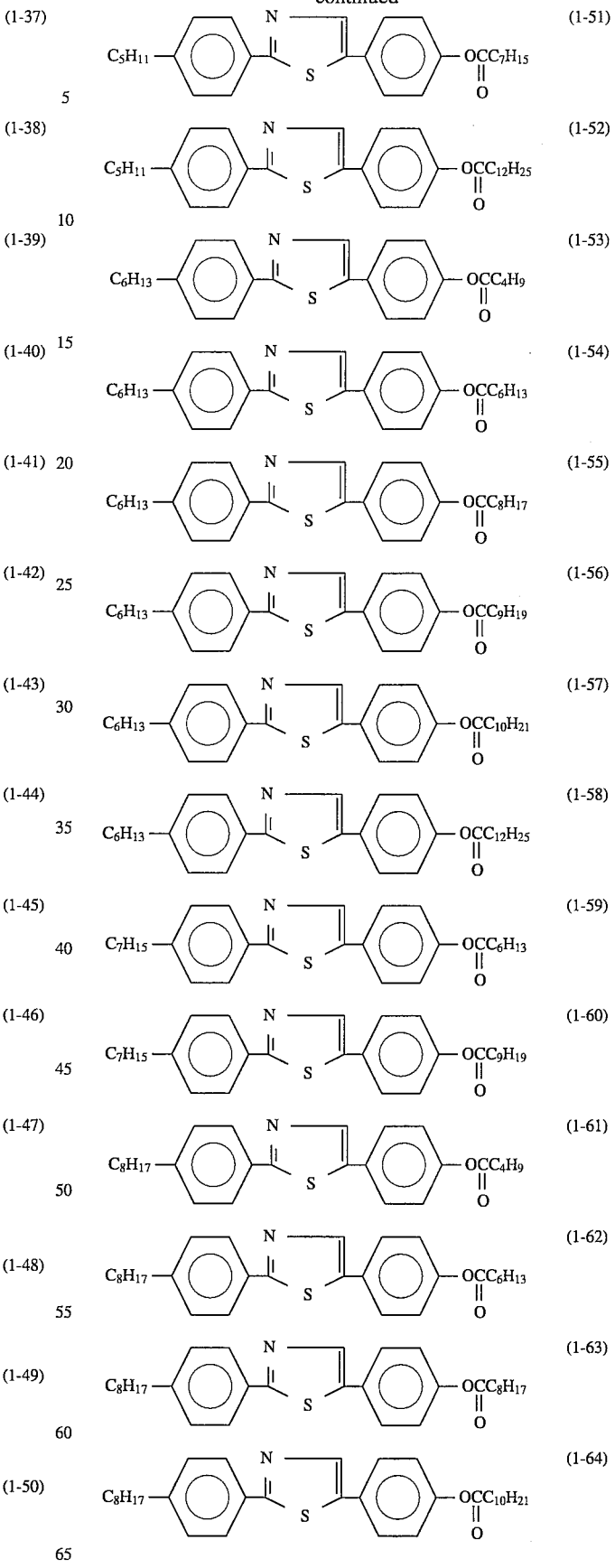

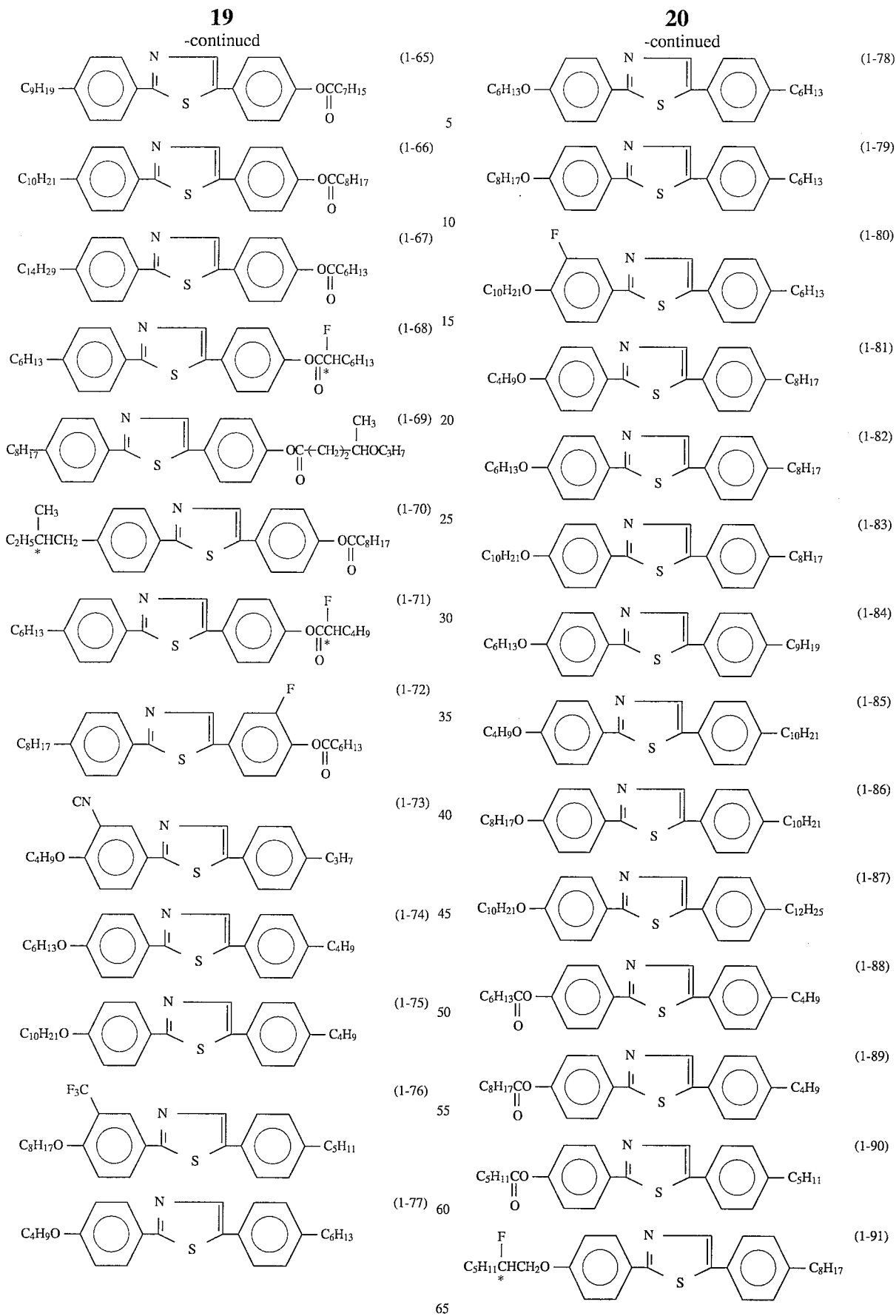

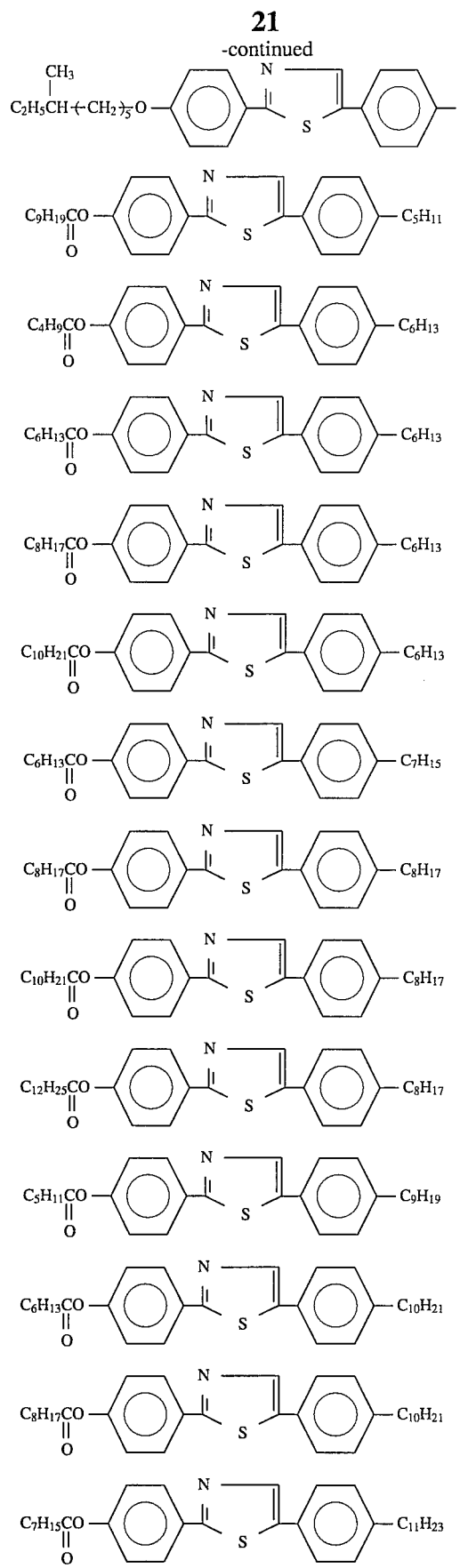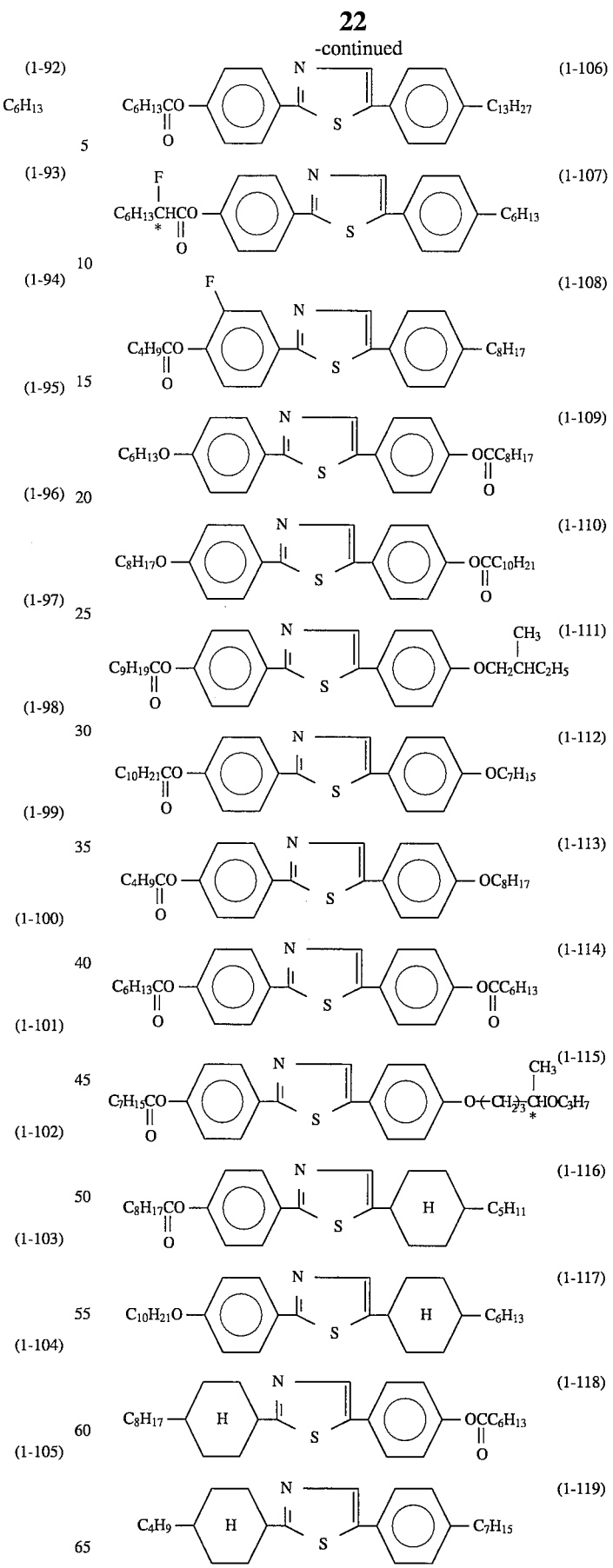

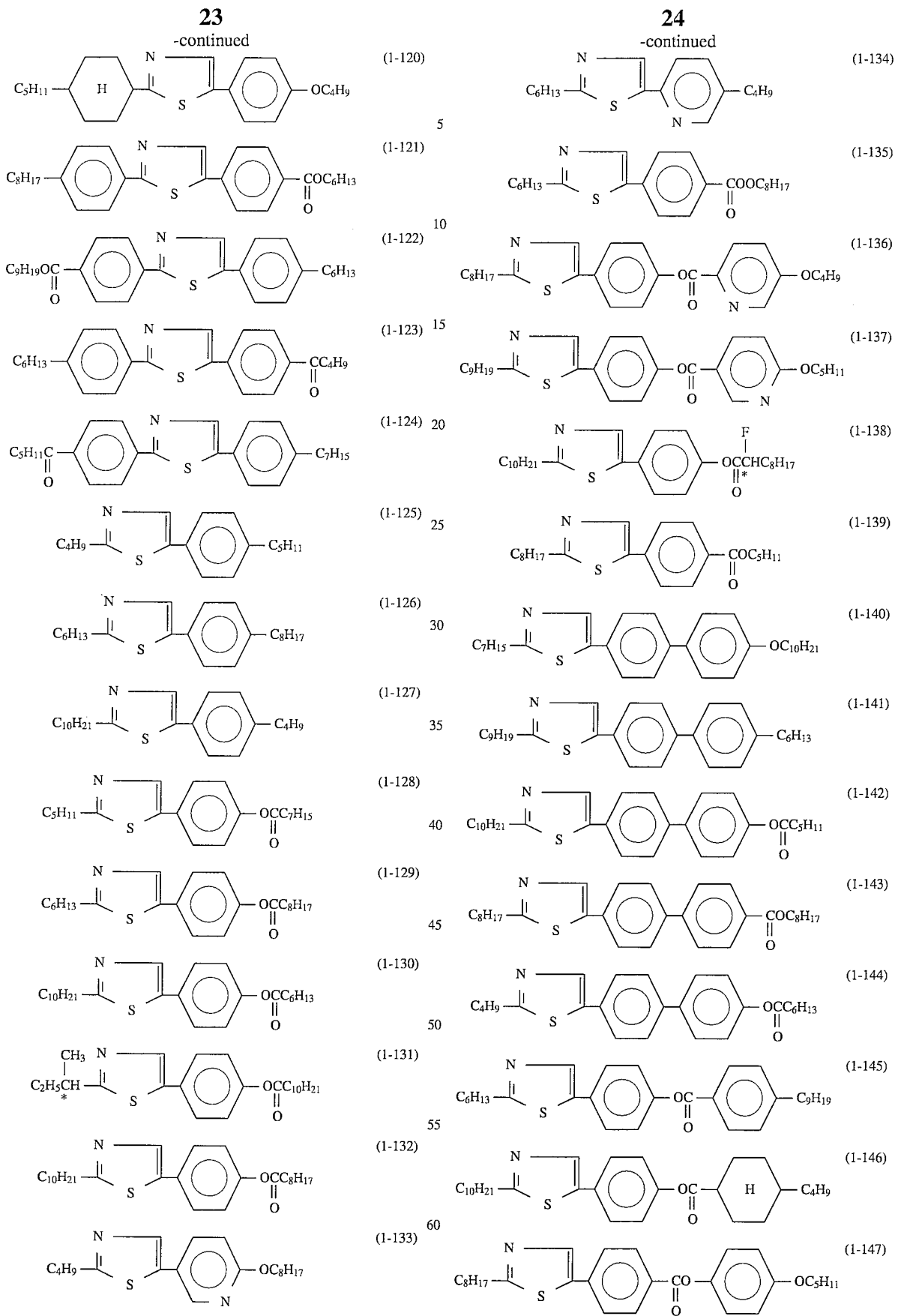

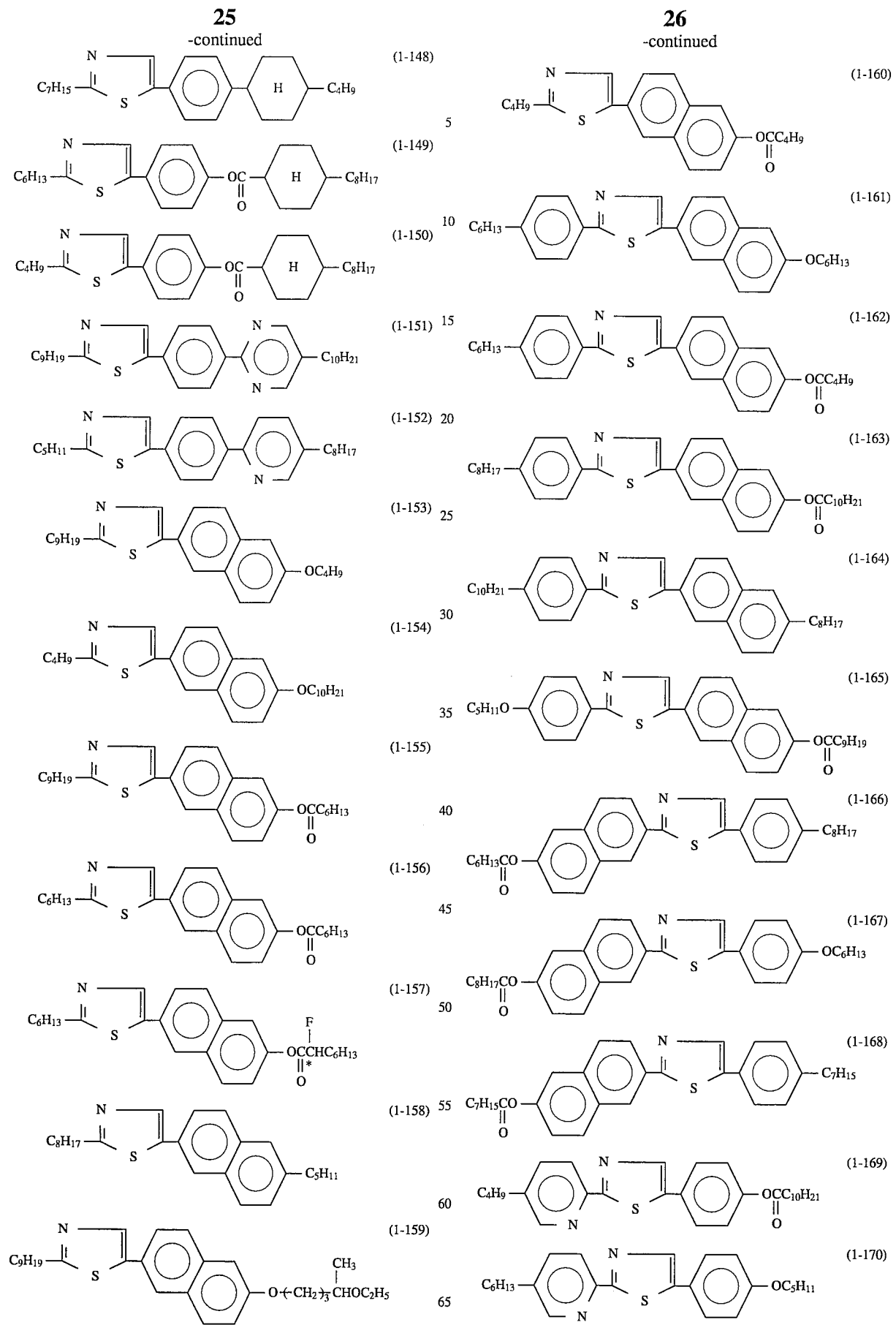

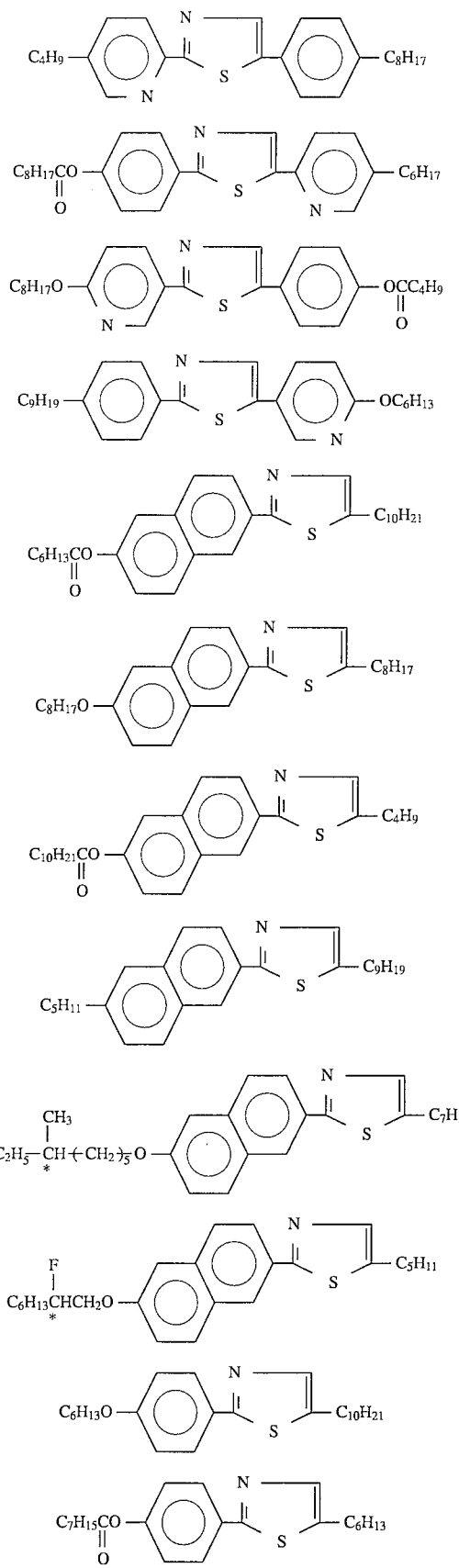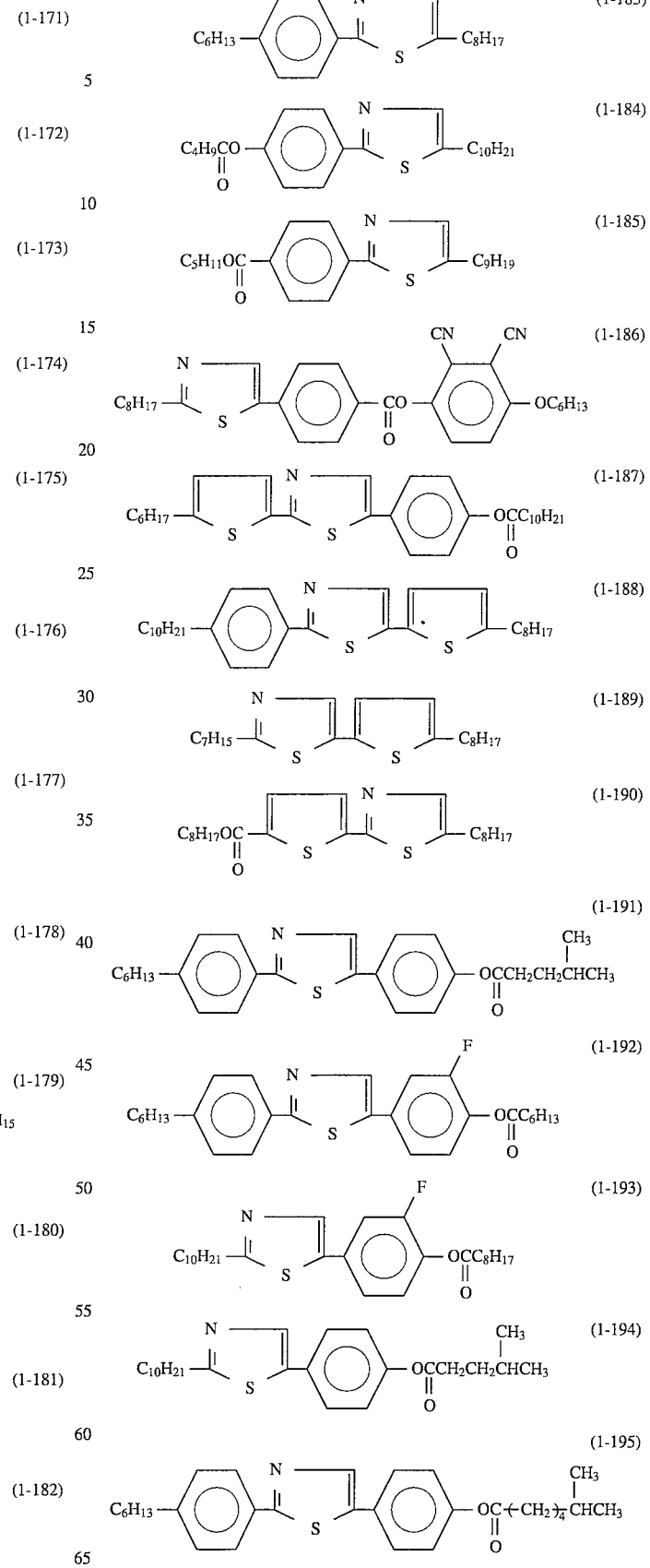

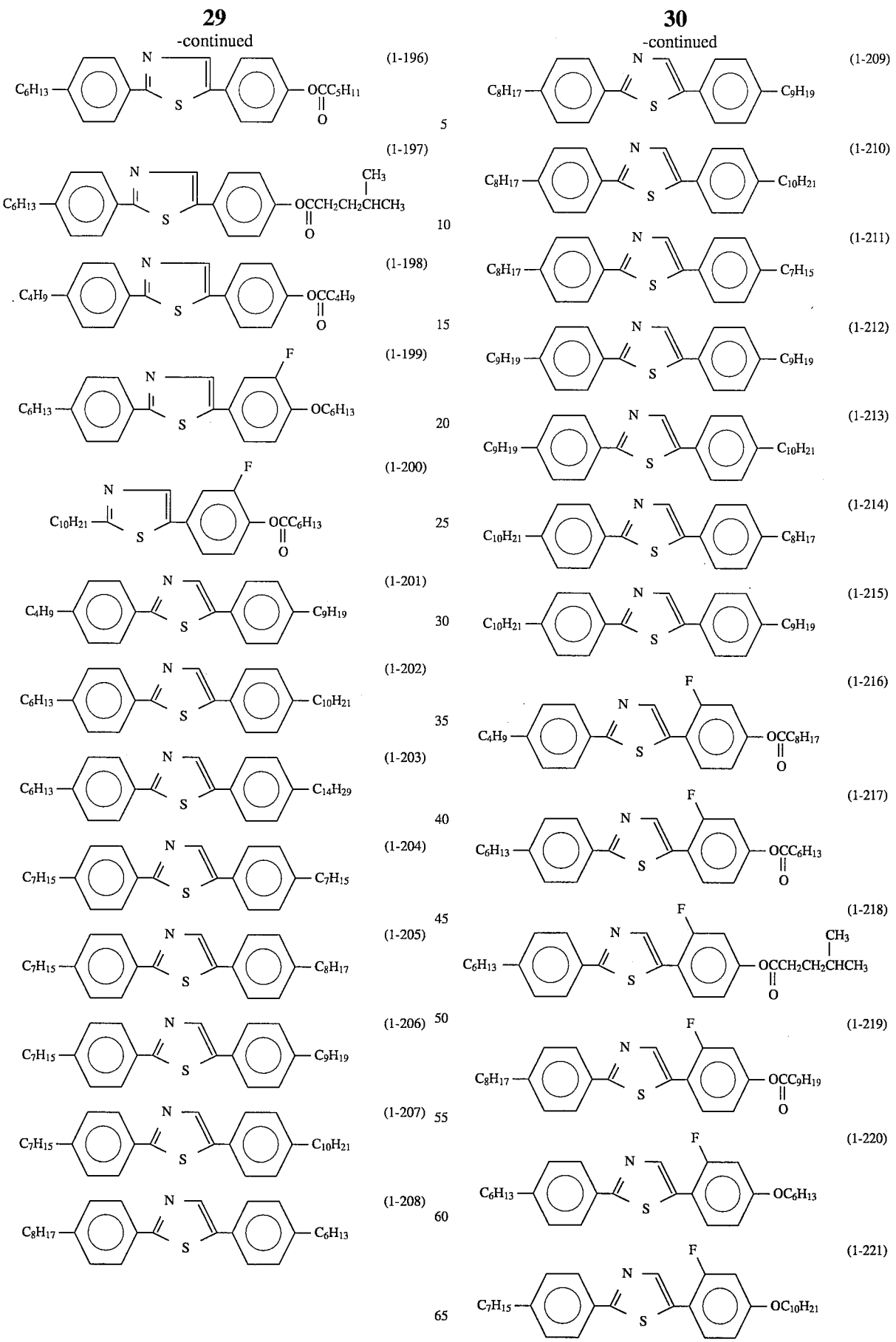

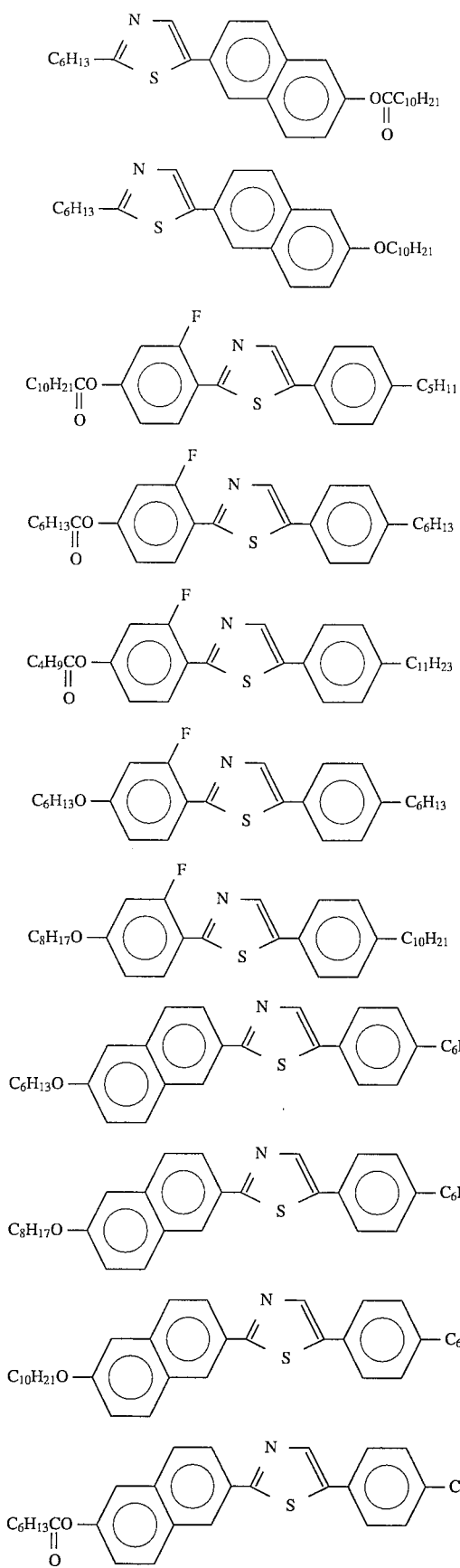
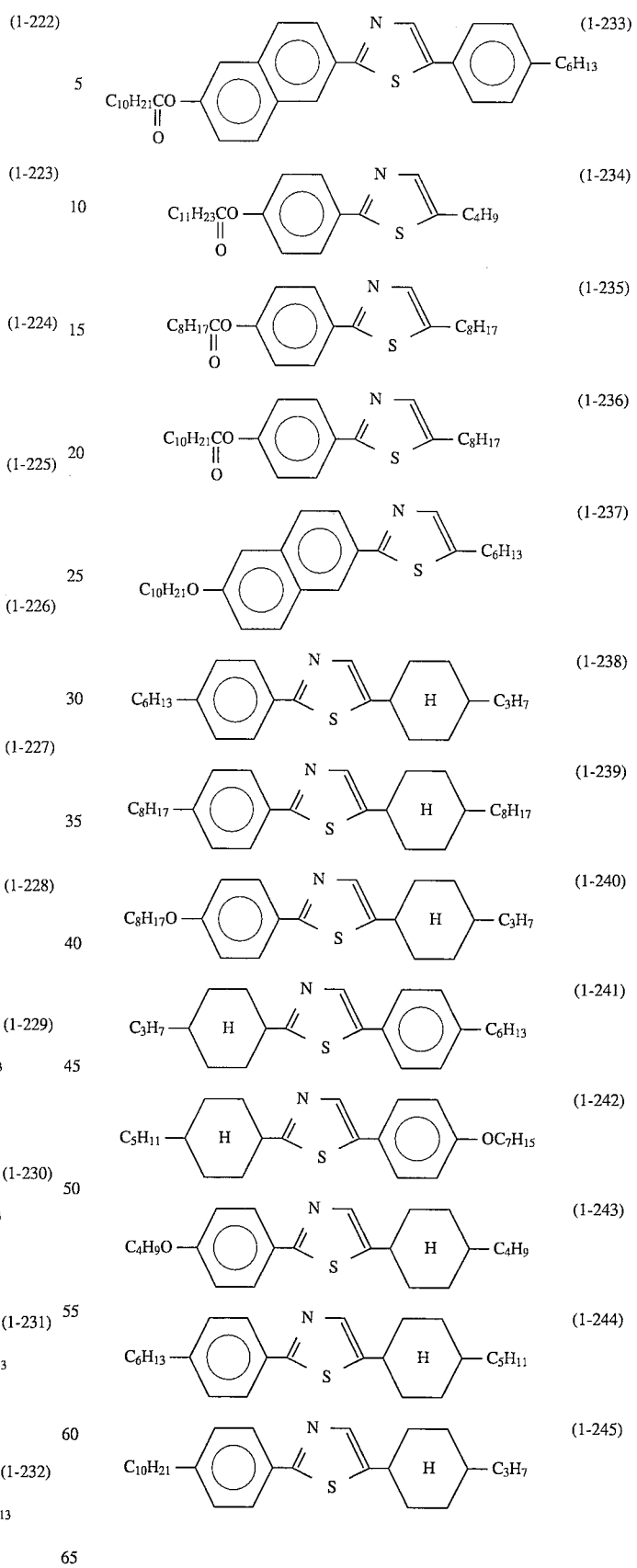

-continued

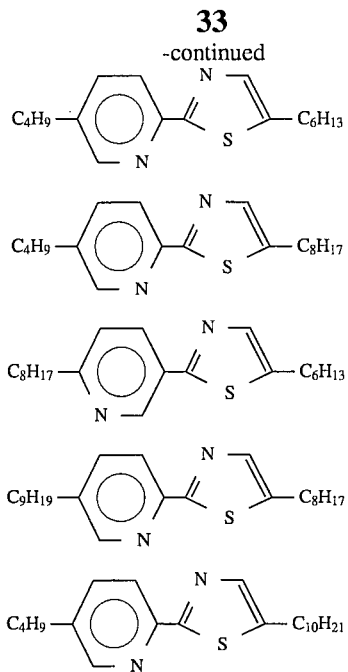

(1-246)
(1-247)
(1-248)
(1-249)
(1-250)

-continued

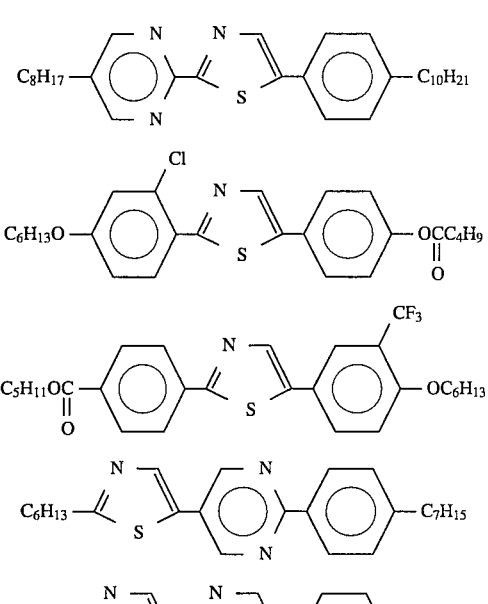

(1-251)
(1-252)
(1-253)
(1-254)
(1-255)
(1-256)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XI).

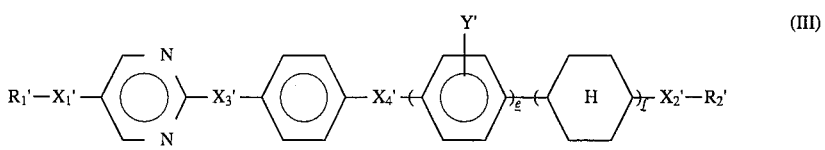

wherein $\underline{e}$ denotes 0 or 1 and $\underline{f}$ denotes 0 or 1 with proviso that $\underline{e}+\underline{f}=0$ or 1; Y' denotes H, halogen, $CH_3$ or $CF_3$; $X_1'$ and $X_2'$ respectively denote a single bond,

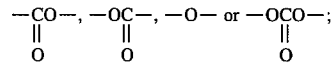

and $X_3'$ and $X_4'$ respectively denote a single bond,

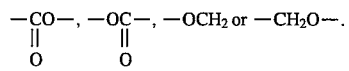

In the formula (III), preferred compounds thereof may include those represented by the following formulas (IIIa) to (IIId):

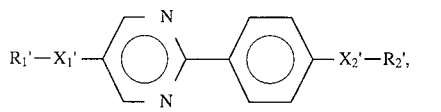
(IIIa)

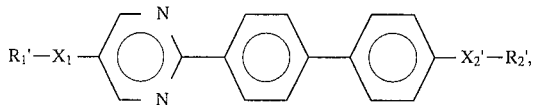
(IIIb)

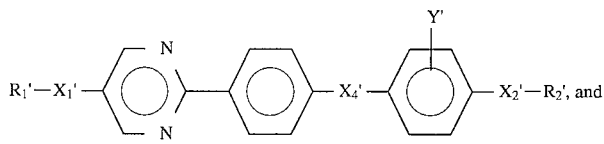
(IIIc)

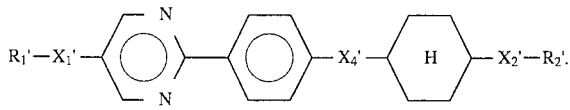
(IIId)

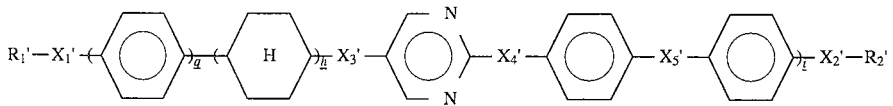
(IV)

wherein g and h respectively denote 0 or 1 with proviso that g+h=1; i denotes 0 or 1; $X_1'$ and $X_2'$ respectively denote a single bond,

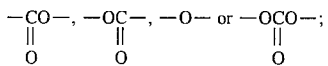

and $X_3'$, $X_4'$ and $X_5'$ respectively denote a single bond,

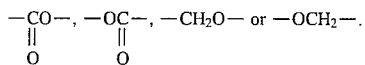

In the formula (IV), preferred compounds thereof may include those represented by the following formulas (IVa) to (IVc):

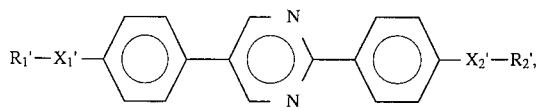
(IVa)

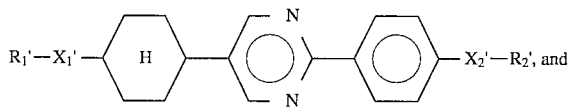
(IVb)

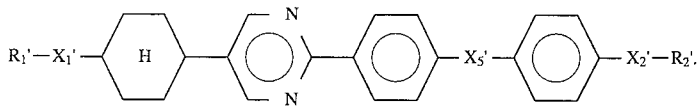
(IVc)

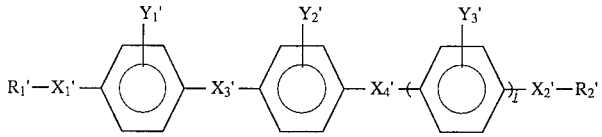
(V)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond,

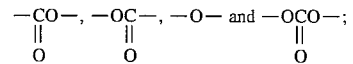

and $X_3'$ and $X_4'$ respectively denote a single bond,

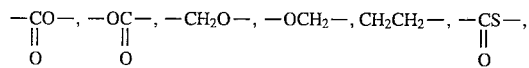

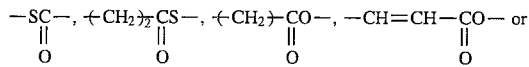

In the formula (V), preferred compounds thereof may include those represented by the following formulas (Va) and (Vb):

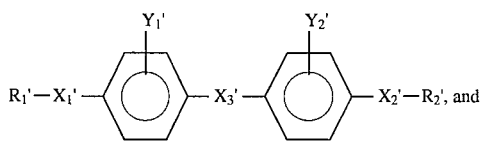 (Va)

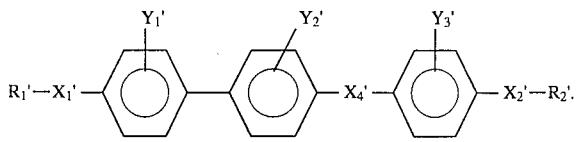 (Vb)

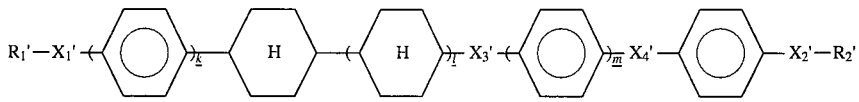 (VI)

wherein k, l and m respectively denote 0 or 1 with proviso that k+l+m=0, 1 or 2; $X_1'$ and $X_2'$ respectively denote a single bond,

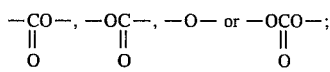

and $X_3'$ and $X_4'$ respectively denote a single bond,

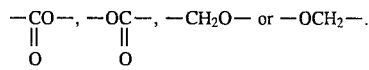

In the formula (VI), preferred compounds thereof may include those represented by the following formulas (VIa) to (VIf):

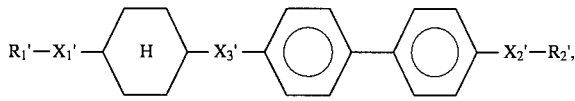 (VIa)

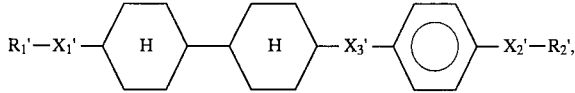 (VIb)

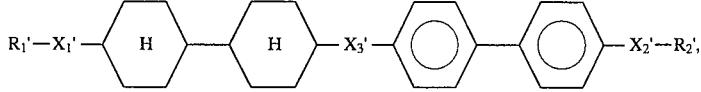 (VIc)

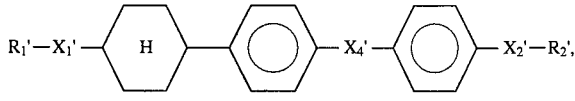 (VId)

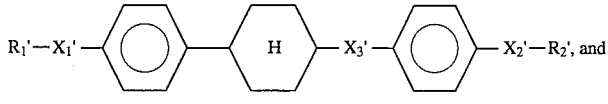 (VIe)

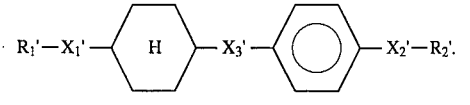 (VIf)

Herein, $R_1'$ and $R_2'$ respectively denote a linear or branched alkyl group having 1–18 carbon atoms capable of including one or two or more non-neighboring methylene groups which can be replaced with —CH halogen- and capable of further including one or two or more non-neighboring methylene groups other than those directly connected to $X_1'$ or $X_2'$ which can be replaced with at least one species of

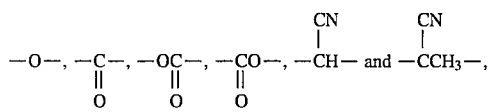

with proviso that $R_1'$ and $R_2'$ respectively do not connect to a ring structure when $R_1'$ and $R_2'$ respectively denote a halogenated alkyl group containing one methylene group replaced with —CH halogen-.

Further, preferred examples of $R_1'$ and $R_2'$ may respectively include those represented by the following groups (i) to (vii):

i) a linear alkyl group having 1–15 carbon atoms;

ii)

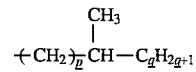

wherein p denotes an integer of 0–5 and q denotes an integer of 1–11 (optically active or inactive);

iii)

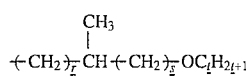

wherein r denotes an integer of 0–6, s denotes 0 or 1, and t denotes an integer of 1–14 (optically active or inactive);

iv)

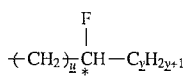

wherein u denotes 0 or 1 and v denotes an integer of 1–16;

v)

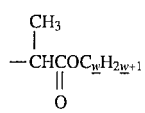

wherein w denotes an integer of 1–15 (optically active or inactive);

vi)

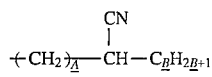

wherein A denotes an integer of 0–2 and B denotes an integer of 1–15 (optically active or inactive); and vii)

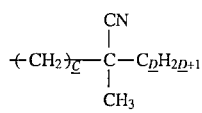

wherein C denotes an integer of 0–2 and D denotes an integer of 1–15 (optically active or inactive).

In the above-mentioned formula (III), more preferred compounds thereof may include those represented by the formulas (IIIaa) to (IIIdc):

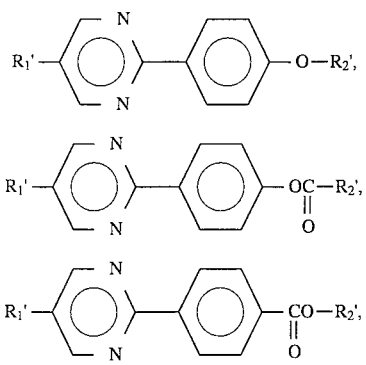

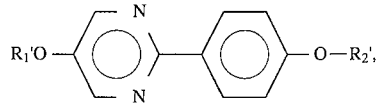

(IIIad)

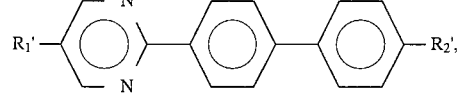

(IIIba)

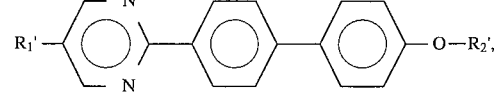

(IIIbb)

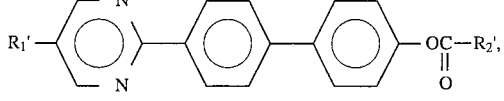

(IIIbc)

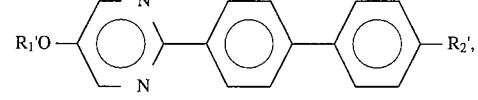

(IIIbd)

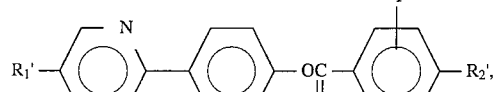

(IIIca)

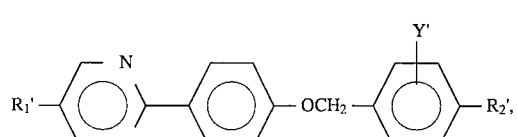

(IIIcb)

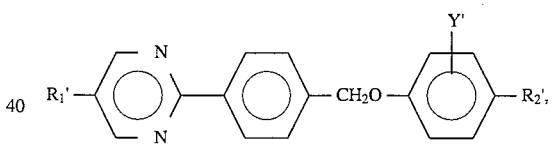

(IIIcc)

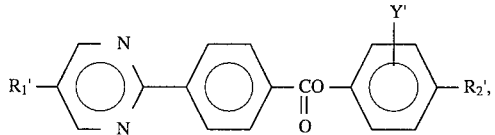

(IIIcd)

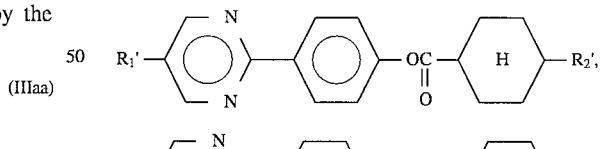

(IIIda)

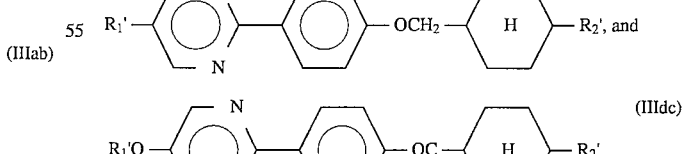

(IIIdb)

(IIIdc)

In the above-mentioned formula (IV), more preferred compounds thereof may include those represented by the formulas (IVaa) to (IVcd):

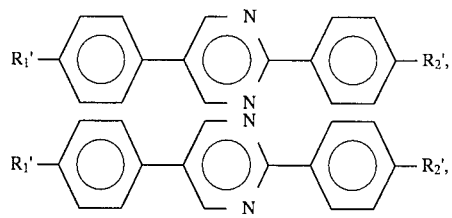 (IVaa)
 (IVab)
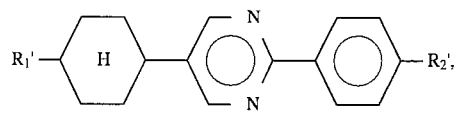 (IVba)
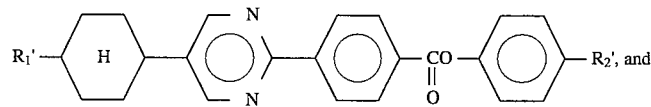 (IVca)
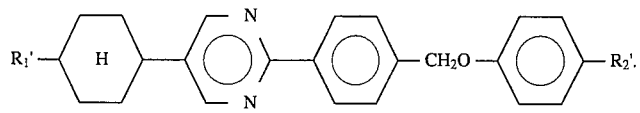 (IVcb)
In the above-mentioned formula (V), more preferred compounds thereof may include those represented by the formulas (Vaa) to (Vbf):
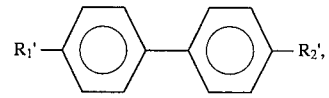 (Vaa)
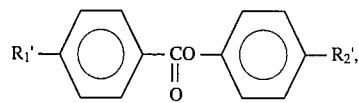 (Vab)
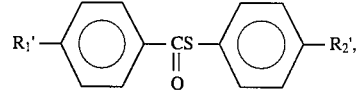 (Vac)
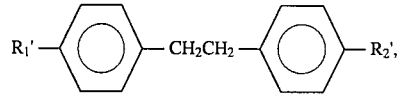 (Vad)
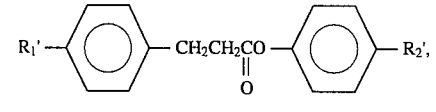 (Vae)
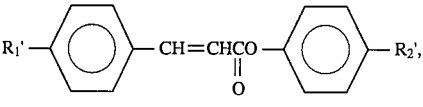 (Vaf)
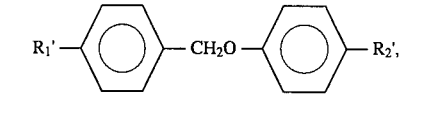 (Vag)
(Vah)
-continued
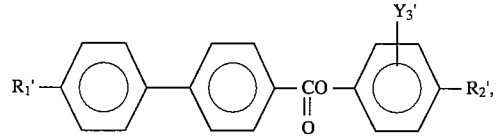 (Vba)
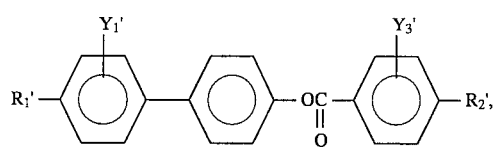 (Vbb)
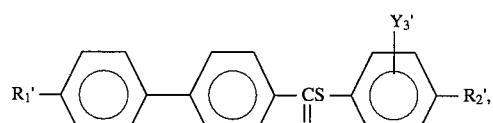 (Vbc)
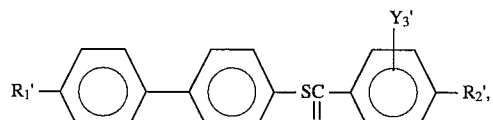 (Vbd)
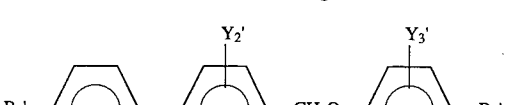 (Vbe)
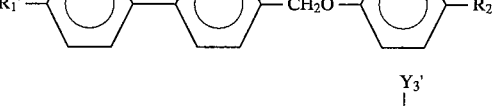 (Vbf)
In the above-mentioned formula (VI), more preferred compounds thereof may include those represented by the formulas (VIaa) to (VIfa):

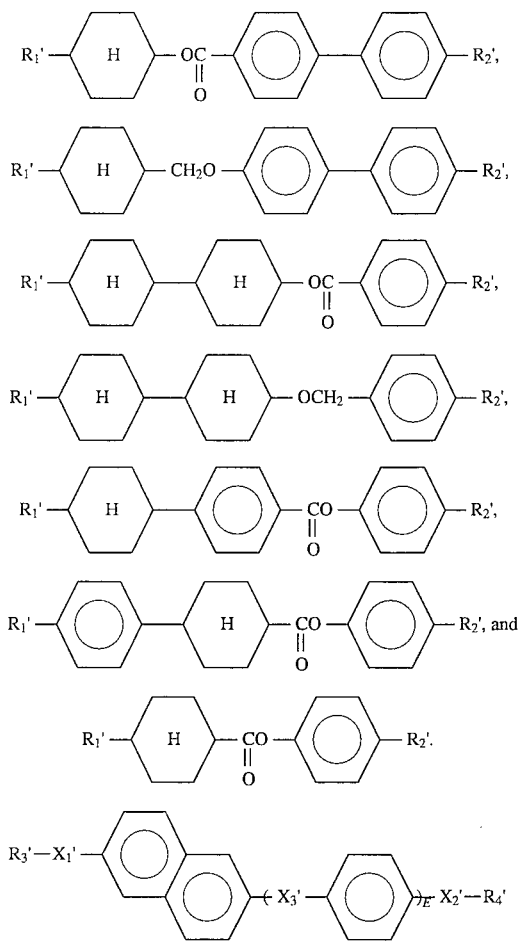

wherein E denotes 0 or 1; $X_1'$ and $X_2'$ respectively denote a single bond,

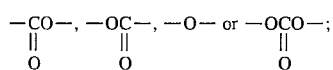

and $X_3'$ denotes a single bond,

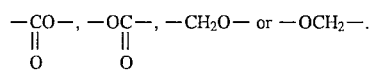

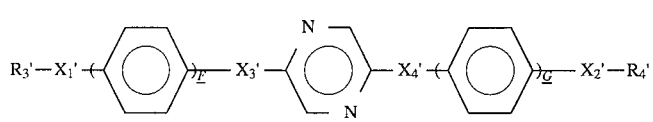

wherein F and G respectively denote 0 or 1; $X_1'$ and $X_2'$ respectively denote a single bond,

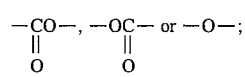

and $X_3'$ and $X_4'$ respectively denote a single bond,

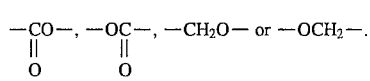

In the above formula (VII), preferred compounds thereof may include those represented by the following formulas (VIIa) and (VIIb):

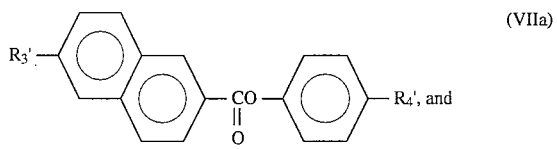

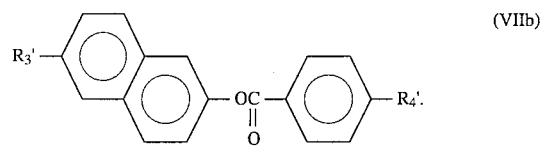

In the above formula (VIII), preferred compounds thereof may include those represented by the following formulas (VIIIa) and (VIIIb).

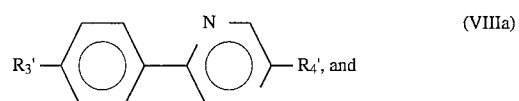

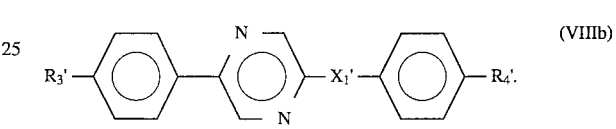

More preferred compounds of the formula (VIII) may include those represented by the formulas (VIIIaa) to (VIIIbb):

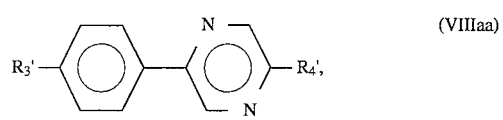

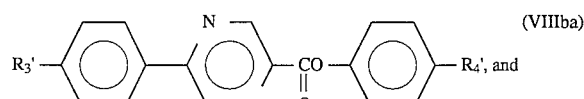

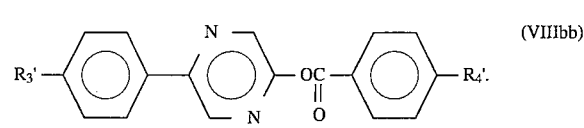

Herein, $R_3'$ and $R_4'$ respectively denote a linear or branched alkyl group having 1–18 carbon atoms capable of including one or two or more non-neighboring methylene groups which can be replaced with —CH halogen- and capable of further including one or two or more non-neighboring methylene groups other than those directly connected to $X_1'$ or $X_2'$ which can be replaced with at least one species of

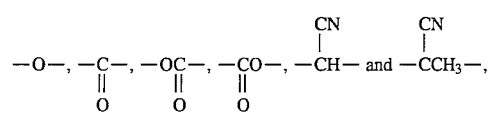

with proviso that $R_3'$ and $R_4'$ respectively do not connect to a ring structure when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1–15 carbon atoms;
ii)

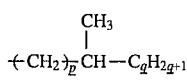

wherein $p$ denotes an integer of 0–5 and $q$ denotes an integer of 1–11 (optically active or inactive);
iii)

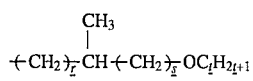

wherein $r$ denotes an integer of 0–6, $s$ denotes 0 or 1, and $t$ denotes an integer of 1–14 (optically active or inactive);
iv)

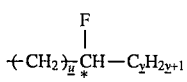

wherein $u$ denotes an integer of 0 or 1 and $v$ denotes an integer of 1–16;
v)

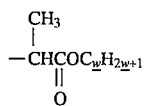

wherein $w$ denotes an integer of 1–15 (optically active or inactive);
vi)

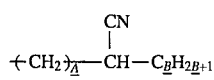

wherein $A$ denotes an integer of 0–2 and $B$ denotes an integer of 1–15 (optically active or inactive); and
vii)

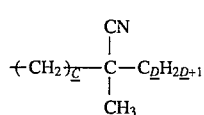

wherein $C$ denotes an integer of 0–2 and $D$ denotes an integer of 1–15 (optically active or inactive).

wherein $H$ and $J$ respectively denote 0 or 1 with proviso that $H+J=0$ or 1; $X_1'$- and $X_2'$ respectively denote a single bond,

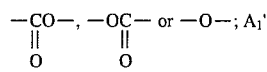

denotes

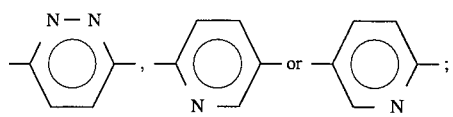

and $X_3'$ and $X_4'$ respectively denote a single bond,

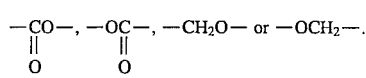

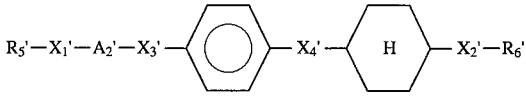

(X)

wherein $X_1'$ and $X_2'$ respectively denote a single bond,

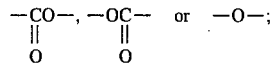

$A_2'$ denotes

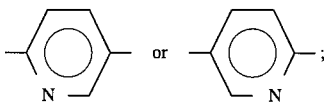

and $X_3'$ and $X_4'$ respectively denote a single bond,

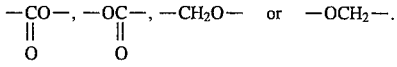

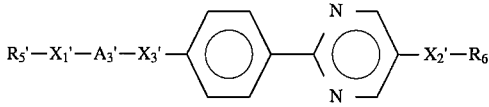

(XI)

wherein $X_1'$ and $X_2'$ respectively denote a single bond,

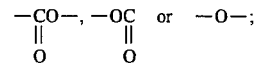

$A_3'$ denotes

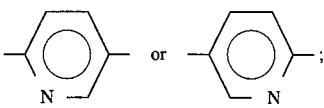

(IX)

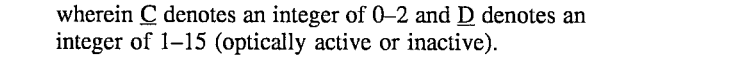

and $X_3'$ respectively denotes a single bond,

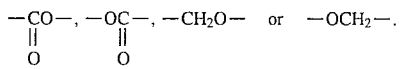

In the above formula (IX), preferred compounds thereof may include those represented by the following formulas (IXa) to (IXc):

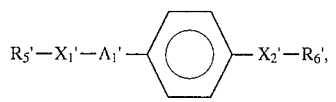 (IXa)

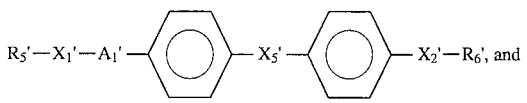 (IXb)

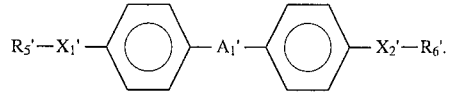 (IXc)

In the above formula (X), preferred compounds thereof may include those represented by the following formulas (Xa) and (Xb):

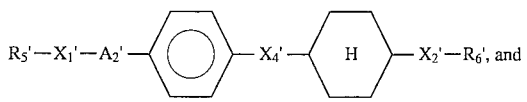 (Xa)

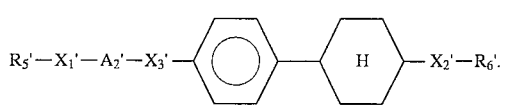 (Xb)

In the above-mentioned formula (IX), more preferred compounds thereof may include those represented by the formulas (IXaa) to (IXcc):

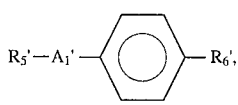 (IXaa)

 (IXab)

 (IXac)

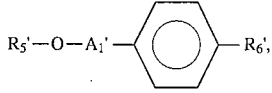 (IXad)

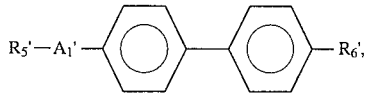 (IXba)

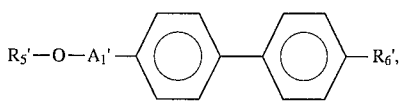 (IXbb)

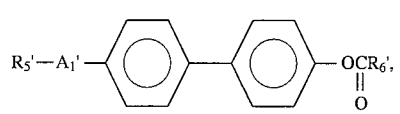 (IXbc)

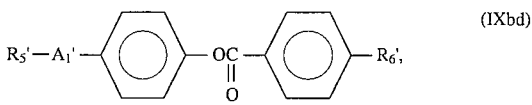 (IXbd)

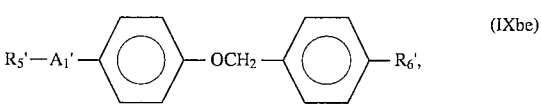 (IXbe)

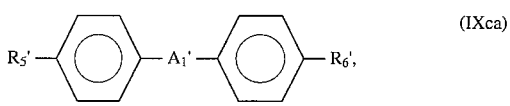 (IXca)

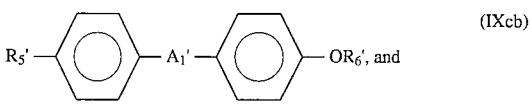 (IXcb)

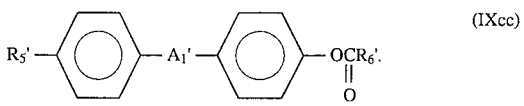 (IXcc)

In the above-mentioned formula (X), more preferred compounds thereof may include those represented by the formulas (Xaa) to (Xbb):

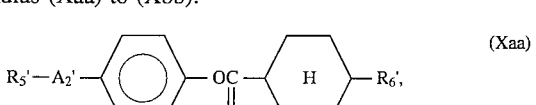 (Xaa)

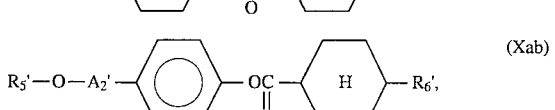 (Xab)

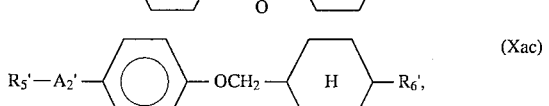 (Xac)

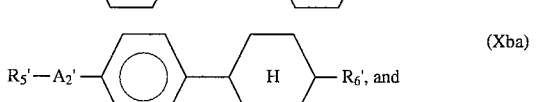 (Xba)

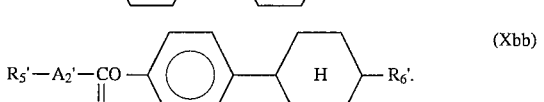 (Xbb)

In the above formula (XI), preferred compounds thereof may include those represented by the following formulas (XIa) to (XIg):

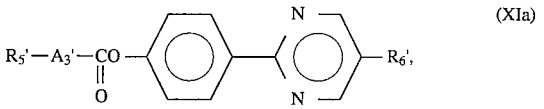 (XIa)

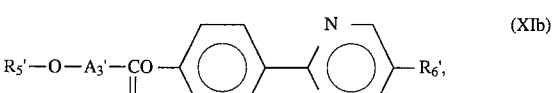 (XIb)

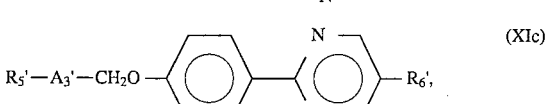 (XIc)

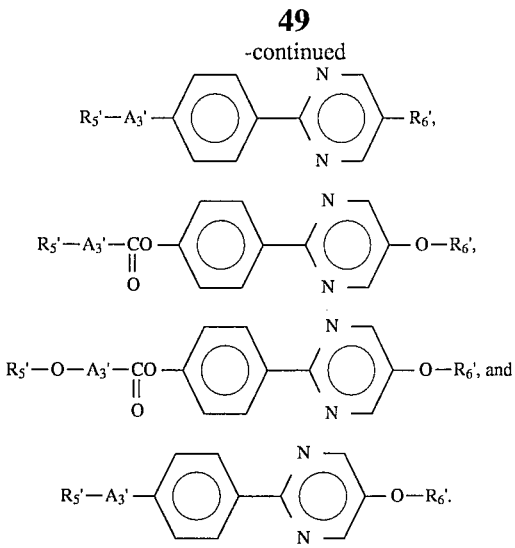

Herein, $R_5'$ and $R_6'$ respectively denote a linear or branched alkyl group having 1–18 carbon atoms capable of including one or two or more non-neighboring methylene groups other than those directly connected to $X_1'$ or $X_2'$ which can be replaced with at least one species of

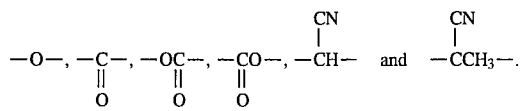

Further, preferred examples of $R_5'$ and $R_6'$ may respectively include those represented by the following groups (i) to (vi):

i) a linear alkyl group having 1–15 carbon atoms;

ii)

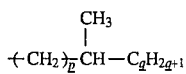

wherein $\underline{p}$ denotes an integer of 0–5 and $\underline{q}$ denotes an integer of 1–11 (optically active or inactive);

iii)

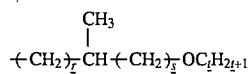

wherein $\underline{r}$ denotes an integer of 0–6, $\underline{s}$ denotes 0 or 1, and $\underline{t}$ denotes an integer of 1–14 (optically active or inactive);

iv)

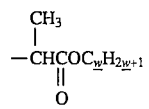

wherein $\underline{w}$ denotes an integer of 1–15 (optically active or inactive);

v)

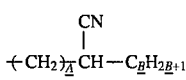

wherein $\underline{A}$ denotes an integer of 0–2 and $\underline{B}$ denotes an integer of 1–15 (optically active or inactive); and vi)

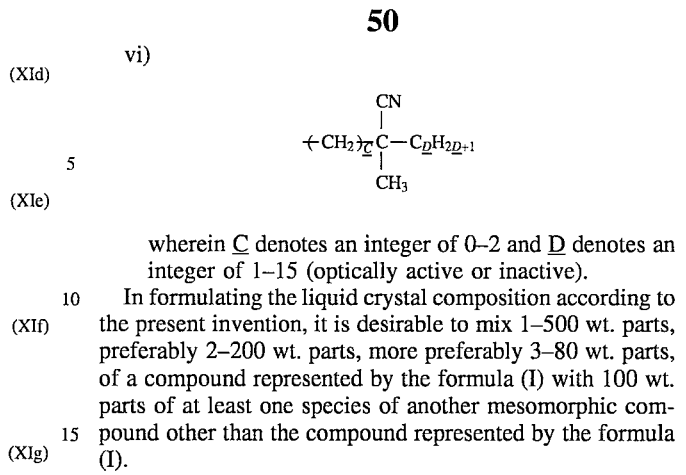

wherein $\underline{C}$ denotes an integer of 0–2 and $\underline{D}$ denotes an integer of 1–15 (optically active or inactive).

In formulating the liquid crystal composition according to the present invention, it is desirable to mix 1–500 wt. parts, preferably 2–200 wt. parts, more preferably 3–80 wt. parts, of a compound represented by the formula (I) with 100 wt. parts of at least one species of another mesomorphic compound other than the compound represented by the formula (I).

Alternatively, the liquid crystal composition may desirably contain 1–80 wt. %, preferably 1–60 wt. %, more preferably 1–40 wt. % of a mesomorphic compound represented by the formula (I).

Further, when two or more species of the compounds represented by the formula (I) are used, the two or more species of the compounds of the formula (I) may be used in a total amount of 1–500 wt. parts, preferably 2–200 wt. parts, more preferably 3–80 wt. parts, per 100 wt. parts of at least one species of another mesomorphic compound other than the two or more species of the compounds of the formula (I).

Alternatively, the liquid crystal composition may desirably contain 1–80 wt. %, preferably 1–60 wt. %, more preferably 1–40 wt. %, of the two or more species of the compounds represented by the formula (I).

The liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the liquid crystal may show a phase transition series comprising isotropic phase-Ch phase (cholesteric phase)-SmA phase (smectic A phase)-SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
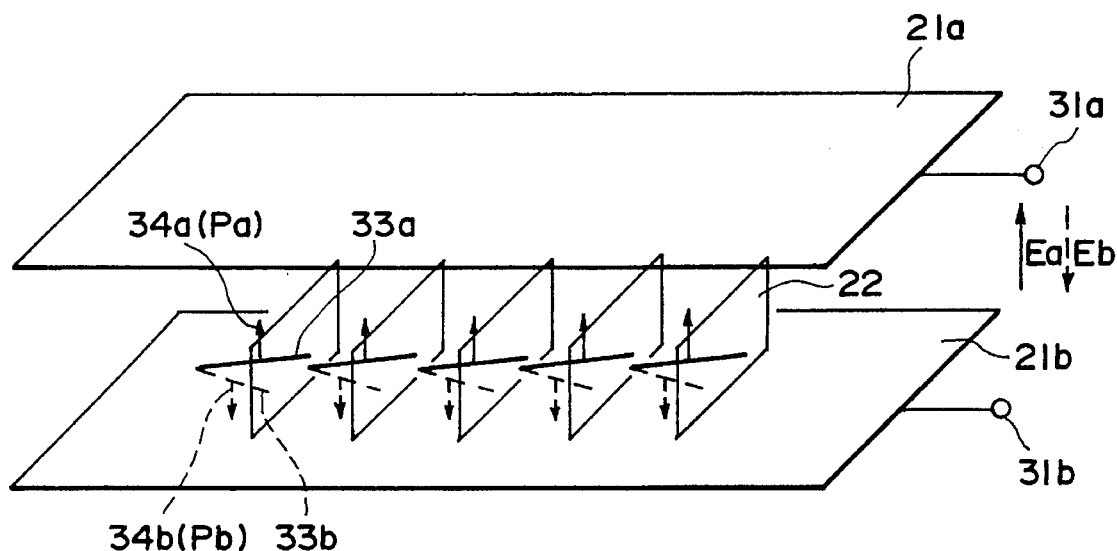

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the abovementioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
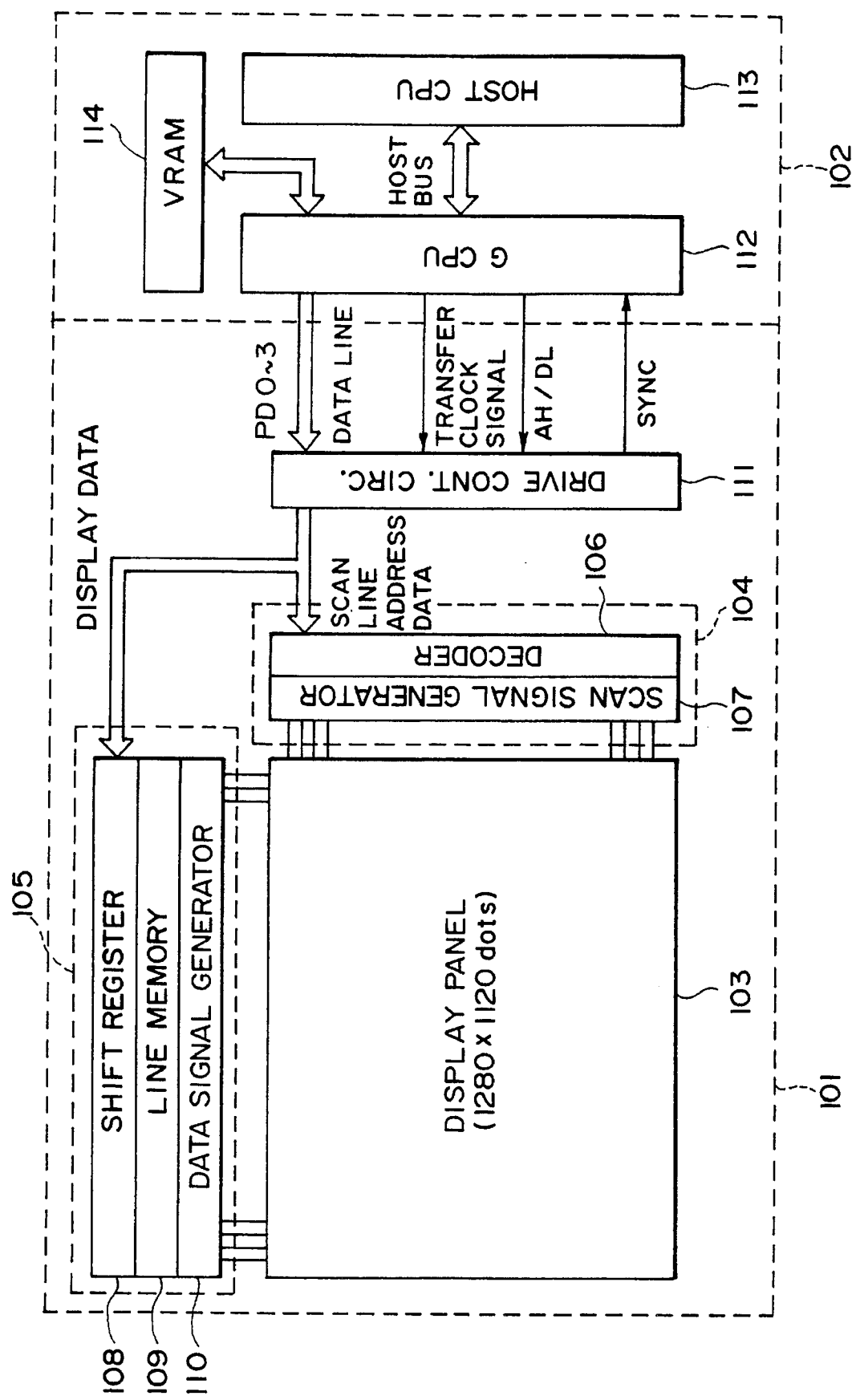
FIG. 4 is a block diagram showing a display apparatus comprising a liquid crystal device utilizing ferroelectricity of a liquid crystal composition and a graphic controller.
Figure 5:
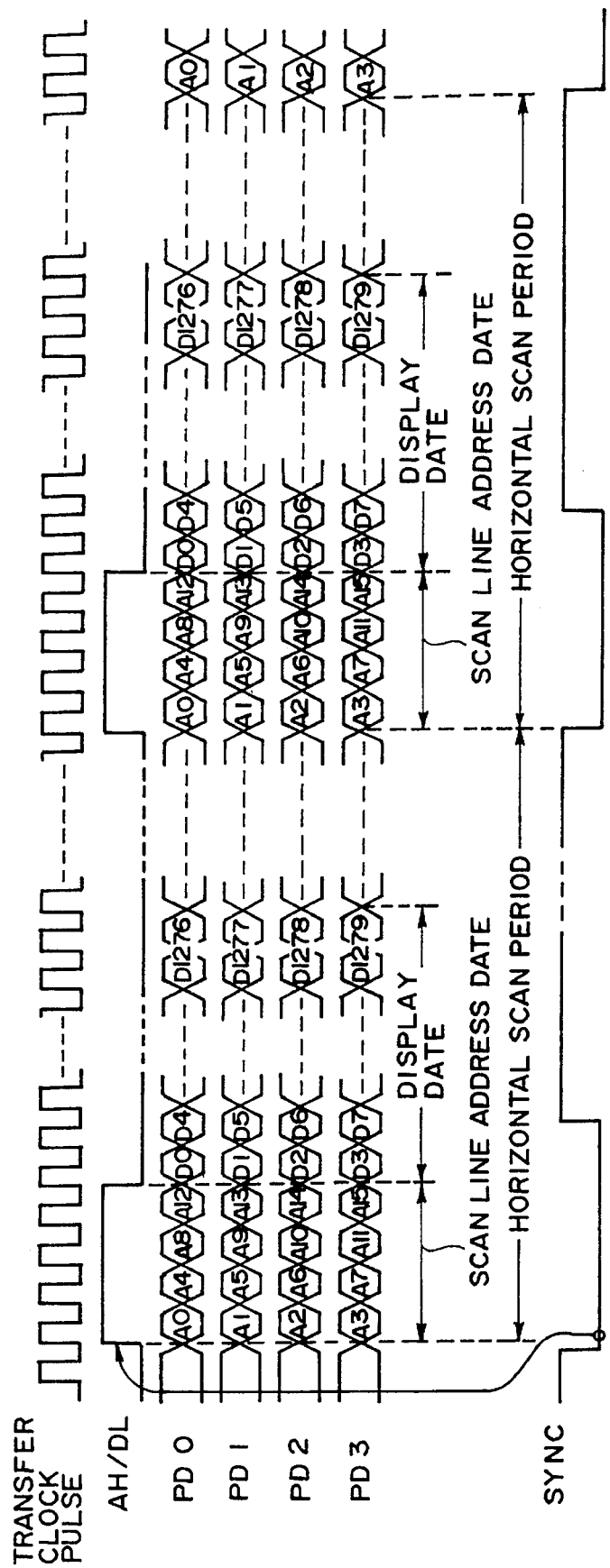
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Image data are generated in a graphic controller 102 in an apparatus body and transferred to a display panel 103 by signal transfer means shown in FIG. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control method according to the present invention is principally realized in the graphic controller 102.

A light source is disposed at the back of the display panel 103.

Hereinbelow, the present invention will be explained more specifically with reference to examples. It is however to be understood that the present invention is not restricted to these examples.

EXAMPLE 1

2-(4-hexylphenyl)-5-(4-pentanoyloxyphenyl)-thiazole (Example Compound No. 1-53) as synthesized through the following steps i)–v).

Step i) 4-methoxyphenacyl bromide was prepared by brominating 4-methoxyacetophenone with tetrabutylammonium tribromine in the same manner as in "Bull. Chem. Soc. Jpn.", 60, 1159 (1987).

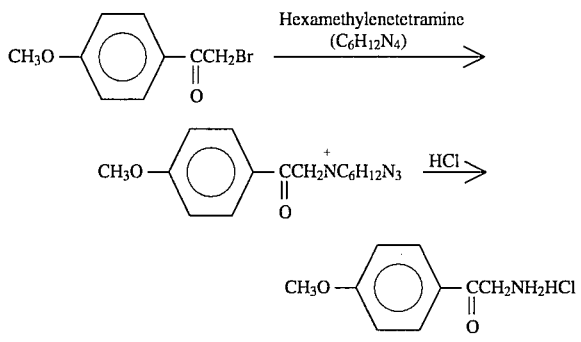

4-methoxyphenacylamine hydrochloride was synthesized from 4-methoxyphenacyl bromide through the above reaction scheme according to a process shown in "Ber.", 44 1542 (1911)

Step iii)

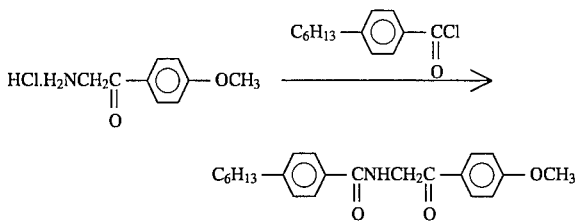

To a solution of 26.9 g (120 mM) of 4-hexylbenzoyl chloride in 206 ml of pyridine, 22.2 g (110 mM) of 4-methoxyphenacylamine hydrochloride was gradually added in 30 minutes under cooling and stirring at −10° to −5° C., followed by stirring for 30 minutes at −10° to −5° C. and heat-refluxing of 1 hour under stirring. After the reaction, the reaction mixture was cooled to room temperature and poured into 600 ml of cool water to precipitate a crystal. The crystal was recovered by filtration, washed with water and recrystallized from ethanol to obtain 19.6 g of 4-hexylbenzoyl-4'-methoxyphenacylamine (Yield: 50.5%).

Step iv)

In a 300 ml-round-bottomed flask, 19.6 g (55.5 mM) of 4-hexylbenzoyl-4'-methoxyphenacylamine, 24.3 g (60.1 mM) of Lawesson's reagent and 97 ml of tetrahydrofuran were placed, followed by heat-refluxing for 1 hour under stirring. After the reaction, the reaction mixture was poured into a solution of 19 g of sodium hydroxide in 2 liters of water to precipitate a crystal. The crystal was recovered by filtration, successively washed with water and ethanol and recrystallized from ethanol to obtain 15.9 g of 2-(4-hexylphenyl)-5-(4-methoxyphenyl)thiazole (Yield: 82.9%).

Then, in a 300 ml-three-necked flask, 13.9 g (39.3 mM) of 2-(4-hexylphenyl)-5-(4-methoxyphenyl)tiazole, 76.5 ml of acetic acid and 69.5 ml of 47%-hydrobromic acid were placed, followed by heat-stirring for 16 hours at 100°–110° C. After the reaction, the reaction mixture was poured into cool water, followed by extraction with ethyl acetate. The organic layer was successively washed with water, 5%-sodium hydrogenecarbonate aqueous solution and water, followed by distilling-off of the solvent under reduced pressure. The residue was dissolved in a mixture solvent of ethanol/chloroform=1/1, followed by decolorization with activated carbon and distilling-off of the solvent under reduced pressure. The resultant residue was recrystallized two times from toluene to obtain 10.0 g of 2-(4-hexylphenyl)-5-(4-hydroxyphenyl)thiazole (Yield: 75.8%).

Step v)

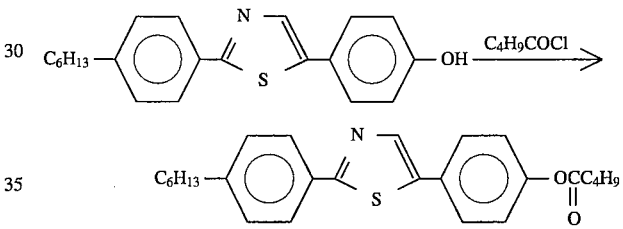

To a solution of 0.60 g (1.78 mM) of 2-(4-hexylphenyl)-5-(4-hydroxyphenyl)thiazole in 10 ml of pyridine, 0.36 ml (3.03 mM) of pentanoyl chloride was added on an ice water bath under stirring, followed by further stirring for 2 hours at room temperature. After the reaction, the reaction mixture was poured into 100 ml of ice water to precipitate a crystal. The crystal was recovered by filtration and dissolved in toluene, followed by drying with anhydrous sodium sulfate and distilling-off of the solvent. The residue was purified by silica gel column chromatography (eluent:toluene) and recrystallized from a mixture solvent of toluene-methanol to obtain 0.64 g of 2-(4-hexylphenyl)-5-(4-pentanoyloxyphenyl)thiazole (Yield: 85.4%).

Phase transition temperature (°C.)

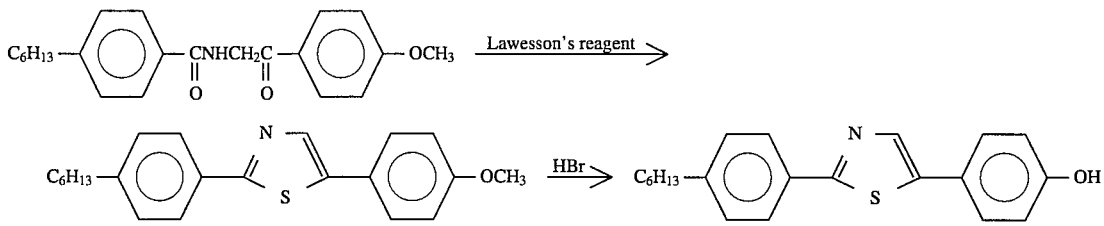

Cryst. $\xrightleftharpoons[96.0]{101.9}$ SmC $\xrightleftharpoons[127.7]{128.5}$ N $\xrightleftharpoons[148.6]{149.4}$ Iso.

Herein, the respective symbols denote the following phases, Iso.: isotropic phase, N: nematic phase, SmC: smectic phase, and Cryst.: crystal.

EXAMPLE 2

2-(4-hexylphenyl)-5-(4-heptanoyloxyphenyl)thiazole (Example Compound No. 1-54) was prepared in the same manner as in Step v) of Example 1 except that heptanoyl chloride was used instead of pentanoyl chloride (Yield: 79.6%).

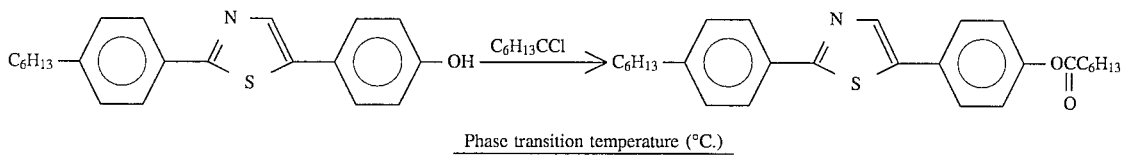

Phase transition temperature (°C.)

Cryst. $\xrightleftharpoons[<-10]{73.1}$ Sm3 $\xrightleftharpoons[80.0]{83.2}$ SmC $\xrightleftharpoons[138.5]{139.3}$ N $\xrightleftharpoons[147.9]{148.7}$ Iso.

Sm3: smectic phase of higher order than SmA and SmC (un-identified)

EXAMPLE 3

2-(4-hexylphenyl)-5-(4-nonanoyloxyphenylthiazole (Example Compound No. 1-55) was prepared in the same manner as in Example 2 (Yield: 69.1%).

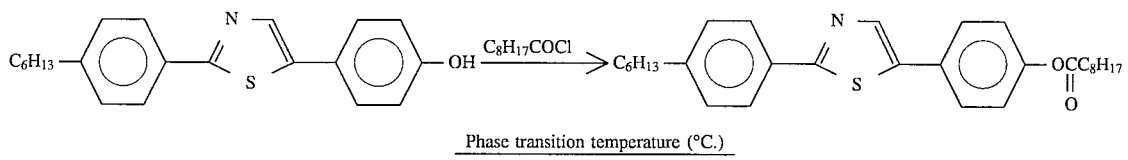

Phase transition temperature (°C.)

Cryst. $\xrightleftharpoons[45.4]{58.0}$ Sm3 $\xrightleftharpoons[74.9]{75.8}$ SmC $\xrightleftharpoons[145.6]{146.4}$ N $\xrightleftharpoons[147.1]{148.1}$ Iso.

EXAMPLE 4

2-(4-hexylphenyl)-5-(4-undecanoyloxyphenyl)thiazole (Example Compound No. 1-57) was prepared in the same manner as in Example 2 (Yield: 69.0%).

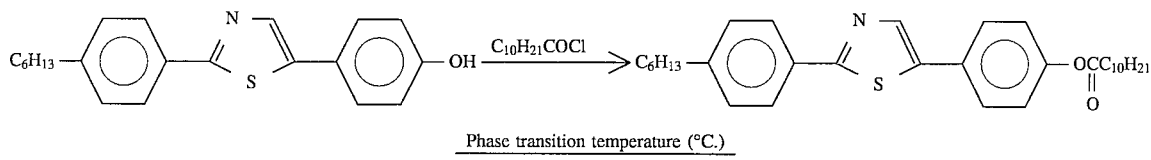

Phase transition temperature (°C.)

Cryst. $\xrightleftharpoons[42.0]{74.9}$ Sm3 $\xrightleftharpoons[85.3]{86.2}$ SmC $\xrightleftharpoons[146.2]{147.0}$ Iso.

EXAMPLE 5

2-(4-octylphenyl)-5-(4-nonanoyloxyphenyl)-thiazole (Example Compound No. 1-63) was prepared in the same manner as in Example 1 (Yield: 84.3%).

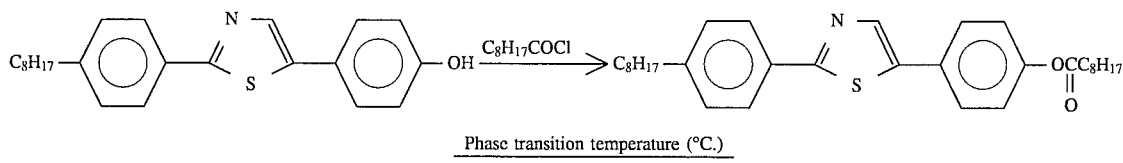

Phase transition temperature (°C.)

$$\text{Cryst.} \underset{<-10}{\overset{59.4}{\rightleftarrows}} \text{Sm4} \underset{68.4}{\overset{74.5}{\rightleftarrows}} \text{Sm3} \underset{77.5}{\overset{78.5}{\rightleftarrows}} \text{SmC} \underset{147.4}{\overset{148.5}{\rightleftarrows}} \text{Iso.}$$

Sm4: smectic phase of higher order than SmA and SmC (un-identified)

EXAMPLE 6

2-decyl-5-(4-heptanoyloxyphenyl)thiazole (Example Compound No. 1-130) was synthesized through the following steps i)–iii).

Step i)

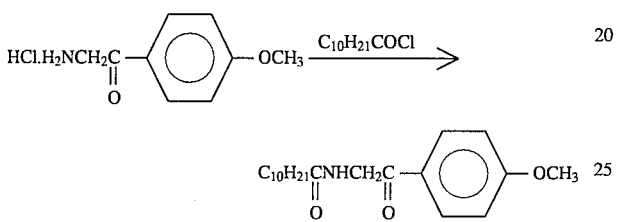

To a solution of 22.0 g (108 mM) of undecanoyl chloride in 185 ml of pyridine, 22.2 g (110 mM) of 4-methoxyphenacylamine hydrochloride was gradually added in 30 minutes under cooling and stirring below −5° C., followed by stirring for 30 minutes below −5° C. and heat-refluxing of 1 hour under stirring. After the reaction, the reaction mixture was cooled to room temperature and poured into 1 liter of cool water to precipitate a crystal. The crystal was recovered by filtration, washed with water and recrystallized from ethanol to obtain 13.9 g of decanoyl-4-methoxyphenacylamine (Yield: 38.8%).

Step ii)

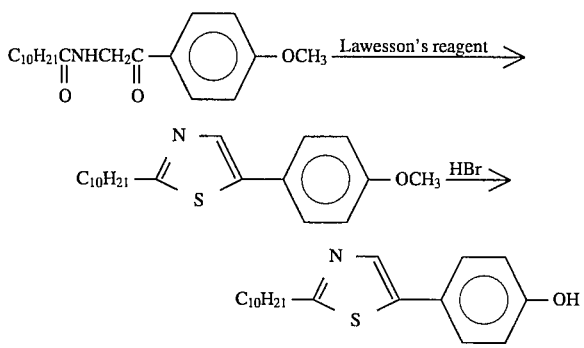

In a 200 ml-round-bottomed flask, 13.9 g (41.7 mM) of decanoyl-4-methoxyphenacylamine, 18.3 g (45.2 mM) of Lawesson's reagent and 73 ml of tetrahydrofuran were placed, followed by heat-refluxing for 1 hour under stirring. After the reaction, the reaction mixture was poured into a solution of 14.4 g of sodium hydroxide in 1.5 liters of water to precipitate a crystal. The crystal was recovered by filtration, washed with water and recrystallized from ethanol to obtain 11.6 g of 2-decyl-5-(4-methoxyphenyl)thiazole (Yield: 83.9%).

Then, in a 500 ml-three-necked flask, 11.6 g (35.0 mM) of 2-decyl-5-(4-methoxyphenyl)tiazole, 93 ml of acetic acid and 102 ml of 47%-hydrobromic acid were placed, followed by heat-stirring for 16 hours at 100°–110° C. After the reaction, the reaction mixture was poured into cool water, followed by extraction with benzene. The organic layer was successively washed with water, 5%-sodium hydrogenecarbonate aqueous solution and water, followed by distilling-off of the solvent under reduced pressure. The residue was purified by silica gel column chromatography (eluent: chloroform) and recrystallized from toluene to obtain 7.0 g of 2-decyl-5-(4-hydroxyphenyl )thiazole (Yield: 63.1%).

Step iii)

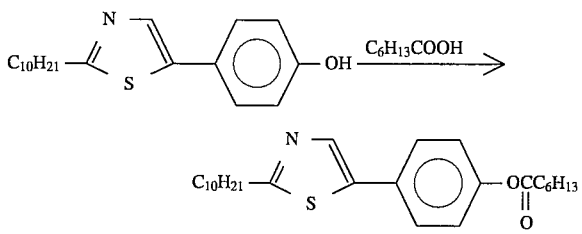

In a 50 ml-round-bottomed flask, 0.60 g (1.89 mM) of 2-decyl-5-(4-hydroxyphenyl)thiazole, 0.28 ml (1.97 mM) of heptanoic acid and 15 ml of dichloromethane were placed and mixed. To the solution, 0.39 g (1.89 mM) of N,N'-dicyclohexylcarbodiimide and 0.03 g of 4-pyrrolidinopyridine were successively added under stirring at room temperature, followed by further stirring for 2 hours at room temperature. After stirring, the mixture was left standing overnight at room temperature to precipitate N,N'-dicyclohexylurea. The resultant N,N'-dicyclohexylurea was filtered off and the solvent of the filtrate was distilled-off under reduced pressure. The residue was purified by silica gel column chromatography (eluent: toluene) and recrystallized from acetone to obtain 0.62 g of 2-decyl-5-(4-heptanoyloxyphenyl)thiazole (Yield: 76.4%).

Phase transition temperature (°C.)

$$\text{Cryst.} \underset{57.7}{\overset{73.6}{\rightleftarrows}} \text{Iso.} \quad 65.0 \quad \text{Sm3}$$

EXAMPLE 7

2-decyl-5-(4-nonanoyloxyphenyl)thiazole (Example Compound No. 1-132) was prepared in the same manner as in Example 6 (Yield: 34.9%).

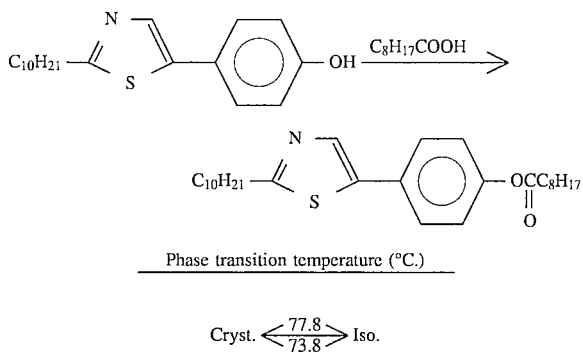

Phase transition temperature (°C.)

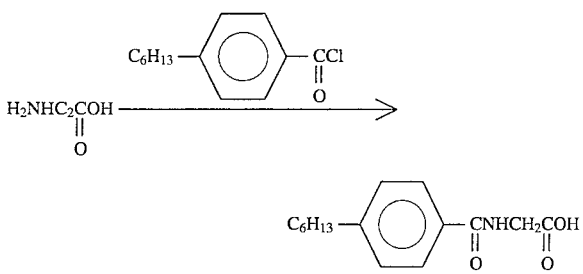

EXAMPLE 8

2-(4-hexylphenyl)-5-(4-nonylphenyl)thiazole (Example Compound No. 1-12) was synthesized through the following steps i)–iii).

Step i)

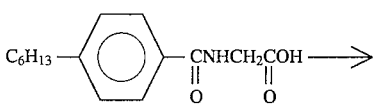

In a 200 ml-three-necked flask, 3.34 g (44.5 mM) of glycine, 0.89 g (22.3 mM) of sodium hydroxide and 16.7 ml of distilled water were placed and mixed. To the solution, 16.7 ml of dioxane was added. To the resultant mixture, a solution of 0.89 g (22.3 mM) of sodium hydroxide in 8.4 ml of distilled water and a solution of 5.00 g (22.2 mM) of 4-hexylbenzoyl chloride in 33.4 ml of dioxane were gradually added simultaneously at −1° to 3° C. by dropping funnels, respectively, followed by stirring for 30 minutes at 1°–2° C. After the reaction, 2.3 ml of concentrated hydrochloric acid was added to the reaction mixture to precipitate a crystal. The crystal was recovered by filtration and washed with water, followed by drying and recrystallization from ethyl acetate to obtain 4.86 g of N-(4-hexylbenzoyl)glycine (Yield: 82.9%).

Step ii)

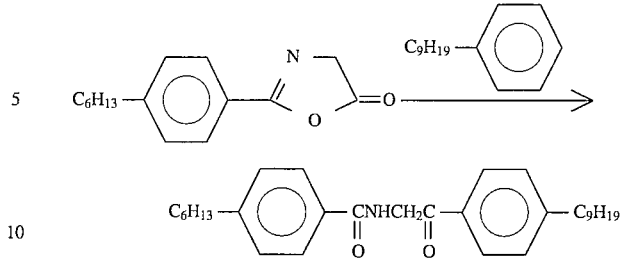

In a 50 ml-three-necked flask, 1.00 g (3.80 mM) of N-(4-hexylbenzoyl)glycine and 19 ml of dry benzene were placed. To the mixture, 0.53 ml (3.81 mM) of triethylamine was added at room temperature under stirring, followed by addition of 0.37 ml (3.87 mM) of ethyl chloroformate and further stirring for 20 minutes at room temperature to precipitate triethylamine hydrochloride. The resultant hydrochloride was filtered off and the solvent of the filtrate was distilled off. The residue was dried under reduced pressure to obtain 2-(4-hexylphenyl)-5-oxazolone.

Then, in a 50 ml-three-necked flask, 4 ml of dry nonylbenzene was placed and 1.52 g (11.4 mM) of powdered anhydrous aluminum chloride was added thereto on an ice bath under stirring. To the mixture, a solution of the above-prepared 2-(4-hexylphenyl)-5-oxazolone in dry nonylbenzene was gradually added on the ice bath under stirring. After the addition, the ice bath was removed, followed by stirring for 1.5 hours at room temperature. After the reaction, the reaction mixture was poured into a mixture of 30 g of ice and 8.4 ml of hydrochloric acid, followed by addition of 100 ml of ethyl acetate and stirring at room temperature. The organic layer was washed with water and dried with anhydrous sodium sulfate, followed by distilling-off of the solvent under reduced pressure. Then, hexane was added to the residue to precipitate a crystal. The crystal was recovered by filtration and washed with hexane to obtain 0.71 g of 4-hexylbenzoyl-4'-nonylphenacylamine (Yield: 41.6%).

Step iii)

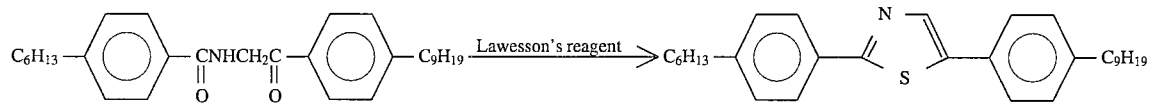

In a 30 ml-round-bottomed flask, 0.65 g (1.45 mM) of 4-hexylbenzoyl-4'-nonylphenacylamine, 0.62 g (1.53 mM) of Lawesson's reagent and 10 ml of tetrahydrofuran were placed, followed by heat-refluxing for 55 min. under stirring. After the reaction, the reaction mixture was poured into a solution of 0.46 g of sodium hydroxide in 100 ml of ice water to precipitate a crystal. The crystal was recovered by filtration and dissolved in toluene, followed by washing with water, drying with anhydrous sodium sulfate and distilling-off of the solvent. The residue was purified by silica gel column chromatography and recrystallized two times from a mixture solvent of toluene-methanol to obtain 0.37 g of 2-(4-hexylphenyl)-5-(4-nonylphenyl)thiazole (Yield: 57.2%).

Phase transition temperature (°C.)

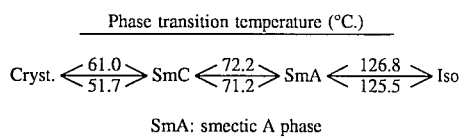

SmA: smectic A phase

EXAMPLE 9

0.74 g of 2-(4-hexylphenyl)-5-(4-hexylphenyl)thiazole (Example Compound No. 1-9) was prepared in the same manner as in Example 8 with the yields of respective steps shown below.

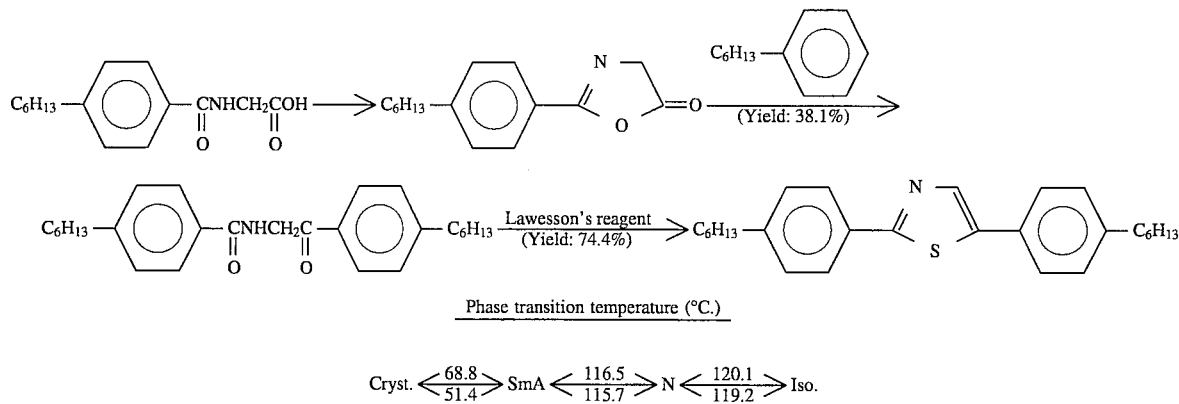

Phase transition temperature (°C.)

$$\text{Cryst.} \underset{51.4}{\overset{68.8}{\rightleftarrows}} \text{SmA} \underset{115.7}{\overset{116.5}{\rightleftarrows}} \text{N} \underset{119.2}{\overset{120.1}{\rightleftarrows}} \text{Iso.}$$

EXAMPLE 10

2-nonyl-5-(4'-hexylbiphenyl-4-yl)thiazole (Example Compound No. 1-141) was synthesized through the following reaction schemes in the same manner as in Example 8 except that carbon disulfide was used as a reaction solvent of Friedel-Crafts reaction.

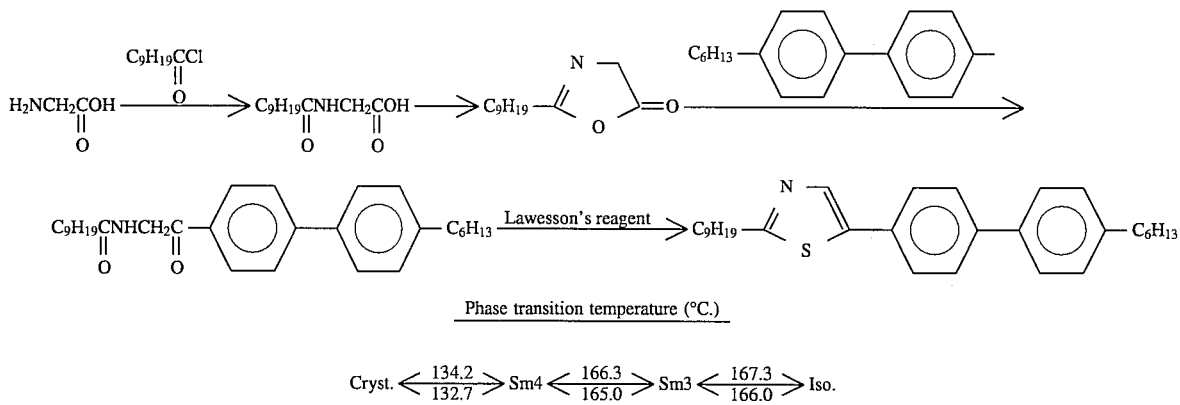

Phase transition temperature (°C.)

$$\text{Cryst.} \underset{132.7}{\overset{134.2}{\rightleftarrows}} \text{Sm4} \underset{165.0}{\overset{166.3}{\rightleftarrows}} \text{Sm3} \underset{166.0}{\overset{167.3}{\rightleftarrows}} \text{Iso.}$$

EXAMPLE 11

A liquid crystal composition A was prepared by mixing the following compounds in respectively indicated proportions.

| Structural formula | wt. parts |
|---|---|
| 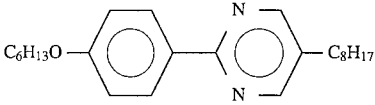 | 46.14 |
| 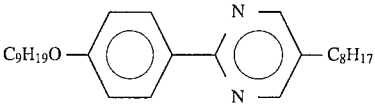 | 23.07 |
| 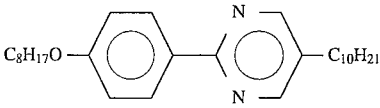 | 11.54 |
| 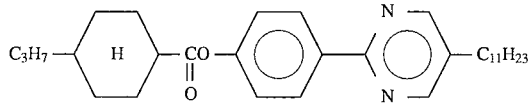 | 3.56 |
| 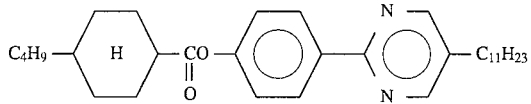 | 3.56 |
| 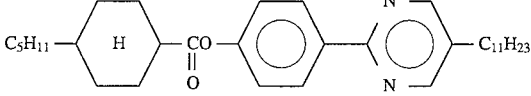 | 7.13 |
| 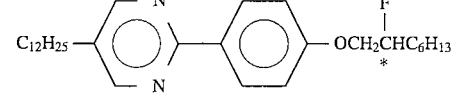 | 2.50 |
| 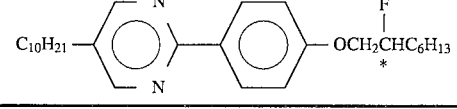 | 2.50 |

The liquid crystal composition A was further mixed with the following Example Compound 1-130 in the proportions indicated below to provide a liquid crystal composition B.

| Ex. Comp. No. | Structural formula | wt. parts |
|---|---|---|
| 1-130 | 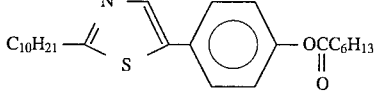 | 5 |
| | Composition A | 95 |

The liquid crystal composition B showed the following phase transition series.

Phase transition temperature (°C.)

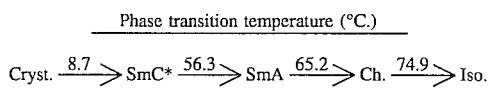

SmC*: chiral smectic C phase, and

Ch.: cholesteric phase.

EXAMPLE 12

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 11 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

|  | 10° C. | 30° C. | 45° C. |
|---|---|---|---|
| Response time (μsec) | 564 | 243 | 143 |
| Ps (nC/cm$^2$) | 3.98 | 2.95 | 1.77 |

Further, the device was assembled into a display apparatus shown in FIG. 4 to effect display.

EXAMPLE 13

A liquid crystal composition C was prepared by mixing the following compounds in respectively indicated proportions.

| Structural formula | wt. parts |
|---|---|
| $C_6H_{13}O$—⟨phenyl⟩—⟨pyrimidinyl(N,N)⟩—$C_8H_{17}$ | 51.57 |
| $C_9H_{19}O$—⟨phenyl⟩—⟨pyrimidinyl(N,N)⟩—$C_8H_{17}$ | 25.79 |
| $C_8H_{17}O$—⟨phenyl⟩—⟨pyrimidinyl(N,N)⟩—$C_{10}H_{21}$ | 12.89 |
| $C_3H_7$—⟨cyclohexyl-H⟩—CO-O—⟨phenyl⟩—⟨pyrimidinyl(N,N)⟩—$C_{11}H_{23}$ | 1.19 |
| $C_4H_9$—⟨cyclohexyl-H⟩—CO-O—⟨phenyl⟩—⟨pyrimidinyl(N,N)⟩—$C_{11}H_{23}$ | 1.19 |
| $C_5H_{11}$—⟨cyclohexyl-H⟩—CO-O—⟨phenyl⟩—⟨pyrimidinyl(N,N)⟩—$C_{11}H_{23}$ | 2.37 |
| $C_{12}H_{25}$—⟨pyrimidinyl(N,N)⟩—⟨phenyl⟩—OCH$_2$CH*($F$)C$_6$H$_{13}$ | 2.50 |
| $C_{10}H_{21}$—⟨pyrimidinyl(N,N)⟩—⟨phenyl⟩—OCH$_2$CH*($F$)C$_6$H$_{13}$ | 2.50 |

The liquid crystal composition C was further mixed with the following Example Compound No. 1-55 in the proportions indicated below to provide a liquid crystal composition D.

| Ex. Comp. No. | Structural formula | wt. parts |
|---|---|---|
| 1-155 | 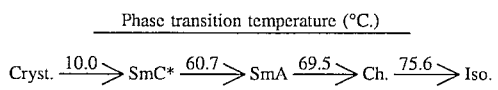 | 10 |
| | Composition C | 90 |

The liquid crystal composition D showed the following phase transition series.

Phase transition temperature (°C.)

Cryst. $\xrightarrow{10.0}$ SmC* $\xrightarrow{60.7}$ SmA $\xrightarrow{69.5}$ Ch. $\xrightarrow{75.6}$ Iso.

A ferroelectric liquid crystal device was prepared in the same manner as in Example 12 except for using the composition D. The ferroelectric liquid crystal device was subjected to measurement of the magnitude of spontaneous polarization Ps and response time in the same manner as in Example 12, whereby the following results were obtained.

|  | 10° C. | 30° C. | 45° C. |
|---|---|---|---|
| Response time (μsec) | 419 | 201 | 122 |
| Ps (nC/cm²) | 3.06 | 2.56 | 1.56 |

COMPARATIVE EXAMPLE 1

2-(4-hexylphenyl)-5-(nonanoyloxyphenyl)-1,3,4-thiadiazole was synthesized through the following reaction schemes.

The above-prepared compound showed the following phase transition series.

Phase transition temperature (°C.)

Cryst. $\underset{44.0}{\overset{58.2}{\rightleftarrows}}$ Sm3 $\underset{64.8}{\overset{68.1}{\rightleftarrows}}$ SmC $\underset{171.7}{\overset{172.6}{\rightleftarrows}}$ N $\underset{175.4}{\overset{176.1}{\rightleftarrows}}$ Iso.

The liquid crystal composition C was mixed with the above-prepared compound in the proportions indicated below to provide a liquid crystal composition E.

| Structural formula | wt. parts |
|---|---|
| 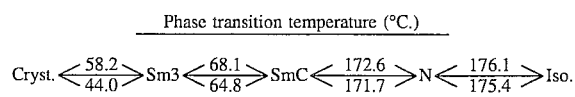 | 10 |
| Composition C | 90 |

The liquid crystal E showed the following phase transition series.

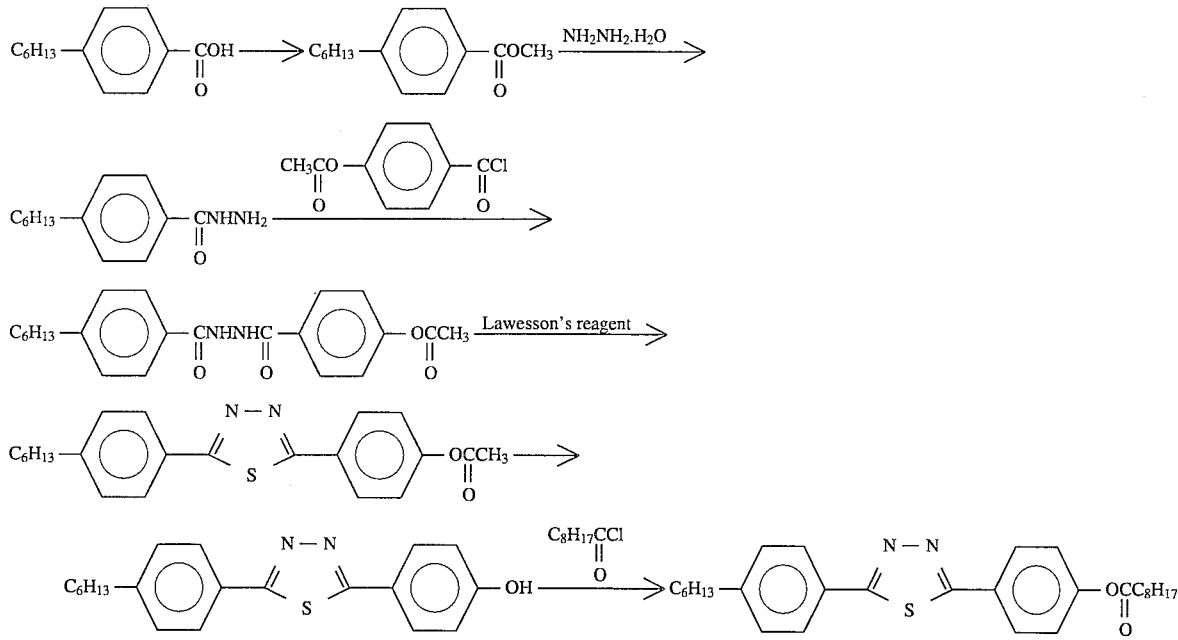

Phase transition temperature (°C.)

Cryst. $\xrightarrow{10.2}$ SmC* $\xrightarrow{59.8}$ SmA $\xrightarrow{67.3}$ Ch. $\xrightarrow{77.0}$ Iso.

A ferroelectric liquid crystal device was prepared in the same manner as in Example 12 except for using the composition E. The ferroelectric liquid crystal device was subjected to measurement of the magnitude of spontaneous polarization Ps and response time in the same manner as in Example 12, whereby the following results were obtained.

|  | 10° C. | 30° C. | 45° C. |
|---|---|---|---|
| Response time (μsec) | 544 | 246 | 155 |
| Ps (nC/cm$^2$) | 4.80 | 3.62 | 2.52 |

As is apparent from Example 13 and Comparative Example 1, the liquid crystal composition D according to the present invention had a smaller response time than that of the liquid crystal composition E though the liquid crystal composition D had a smaller Ps than that of the liquid crystal composition E. As a result, we have found that the composition comprising the mesomorphic compound having a thiazole ring of the present invention has a lower viscosity and higher response speed than those of the composition comprising the mesomorphic compound having a 1,3,4-thiadiazole ring.

EXAMPLE 14

A liquid crystal composition F was prepared by mixing the following compounds in respectively indicated proportions.

| Structural formula | wt. parts |
|---|---|
| 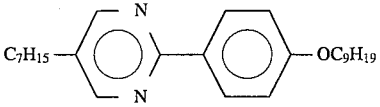 | 12 |
| 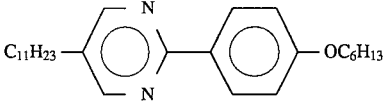 | 10 |
| 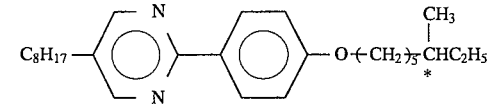 | 10 |
| 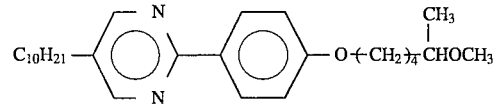 | 3 |
| 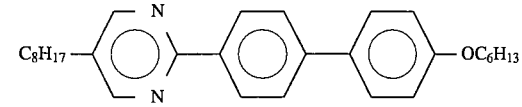 | 8 |
| 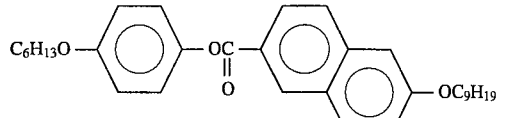 | 4 |
| 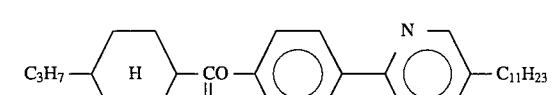 | 6 |
| 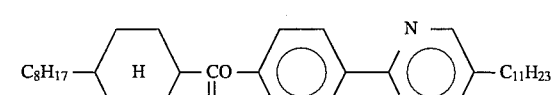 | 2 |
| 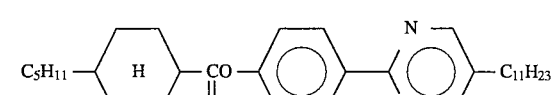 | 8 |

-continued

| Structural formula | wt. parts |
|---|---|
| 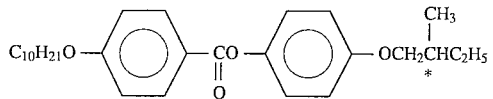 | 15 |
| 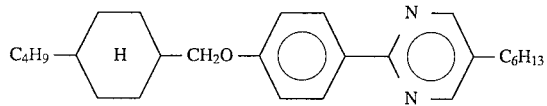 | 7 |
| 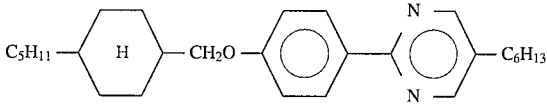 | 7 |
| 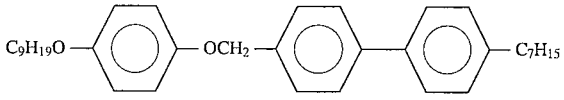 | 4 |
| 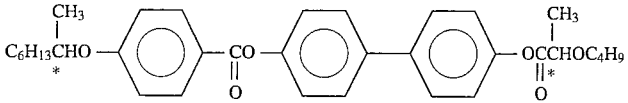 | 2 |
| 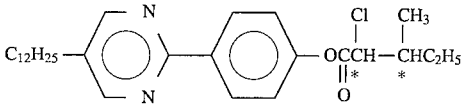 | 2 |

The liquid crystal composition F was further mixed with the following Example Compounds in the proportions indicated below to provide a liquid crystal composition G.

| Ex. Comp. No. | Structural formula | wt. parts |
|---|---|---|
| 1-18 | 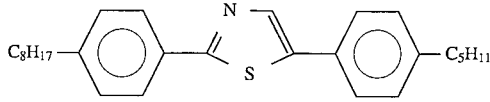 | 4 |
| 1-47 | 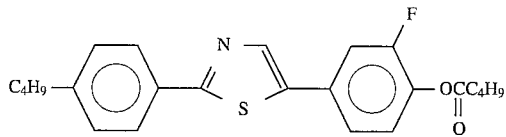 | 2 |
| 1-154 | 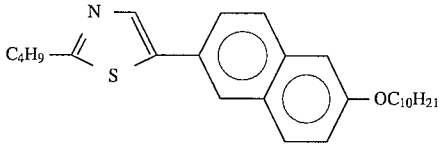 | 2 |
| | Composition F | 92 |

A ferroelectric liquid crystal device was prepared in the same manner as in Example 12 except for using the composition G. The ferroelectric liquid crystal device was subjected to measurement of response time in the same manner as in Example 10, whereby the following results were obtained.

| | 10° C. | 25° C. | 40° C. |
|---|---|---|---|
| Response time (μsec) | 723 | 351 | 191 |

COMPARATIVE EXAMPLE 2

A ferroelectric liquid crystal device was prepared in the same manner as in Example 12 except that the liquid crystal composition F prepared in Example 14 was injected into a cell. The measured values of the response time of the device were as follows.

|  | 10° C. | 25° C. | 40° C. |
| --- | --- | --- | --- |
| Response time (μsec) | 784 | 373 | 197 |

EXAMPLE 15

A liquid crystal composition H was prepared by mixing the following example compounds in the indicated proportions with the liquid crystal composition F prepared in Example 14.

|  | 10° C. | 25° C. | 40° C. |
| --- | --- | --- | --- |
| Response time (μsec) | 731 | 357 | 197 |

EXAMPLE 16

A liquid crystal composition I was prepared by mixing the following example compounds in the indicated proportions with the liquid crystal composition F prepared in Example 14.

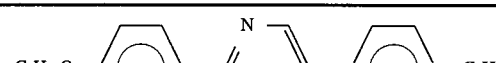

| Ex. Comp. No. | Structural formula | wt. parts |
| --- | --- | --- |
| 1-79 | $C_8H_{17}O$—⬡—(N/S)—⬡—$C_6H_{13}$ | 4 |
| 1-97 | $C_{10}H_{21}CO(=O)$—⬡—(N/S)—⬡—$C_6H_{13}$ | 4 |
| 1-109 | $C_6H_{13}O$—⬡—(N/S)—⬡—$OCC_8H_{17}(=O)$ | 2 |
| Composition F |  | 90 |

A ferroelectric liquid crystal device was prepared in the same manner as in Example 12 except that the above liquid crystal composition H was used, and the device was subjected to measurement of optical response time. The results of the measurement are shown below.

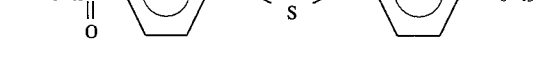

| Ex. Comp. No. | Structural formula | wt. parts |
| --- | --- | --- |
| 1-16 | $C_6H_{13}O(=O)$—⬡—(N/S)—⬡—$C_6H_{13}$ | 4 |
| 1-91 | $C_5H_{11}\overset{F}{\underset{*}{C}H}CH_2O$—⬡—(N/S)—⬡—$C_8H_{17}$ | 2 |
| 1-118 | $C_8H_{17}$—⬢(H)—(N/S)—⬡—$OCC_6H_{13}(=O)$ | 4 |
| Composition F |  | 90 |

A ferroelectric liquid crystal device was prepared in the same manner as in Example 12 except that the above liquid crystal composition I was used, and the device was subjected to measurement of optical response time. The results of the measurement are shown below.
|  | 10° C. | 25° C. | 40° C. |
| --- | --- | --- | --- |
| Response time (μsec) | 699 | 334 | 180 |
EXAMPLE 17
A liquid crystal composition J was prepared by mixing the following compounds in respectively indicated proportions.
| Structural formula | wt. parts |
| --- | --- |
| 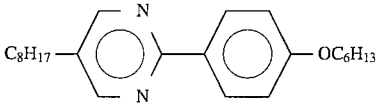 | 10 |
| 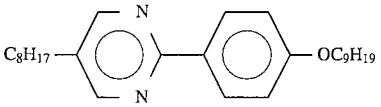 | 5 |
| 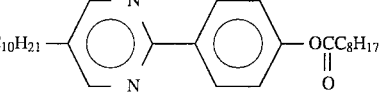 | 7 |
| 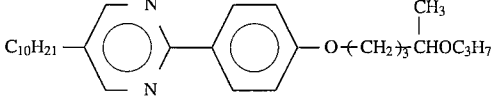 | 7 |
| 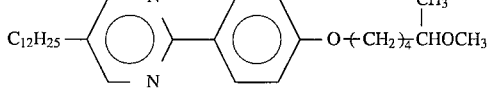 | 6 |
| 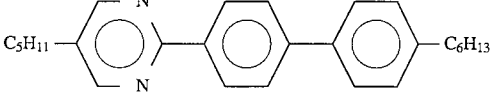 | 5 |
| 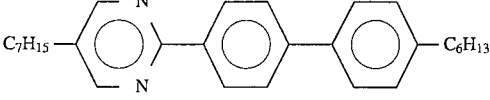 | 5 |
| 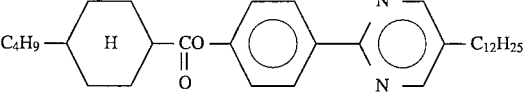 | 8 |
| 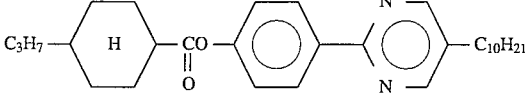 | 8 |
| 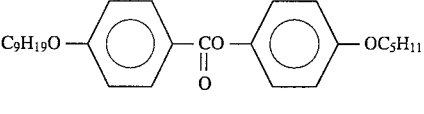 | 20 |
| 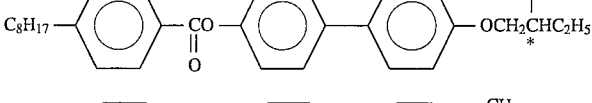 | 5 |
| 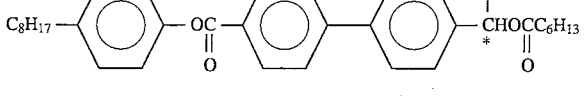 | 5 |

| Structural formula | wt. parts |
|---|---|
| C$_6$H$_{13}$—⌬—OCH$_2$—⌬—⌬—C$_7$H$_{15}$ | 6 |
| C$_{12}$H$_{25}$—(N⌬N)—⌬—OCH$_2$CHC$_6$H$_{13}$ (F, *) | 3 |

The liquid crystal composition J was further mixed with the following Example Compounds in the proportions indicated below to provide a liquid crystal composition K.

| Ex. Comp. No. | Structural formula | wt. parts |
|---|---|---|
| 1-54 | C$_6$H$_{13}$—⌬—(N/S)=⌬—OCC$_6$H$_{13}$ (‖ O) | 2 |
| 1-126 | C$_6$H$_{13}$—(N/S)=⌬—C$_8$H$_{17}$ | 4 |
| 1-136 | C$_8$H$_{17}$—(N/S)=⌬—OC(‖O)—(⌬N)—C$_4$H$_9$ | 4 |
| Composition J | | 90 |

A ferroelectric liquid crystal device was prepared in the same manner as in Example 12 except for using the composition K. The ferroelectric liquid crystal device was subjected to measurement of response time, in the same manner as in Example 10, whereby the following results were obtained.

| | 10° C. | 25° C. | 40° C. |
|---|---|---|---|
| Response time (μsec) | 583 | 288 | 146 |

COMPARATIVE EXAMPLE 3

A ferroelectric liquid crystal device was prepared in the same manner as in Example 12 except that the liquid crystal composition J prepared in Example 17 was injected into a cell. The measured values of the response time of the device were as follows.

| | 10° C. | 25° C. | 40° C. |
|---|---|---|---|
| Response time (μsec) | 653 | 317 | 159 |

EXAMPLE 18

A liquid crystal composition L was prepared by mixing the following example compounds in the indicated proportions with the liquid crystal composition J prepared in Example 17.

| Ex. Comp. No. | Structural formula | wt. parts |
|---|---|---|
| 1-58 | C$_6$H$_{13}$—⌬—(N/S)=⌬—OCC$_{12}$H$_{25}$ (‖O) | 2 |

| Ex. Comp. No. | Structural formula | wt. parts |
|---|---|---|
| 1-78 | $C_6H_{13}O-\bigcirc-CH=N-CH=CH-\bigcirc-C_6H_{13}$ (with S in thiazole) | 4 |
| 1-133 | $C_4H_9-\text{(thiazole)}-CH=CH-\text{(pyridine)}-OC_8H_{17}$ | 4 |
| Composition J | | 90 |

A ferroelectric liquid crystal device was prepared in the same manner as in Example 12 except that the above liquid crystal composition L was used, and the device was subjected to measurement of optical response time. The results of the measurement are shown below.

| | 10° C. | 25° C. | 40° C. |
|---|---|---|---|
| Response time (μsec) | 601 | 296 | 151 |

EXAMPLE 19

A liquid crystal composition M was prepared by mixing the following example compounds in the indicated proportions with the liquid crystal composition J prepared in Example 17.

| Ex. Comp. No. | Structural formula | wt. parts |
|---|---|---|
| 1-69 | $C_8H_{17}-\bigcirc-\text{(thiazole)}-CH=CH-\bigcirc-OC(=O)(CH_2)_2CHOC_3H_7$ with $CH_3$ | 2 |
| 1-169 | $C_4H_9-\text{(pyridine)}-\text{(thiazole)}-CH=CH-\bigcirc-OCC_{10}H_{21}(=O)$ | 4 |
| 1-19 | $C_8H_{17}-\bigcirc-\text{(thiazole)}-CH=CH-\bigcirc-C_8H_{17}$ | 2 |
| Composition J | | 92 |

A ferroelectric liquid crystal device was prepared in the same manner as in Example 12 except that the above liquid crystal composition M was used, and the device was subjected to measurement of optical response time. The results of the measurement are shown below.

| | 10° C. | 25° C. | 40° C. |
|---|---|---|---|
| Response time (μsec) | 605 | 299 | 158 |

EXAMPLE 20

A liquid crystal composition N was prepared by mixing the following example compounds in the indicated propor-

| Ex. Comp. No. | Structural formula | wt. parts |
|---|---|---|
| 1-156 | $C_6H_{13}$-(thiazole)-CH=CH-(naphthalene)-$OCC_6H_{13}$(=O) | 2 |
| 1-64 | $C_8H_{17}$-(phenyl)-(thiazole)-(phenyl)-$OCC_{10}H_{21}$(=O) | 2 |
| 1-187 | $C_6H_{17}$-(thiophene)-(thiazole)-(phenyl)-$OCC_{10}H_{21}$(=O) | 4 |
| Composition J | | 92 |

A ferroelectric liquid crystal device was prepared in the same manner as in Example 12 except that the above liquid crystal composition N was used, and the device was subjected to measurement of optical response time. The results of the measurement are shown below.

|  | 10° C. | 25° C. | 40° C. |
|---|---|---|---|
| Response time (μsec) | 590 | 291 | 150 |

EXAMPLE 21

A liquid crystal composition O was prepared by mixing the following compounds in respectively indicated proportions.

| Structural formula | wt. parts |
|---|---|
| $C_9H_{19}$-(pyrazine)-(phenyl)-$OC_9H_{19}$ | 6 |
| $C_{10}H_{21}$-(pyrazine)-(phenyl)-$OC_8H_{17}$ | 6 |
| $C_8H_{17}$-(pyridine)-(phenyl)-$O(CH_2)_5CH^*C_2H_5(CH_3)$ | 7 |
| $C_{11}H_{23}O$-(pyrimidine)-(phenyl)-$O(CH_2)_2CH^*C_2H_5(CH_3)$ | 14 |
| $C_{10}H_{21}$-(pyridine)-(phenyl)-$C_6H_{13}$ | 8 |
| $C_6H_{13}$-(pyrazine)-(phenyl)-(phenyl)-$C_4H_9$ | 4 |

-continued

| Structural formula | wt. parts |
|---|---|
| C$_8$H$_{17}$—⟨phenyl⟩—⟨pyridyl-N⟩—⟨phenyl⟩—OC$_5$H$_{11}$ | 2 |
| C$_3$H$_7$—⟨H⟩—COO—⟨phenyl⟩—⟨pyrimidyl⟩—C$_{12}$H$_{25}$ | 10 |
| C$_5$H$_{11}$—⟨H⟩—COO—⟨phenyl⟩—⟨pyrimidyl⟩—C$_{12}$H$_{25}$ | 5 |
| C$_{10}$H$_{21}$O—⟨phenyl⟩—C(=S)O—⟨phenyl⟩—OC$_8$H$_{17}$ | 10 |
| C$_6$H$_{13}$—⟨phenyl⟩—COO—⟨phenyl⟩—⟨phenyl⟩—OCH$_2$CH(CH$_3$)C$_2$H$_5$ | 7 |
| C$_3$H$_7$—⟨H⟩—CH$_2$O—⟨phenyl⟩—⟨pyrimidyl⟩—C$_8$H$_{17}$ | 7 |
| C$_{10}$H$_{21}$—⟨phenyl⟩—⟨phenyl⟩—OCH$_2$—⟨phenyl⟩—C$_7$H$_{15}$ | 5 |
| C$_{12}$H$_{25}$—⟨pyrimidyl⟩—⟨phenyl⟩—OCH$_2$C*H(F)C$_5$H$_{11}$ | 2 |
| C$_5$H$_{11}$—⟨H⟩—COO—⟨phenyl⟩—OCH$_2$C*H(F)C$_6$H$_{13}$ | 2 |
| C$_{12}$H$_{25}$O—⟨phenyl⟩—⟨pyrimidyl⟩—COO(CH$_2$)$_3$C*H(CH$_3$)C$_2$H$_5$ | 2 |
| C$_{12}$H$_{25}$O—⟨phenyl⟩—⟨pyrimidyl⟩—O(CH$_2$)$_3$CH(CH$_3$)OC$_3$H$_7$ | 3 |

The liquid crystal composition O was further mixed with the following Example Compounds in the proportions indicated below to provide a liquid crystal composition P.

| Ex. Comp. No. | Structural formula | wt. parts |
| --- | --- | --- |
| 1-121 | $C_8H_{17}$—⬡—CH=N—S—CH=CH—⬡—COC$_6$H$_{13}$ (‖O) | 2 |
| 1-149 | $C_6H_{13}$—[N,S thiazole]—CH=CH—⬡—OC(=O)—⬡(H)—$C_8H_{17}$ | 2 |
| 1-151 | $C_9H_{19}$—[N,S thiazole]—CH=CH—⬡—[pyrimidine N,N]—$C_{10}H_{21}$ | 4 |
| | Composition O | 92 |

A ferroelectric liquid crystal device was prepared in the same manner as in Example 12 except for using the composition P. In the ferroelectric liquid crystal device, a monodomain with a good and uniform alignment characteristic was observed. The ferroelectric liquid crystal device was subjected to measurement of response time and observation of a switching state, etc. in the same manner as in Example 12, whereby the following results were obtained.

|  | 10° C. | 25° C. | 40° C. |
| --- | --- | --- | --- |
| Response time (μsec) | 637 | 328 | 181 |

COMPARATIVE EXAMPLE 4

A ferroelectric liquid crystal device was prepared in the same manner as in Example 12 except that the liquid crystal composition O prepared in Example 21 was injected into a cell. The measured values of the response time of the device were as follows.

|  | 10° C. | 25° C. | 40° C. |
| --- | --- | --- | --- |
| Response time (μsec) | 668 | 340 | 182 |

EXAMPLE 22

A liquid crystal composition Q was prepared by mixing the following example compounds in the indicated proportions with the liquid crystal composition D prepared in Example 21.

| Ex. Comp. No. | Structural formula | wt. parts |
| --- | --- | --- |
| 1-138 | $C_{10}H_{21}$—[N,S thiazole]—CH=CH—⬡—OCCHC$_8$H$_{17}$ (F, *, ‖O) | 1 |
| 1-142 | $C_{10}H_{21}$—[N,S thiazole]—CH=CH—⬡—⬡—OCC$_5$H$_{11}$ (‖O) | 3 |
| 1-181 | $C_6H_{13}O$—⬡—CH=[N,S thiazole]=CH—$C_{10}H_{21}$ | 3 |
| | Composition O | 93 |

A ferroelectric liquid crystal device was prepared in the same manner as in Example 12 except that the above liquid crystal composition Q was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time (μsec) | 622 | 323 | 175 |

As is apparent from the results shown in the above Examples 14–22, the ferroelectric liquid crystal devices containing the liquid crystal compositions G to I, K to N, P and Q showed an improved low-temperature operation characteristic, a high-speed responsiveness, and a decreased temperature dependence of the response speed.

EXAMPLE 23

A blank cell was prepared in the same manner as in Example 16 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition I prepared in Example 16. The liquid crystal device was subjected to measurement of optical response time in the same manner as in Example 12. The results are shown below.

|                      | 10° C. | 25° C. | 40° C. |
|----------------------|--------|--------|--------|
| Response time (μsec) | 667    | 318    | 171    |

EXAMPLE 24

A blank cell was prepared in the same manner as in Example 16 except for omitting the $SiO_2$ layer to form an alignment control layer composed of the polyimide resin layer alone on each electrode plate. A ferroelectric liquid crystal device was prepared by filling the blank cell with the liquid crystal composition I prepared in Example 16. The liquid crystal device was subjected to measurement of optical response time in the same manner as in Example 12. The results are shown below.

|                      | 10° C. | 25° C. | 40° C. |
|----------------------|--------|--------|--------|
| Response time (μsec) | 660    | 321    | 173    |

As is apparent from the above Examples 23 and 24, also in the cases of different device structures, the devices containing the ferroelectric liquid crystal composition I according to the present invention respectively provided a remarkably improved operation characteristic at a lower temperature and also a decreased temperature-dependence of the response speed similar to those in Example 16.

EXAMPLE 25

2-(4-hexylphenyl)-5-(4-hexanoyloxyphenyl)thiazole (Example Compound No. 1-196) was synthesized through the following reaction scheme.

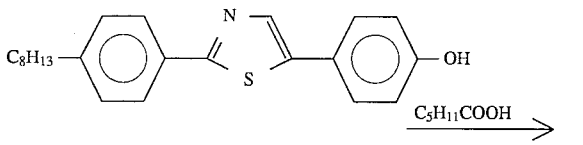

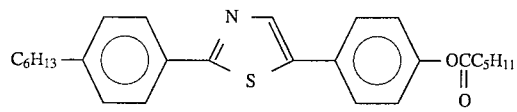

In a 200 ml-round-bottomed flask, 2.00 g (5.93 mM) of 2-(4-hexylphenyl)-5-(4-hydroxyphenyl)thiazole, 0.76 g (6.54 mM) of hexanoic acid and 40 ml of dichloromethane were placed and mixed. To the solution, 1.24 g (6.01 mM) of N,N'-dicyclohexylcarbodiimide and 0.10 g of 4-pyrrolidinopyridine were successively added under stirring at room temperature, followed by further stirring for 7 hours at room temperature to precipitate N,N'-dicyclohexylurea. The resultant N,N'-dicyclohexylurea was filtered off and the solvent of the filtrate was distilled-off under reduced pressure. The residue was purified by silica gel column chromatography (eluent: toluene/ethyl acetate=100/1) and recrystallized from a mixture solvent of toluene-methanol to obtain 1.81 g of 2-(4-hexylphenyl)-5-(4-hexanoyloxyphenyl)thiazole (Yield: 70.1%).

Phase transition temperature (°C.)

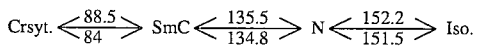

EXAMPLE 26

2-(4-hexylphenyl)-5-[4-(4-methylpentanoyloxy)phenyl]thiazole (Example Compound No. 1-197) was prepared in the same manner as in Example 25 (Yield: 82.1%).

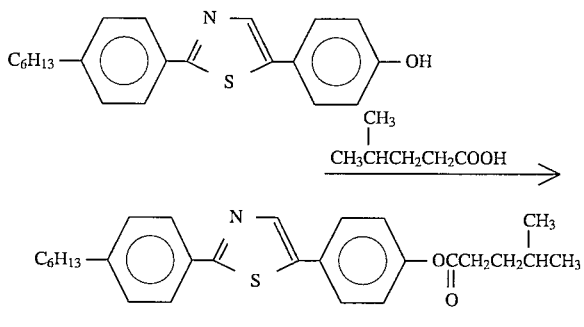

Phase transition temperature (°C.)

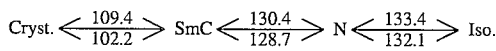

EXAMPLE 27

2-(4-butylphenyl)-5-(4-heptanoyloxyphenyl)thiazole (Example Compound No. 1-48) was prepared in the same manner as in Example 25 by using 2-(4-butylphenyl)-5-(4-hydroxyphenyl)thiazole prepared in the same manner as in Example 1 (Yield: 85.7%).

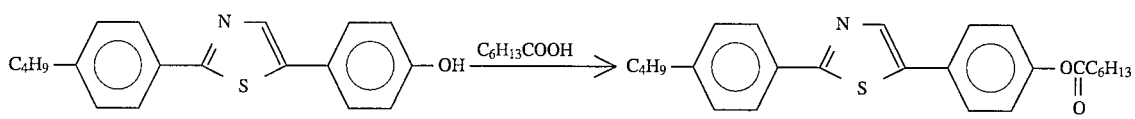

-continued

Phase transition temperature (°C.)

Cryst. $\underset{20.5}{\overset{70.9}{\rightleftarrows}}$ Sm3 $\underset{72.4}{\overset{75.6}{\rightleftarrows}}$ SmC $\underset{128.7}{\overset{129.5}{\rightleftarrows}}$ N $\underset{147.5}{\overset{148.3}{\rightleftarrows}}$ Iso.

EXAMPLE 28

2-(4-butylphenyl)-5-(4-pentanoyloxyphenyl)thiazole (Example Compound No. 1-198) was prepared in the same manner as in Example 27 (Yield: 76.2%).

-continued

Phase transition temperature (°C.)

Cryst. $\underset{97.6}{\overset{100.9}{\rightleftarrows}}$ SmC $\underset{117.0}{\overset{117.8}{\rightleftarrows}}$ N $\underset{150.0}{\overset{150.7}{\rightleftarrows}}$ Iso.

EXAMPLE 29

2-(4-hexylphenyl)-5-(3-fluoro-4-heptanoyloxyphenyl)thiazole (Example Compound No. 1-192) was synthesized through the following reactions schemes in the same manner as in Example 1 with the yields of respective steps shown below.

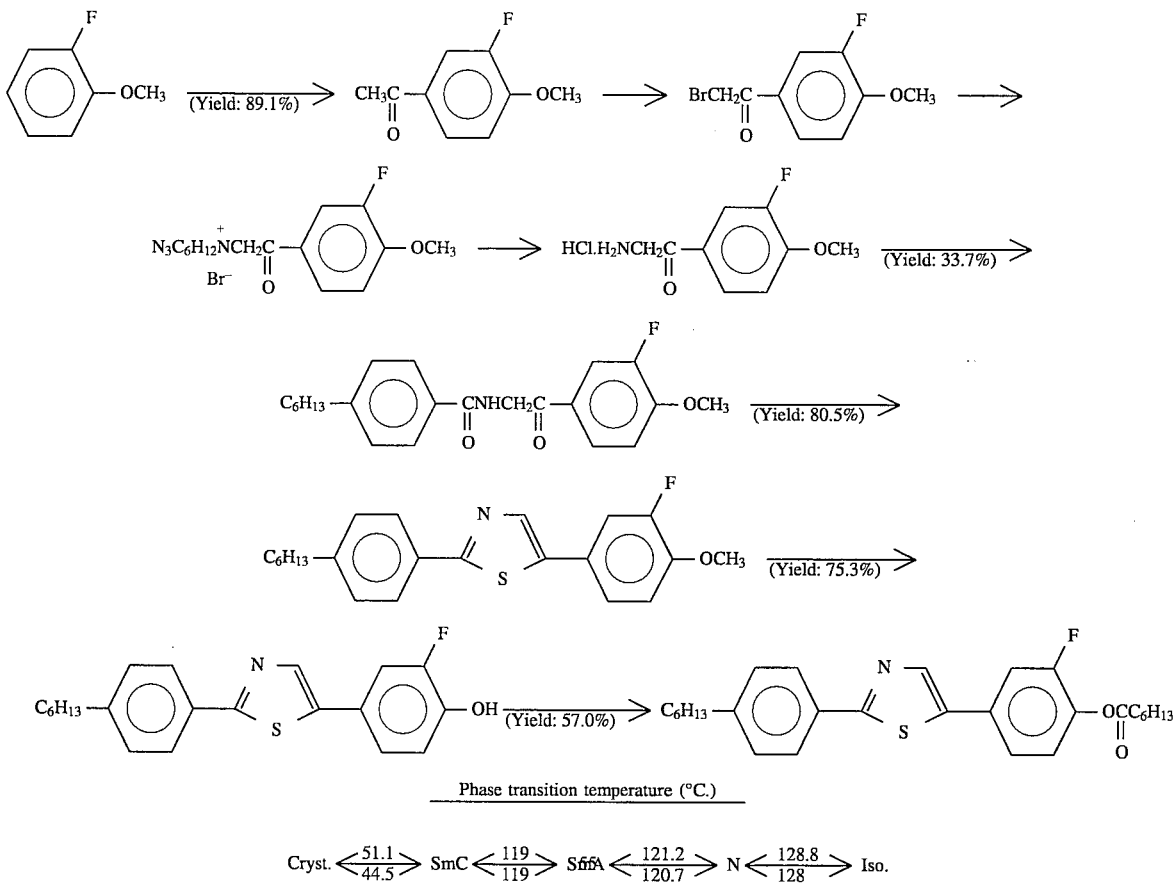

Phase transition temperature (°C.)

Cryst. $\underset{44.5}{\overset{51.1}{\rightleftarrows}}$ SmC $\underset{119}{\overset{119}{\rightleftarrows}}$ SmA $\underset{120.7}{\overset{121.2}{\rightleftarrows}}$ N $\underset{128}{\overset{128.8}{\rightleftarrows}}$ Iso.

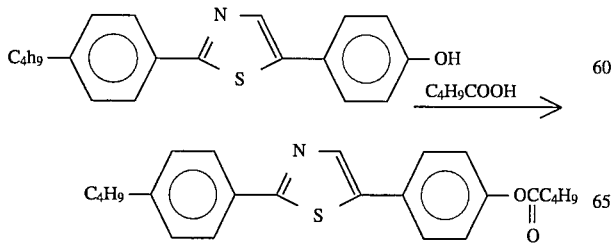

EXAMPLE 30

2-decyl-5-(3-fluoro-4-heptanoyloxyphenyl)thiazole (Example Compound No. 1-200) was synthesized through the following reaction schemes in the same manner as in Example 6 by using 3-fluoro-4-methoxyphenacylamine hydrochloride prepared in Example 29 with the yields of respective steps shown below.

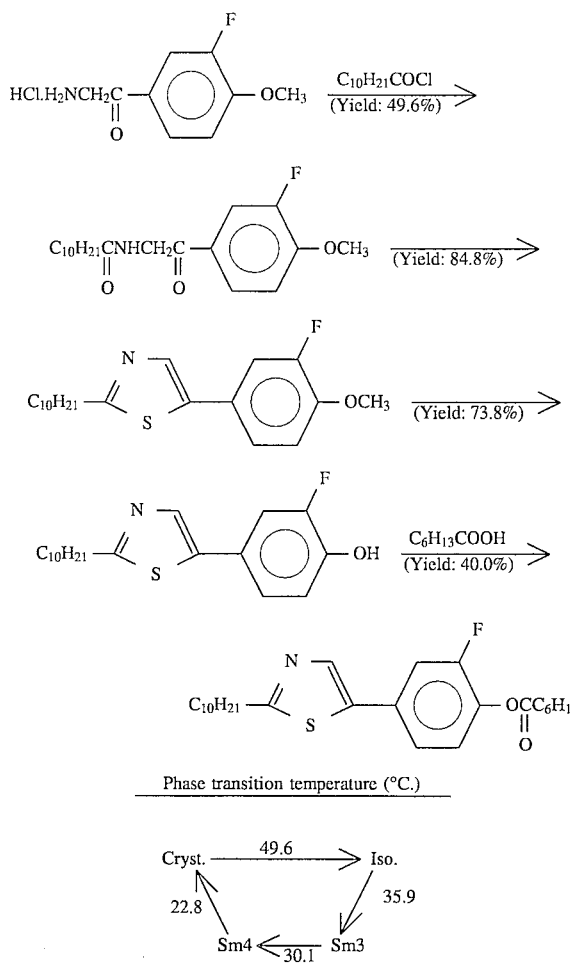

Phase transition temperature (°C.)

Cryst. —49.6→ Iso.
    ↖22.8      ↙35.9
       Sm4 ⇄30.1 Sm3

EXAMPLE 31

2-(4-hexylphenyl)-5-(3-fluoro-4-hexyloxyphenyl)thiazole (Example Compound No. 1-199) was synthesized through the following reaction scheme.

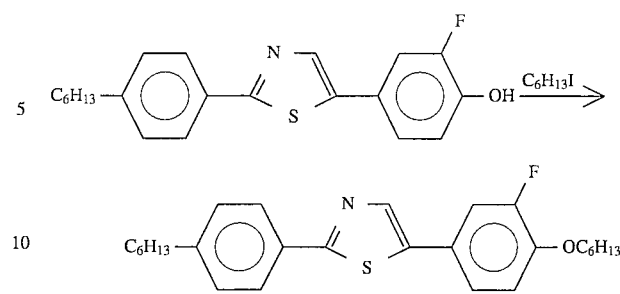

In a 30 ml-round-bottomed flask, 1.07 g (3.01 mM) of 2-(4-hexylphenyl)-5-(3-fluoro-4-hydroxyphenyl)thiazole prepared in Example 29, 0.23 g (3.48 mM) of potassium hydroxide and 5 ml of butanol were placed and heated. To the solution, 0.74 g (3.49 mM) of hexyl iodide was gradually added under heat-stirring, followed by heat-stirring for 5 hours about 90° C. After the reaction, the solvent was removed from the reaction mixture and water was added to the resultant residue to precipitate a crystal. The crystal was recovered by filtration and washed with water. The resultant crystal was purified by silica gel column chromatography (eluent: toluene) and recrystallized from a mixture solvent of toluene-methanol to obtain 0.90 g of 2-(4-hexylphenyl)-5-(3-fluoro-4-hexyloxyphenyl)thiazole (Yield: 68.0%).

Phase transition temperature (°C.)

Cryst. ⇄$_{14.3}^{23}$ Sm4 ⇄$_{48.3}^{54.2}$ Sm3 ⇄$_{80.9}^{95.5}$ SmC ⇄$_{116}^{116}$ SmA ⇄$_{124.5}^{124.4}$ N ⇄$_{129.6}^{129.7}$ Iso

EXAMPLE 32

2-(4-butylphenyl)-5-(4-nonanoyloxyphenyl)thiazole (Example Compound No. 1-49) was prepared in the same manner as in Example 27 (Yield: 57.5%).

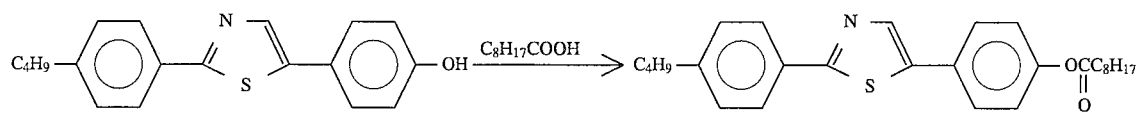

-continued
Phase transition temperature (°C.)

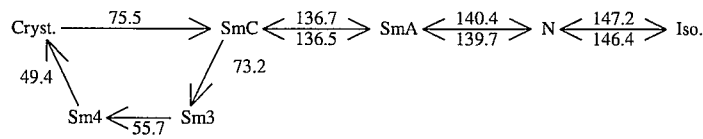

EXAMPLE 33

2-(4-hexylphenyl)-5-(2-fluoro-4-heptanoyloxyphenyl)thiazole (Example Compound No. 1-217) was prepared in the same manner as in Example 25 by using 2-(4-hexylphenyl)-5-(2-fluoro-4-hydroxyphenyl)thiazole prepared from m-fluoroanisole in the same manner as in Example 29 (Yield: 63.3%).

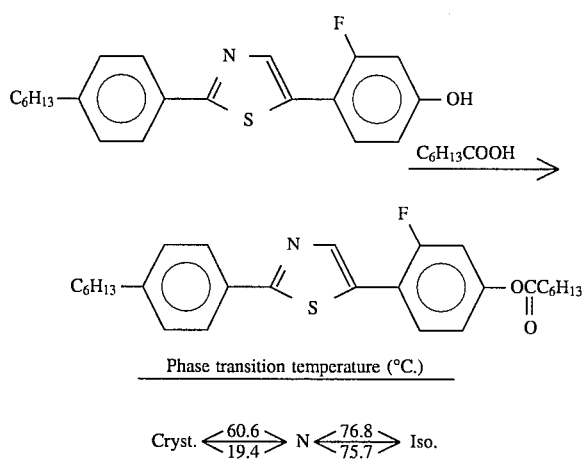

Phase transition temperature (°C.)

EXAMPLE 34

2-(4-hexylphenyl)-5-(2-fluoro-4-hexyloxyphenyl)thiazole (Example Compound No. 1-220) was prepared in the same manner as in Example 31 by using 2-(4-hexylphenyl)-5-(2-fluoro-4-hydroxyphenyl)thiazole prepared in Example 33 (Yield: 79.6%).

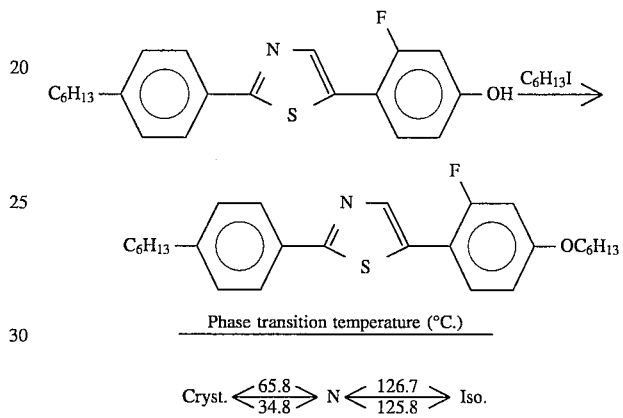

Phase transition temperature (°C.)

EXAMPLE 35–40

Six species of mesomorphic compounds shown in Table 1 were prepared in the same manner as in Example 8. The results are shown in Table 1 below.

TABLE 1

Production of R—⟨phenyl⟩—C(=N)—S—⟨phenyl⟩—R'

| Ex. No. | Ex. Comp. No. | R | R' | Phase transition temperature (°C.) |
|---|---|---|---|---|
| 35 | 1-2 | $C_4H_9$ | $C_8H_{17}$ | Cryst. →64.7→ SmA ⇌119.1/117.6⇌ Iso.; 54.6, 60.6, Sm3 |
| 36 | 1-201 | $C_4H_9$ | $C_9H_{19}$ | Cryst. →72.2→ SmA ⇌123.5/121.9⇌ Iso.; 56.3, 67.4, Sm3 |
| 37 | 1-8 | $C_6H_{13}$ | $C_4H_9$ | Cryst. ⇌71.9/48.1⇌ SmA ⇌94.9/93.9⇌ N ⇌118.1/117.1⇌ Iso. |
| 38 | 1-208 | $C_8H_{17}$ | $C_6H_{13}$ | Cryst. →46.8→ SmA ⇌123.6/122.4⇌ Iso.; 43.6, 59.9, SmC |

TABLE 1-continued

Production of R—⌬—(N=/S)—⌬—R'

| Ex. No. | Ex. Comp. No. | R | R' | Phase transition temperature (°C.) |
|---|---|---|---|---|
| 39 | 1-19 | $C_8H_{17}$ | $C_8H_{17}$ | Cryst. $\underset{55.7}{\overset{61.6}{\rightleftarrows}}$ SmC $\underset{64.7}{\overset{65.8}{\rightleftarrows}}$ SmA $\underset{124.6}{\overset{126.8}{\rightleftarrows}}$ Iso. |
| 40 | 1-210 | $C_8H_{17}$ | $C_{10}H_{21}$ | Cryst. $\underset{41.1}{\overset{45.4}{\rightleftarrows}}$ Sm4 $\underset{58.3}{\overset{65.3}{\rightleftarrows}}$ Sm3 $\underset{76.2}{\overset{77.1}{\rightleftarrows}}$ SmC $\underset{95}{\overset{95}{\rightleftarrows}}$ SmA $\underset{125.1}{\overset{126.6}{\rightleftarrows}}$ Iso. |

EXAMPLE 41

2-hexyl-5-(6-undecanoyloxy-2-naphthyl)thiazole (Example Compound No. 1-222) was synthesized through the following reaction schemes in the same manner as in Example 25 by using 2-hexyl-5-(6-hydroxy-2-naphthyl)thiazole prepared from 2-acetyl-6-methoxynaphthalene synthesized through a process shown in "Org., Syn. Coll.", vol. 6, 34.

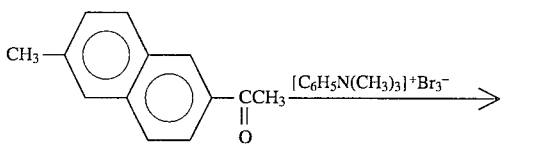

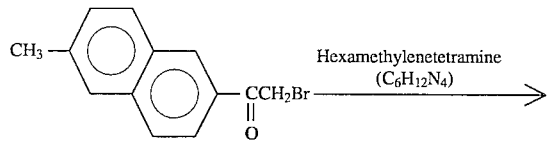

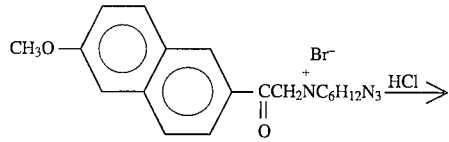

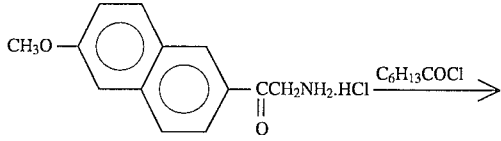

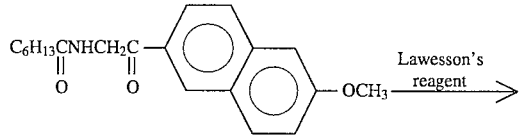

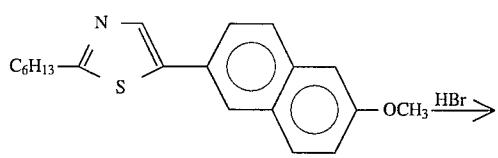

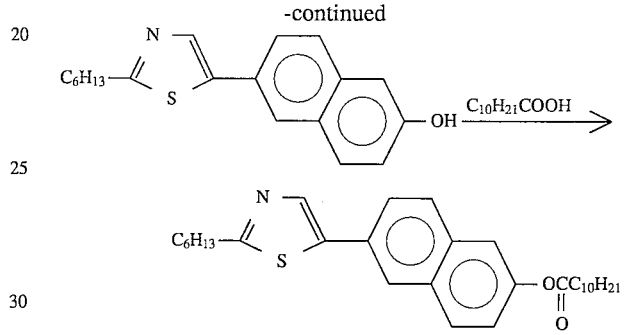

Phase transition temperature (°C.)

Cryst. $\underset{74.7}{\overset{92.2}{\rightleftarrows}}$ SmA $\underset{112.1}{\overset{113.5}{\rightleftarrows}}$ Iso.

EXAMPLE 42

2-hexyl-5-(6-decyloxy-2-naphthyl)thiazole (Example Compound No. 1-223) was prepared in the same manner as in Example 31 by using 2-hexyl-5-(6-hydroxy-2-naphthyl)thiazole prepared in Example 41 (Yield: 52.9%).

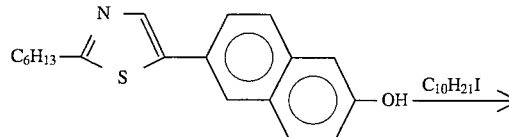

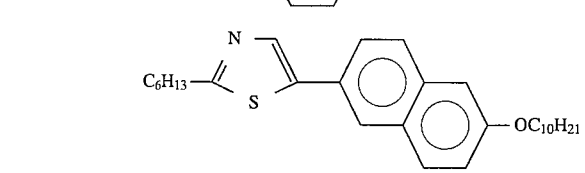

Phase transition temperature (°C.)

Cryst. $\underset{88.8}{\overset{105.4}{\rightleftarrows}}$ SmA $\underset{106.5}{\overset{108.0}{\rightleftarrows}}$ Iso.

EXAMPLE 43

2-(4-heptanoyloxyphenyl)-5-(4-hexylphenyl)thiazole (Example Compound No. 1-95) was synthesized through the following steps i)–iv).

Step i)

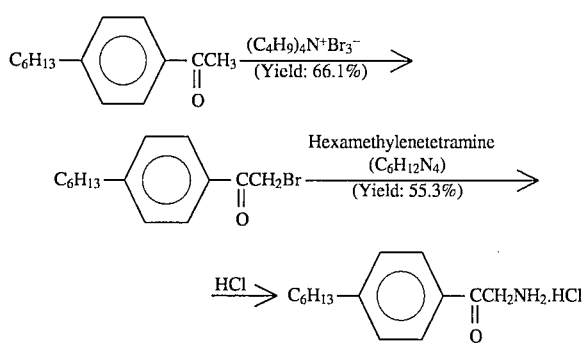

4-hexylphenacrylamine hydrochloride was synthesized through the above reaction scheme in the same manner as in Example 1.

Step ii)

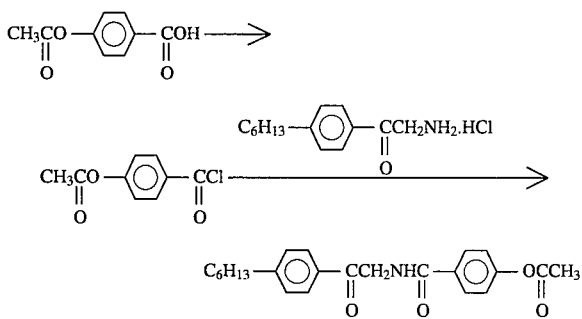

In a 200 ml-reaction vessel, 21.4 g ($1.18 \times 10^{-1}$M) of p-acetoxybenzoic acid and 80 ml of dry benzene were placed. To the mixture, 25.0 g ($1.20 \times 10^{-1}$M) of phosphorus pentachloride was added in 10 minutes at room temperature, followed by stirring for 3 hours at 50° C. After cooling, the solvent of the reaction mixture was distilled off to provide oily p-acetoxybenzoyl chloride.

Then, in a 300 ml-reaction vessel, 30 g ($1.17 \times 10^{-1}$ mol) of 4-hexylphenacylamine hydrochloride and 200 ml of dry pyridine were placed. To the mixture, a solution of the above-prepared p-acetoxybenzoyl chloride in 20 ml of dry benzene was added dropwise in 50 minutes below 0° C., followed by stirring for 5 hours while gradually cooling to room temperature. After the reaction, the reaction mixture was poured into ice water to precipitate a crystal. The crystal was recovered by filtration, dried and purified by silica gel column chromatography (eluent: n-hexane/ethyl acetate=2/1) to obtain 21.5 g of 4'-acetoxybenzoyl-4-hexylphenacylamine (Yield: 48.2%).

Step iii)

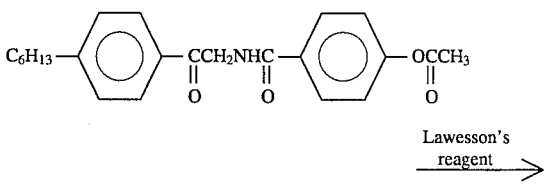

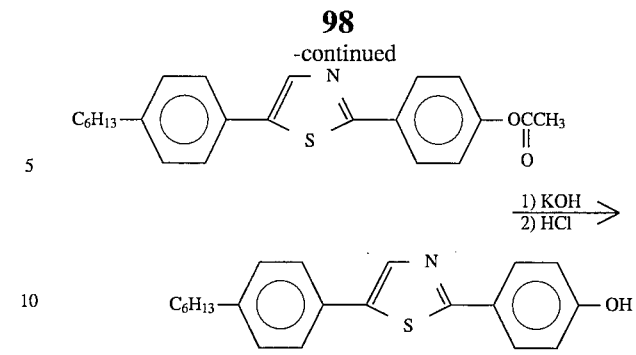

In a 200 ml-reaction vessel, 20.0 g ($5.25 \times 10^{-2}$M) of 4'-acetoxybenzoyl-4-hexylphenacylamine, 21.2 g ($5.25 \times 10^{-2}$M) of Lawesson's reagent and 100 ml of toluene were placed, followed by heat-refluxing for 3 hours. After cooling, the reaction mixture was subjected to distilling-off of the solvent to provide a residue. The residue was purified by silica gel column chromatography (eluent: n-hexane/ethyl acetate=6/1) to obtain 16.5 g of 2-(4-acetoxyphenyl)-5-(4-hexylphenyl)thiazole (Yield: 82.9%).

Then, in a 500 ml-reaction vessel, 16.5 g ($4.35 \times 10^{-2}$M) of 2-(4-acetoxyphenyl)-5-(4-hexylphenyl)thiazole and 250 ml of 0.5N-solution of potassium hydroxide in ethanol, followed by stirring for 3 hours at 60° C. After cooling, the reaction mixture was poured into 600 ml of ice water and acidified with 6N-hydrochloric acid to precipitate a crystal. The crystal was recovered by filtration, washed with water and dissolved in ethanol, followed by treatment with activated carbon. The activated carbon was removed from the above mixture by filtration and the filtrate was condensed, followed by drying to provide a residue. The residue was recrystallized from ethanol to obtain 12.8 g of 2-(4-hydroxyphenyl)-5-(4-hexylphenyl)thiazole (Yield: 87.3%).

Step iv)

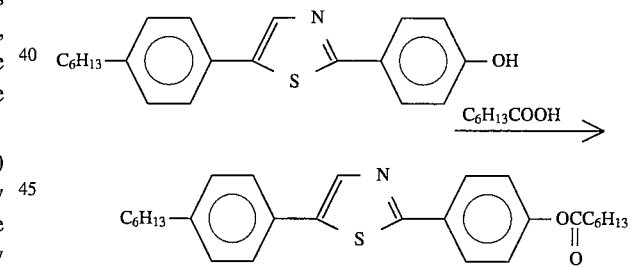

2-(4-heptanoyloxyphenyl)-5-(4-hexylphenyl)thiazole was prepared from 2-(4-hydroxyphenyl)-5-(4-hexylphenyl)thiazole in the same manner as in Example 25 (Yield: 45.1%).

Phase transition temperature (°C.)

Cryst. $\underset{87.8}{\overset{93.2}{<}}$ SmC $\underset{129.0}{\overset{129.8}{<}}$ N $\underset{146.0}{\overset{146.8}{<}}$ Iso.

EXAMPLE 44

2-(4-hexyloxyphenyl)-5-(4-hexylphenyl)thiazole (Example Compound No. 1-78) was prepared in the same manner as in Example 31 by using 2-(4-hydroxyphenyl)-5-(4-hexylphenyl)thiazole prepared in Example 43 (Yield: 80.0%).

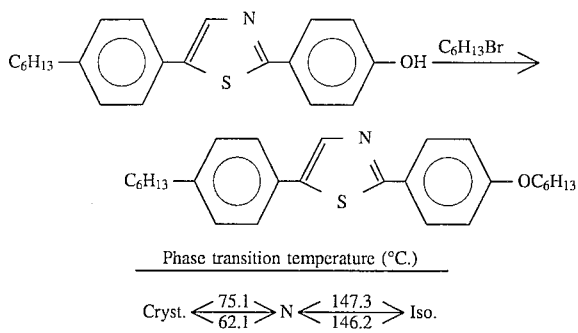
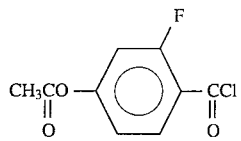

Phase transition temperature (°C.)

Cryst. $\underset{62.1}{\overset{75.1}{\lessgtr}}$ N $\underset{146.2}{\overset{147.3}{\lessgtr}}$ Iso.

EXAMPLE 45

2-(2-fluoro-4-heptanoyloxyphenyl)-5-(4-hexylphenyl)thiazole (Example Compound No. 1-225) was synthesized through the following steps i)–iii).

Step i)

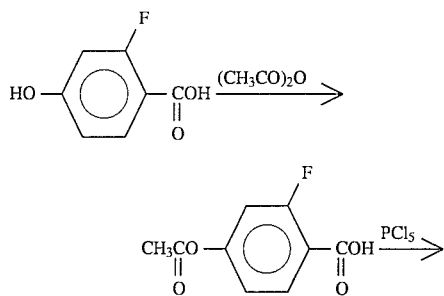

-continued

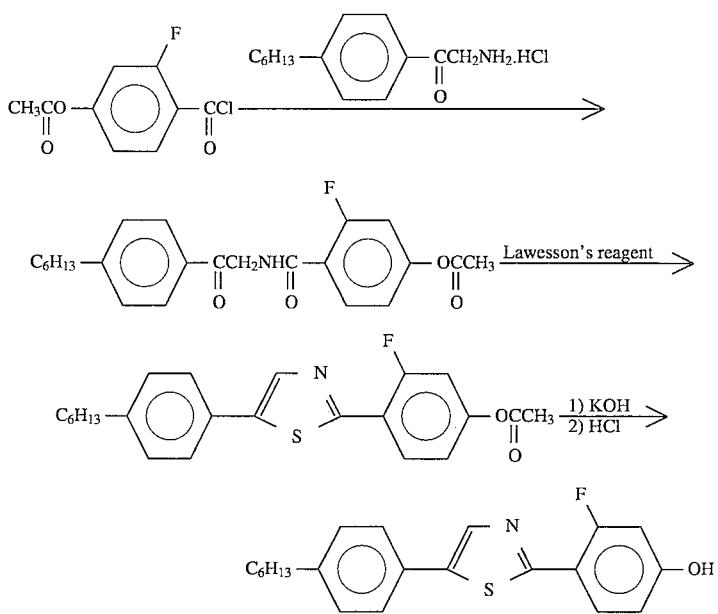

In a 100 ml-reaction vessel, 12.1 g ($1.83 \times 10^{-1}$M) of potassium hydroxide and 50 ml of water were placed, followed by cooling to 0° C. To the mixture, 12.0 g ($7.69 \times 10^{-2}$M) of 2-fluoro-4-hydroxybenzoic acid was added and dissolved therein. To the solution, 7.9 g ($7.74 \times 10^{-2}$M) of acetic anhydride was added dropwise in 30 minutes at 0° C., followed by stirring for 2 hours. After stirring, the reaction mixture was acidified with 6N-hydrochloric acid to precipitate a crystal. The crystal was recovered by filtration, followed by washing with water and drying to obtain 9.5 g of 2-fluoro-4-acetoxybenzoic acid (Yield: 62.4%).

Then, in a 100 ml-reaction vessel, 9.5 g ($4.80 \times 10^{-2}$M) of 2-fluoro-4-acetoxybenzoic acid and 50 ml of dry benzene were placed. To the mixture, 10.3 g ($4.94 \times 10^{-2}$M) of phosphorus pentachloride was added in 30 minutes at room temperature, followed by stirring for 4 hours at 50° C. After cooling, the solvent of the reaction mixture was distilled off to provide oily 2-fluoro-4-acetoxy-benzoyl chloride.

Step ii)

In a 200 ml-reaction vessel, 12.3 g ($4.81 \times 10^{-2}$ mol) of 4-hexylphenacylamine hydrochloride prepared in Example 43 and 95 ml of dry pyridine were placed. To the mixture, a solution of the above-prepared 2-fluoro-4-acetoxybenzoyl chloride in 20 ml of dry benzene was added dropwise in 60 minutes below 0° C., followed by stirring for 15 hours while gradually cooling to room temperature. After the reaction, the reaction mixture was poured into ice water to precipitate a crystal. The crystal was recovered by filtration, dried and purified by silica gel column chromatography (eluent: n-hexane/ethyl acetate=2/1) to obtain 9.3 g of 2'-fluoro-4'-acetoxybenzoyl-4-hexylphenacylamine (Yield: 48.7%).

Then, in a 100 ml-reaction vessel, 9.20 g ($2.31 \times 10^{-2}$M) of 2'-fluoro-4'-acetoxybenzoyl-4-hexylphenacylamine, 9.32 g ($2.31 \times 10^{-2}$M) of Lawesson's reagent and 50 ml of toluene were placed, followed by heat-refluxing for 1 hours. After cooling, the reaction mixture was subjected to distilling-off of the solvent to provide a residue. The residue was purified by silica gel column chromatography (eluent: n-hexane/ethyl acetate=6/1) to obtain 8.39 g of 2-(2-fluoro-4-acetoxyphenyl)-5-(4-hexylphenyl)thiazole (Yield: 91.3%).

Then, in a 200 ml-reaction vessel, 8.2 g ($2.07 \times 10^{-2}$M) of 2-(4-acetoxyphenyl)-5-(4-hexylphenyl)thiazole and 130 ml of 0.5N-solution of potassium hydroxide in ethanol, followed by stirring for 3 hours at 60° C. After cooling, the reaction mixture was poured into 300 ml of ice water and acidified with 6N-hydrochloric acid to precipitate a crystal. The crystal was recovered by filtration, washed with water and dissolved in ethanol, followed by treatment with activated carbon. The activated carbon was removed from the above mixture by filtration and the filtrate was condensed, followed by drying to provide a residue. The residue was recrystallized from ethanol to obtain 6.5 g of 2-(2-fluoro-4-hydroxyphenyl)-5-(4-hexylphenyl)thiazole (Yield: 88.4%).

Step iii)

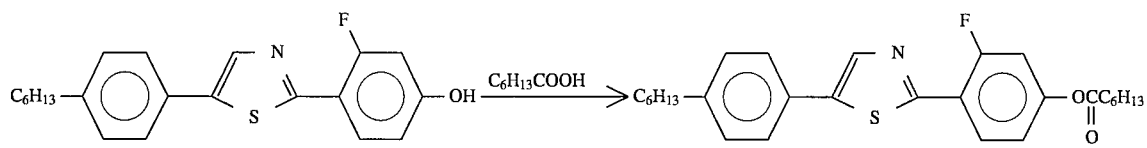

2-(2-fluoro-4-heptanoyloxyphenyl)-5-(4-hexylphenyl)thiazole was prepared in the same manner as in Example 25 (Yield: 78.7%).

Phase transition temperature (°C.)

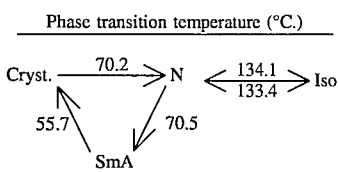

EXAMPLE 46

2-(2-fluoro-4-hexyloxyphenyl)-5-(4-hexylphenyl)thiazole (Example Compound No. 1-227) was prepared in the same manner as in Example 31 by using 2-(2-fluoro-4-hydroxyphenyl)-5-(4-hexylphenyl)thiazole prepared in Example 45 (Yield: 38.2%).

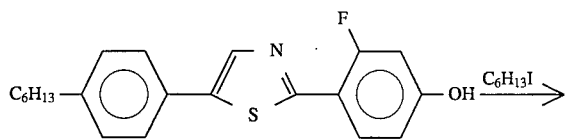

Phase transition temperature (°C.)

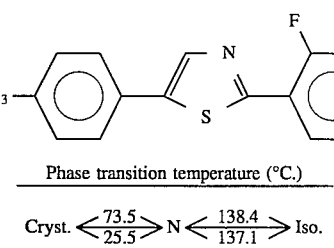

EXAMPLE 47

2-(6-hexyloxy-2-naphthyl)-5-(4-hexylphenyl)thiazole (Example Compound No. 1-229) was synthesized through the following steps i)–iii).

Step i)

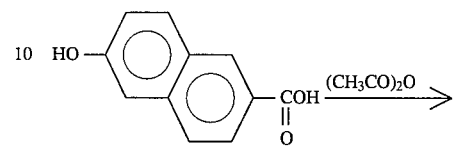

-continued

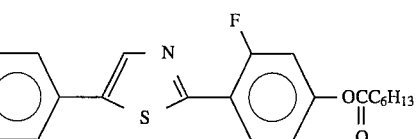

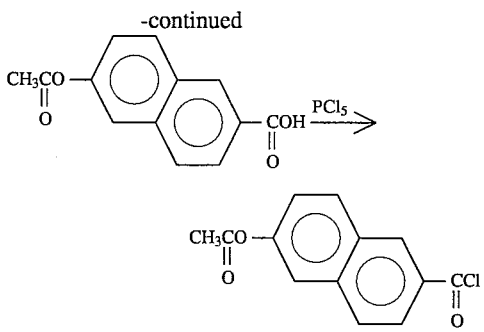

In a 100 ml-reaction vessel, 16.7 g ($2.53 \times 10^{-1}$M) of potassium hydroxide and 85 ml of water were placed, followed by cooling to 0° C. To the mixture, 20.0 g ($1.06 \times 10^{-1}$M) of 6-hydroxy-2-naphthoic acid was added and dissolved therein. To the solution, 10.9 g ($1.07 \times 10^{-1}$M) of acetic anhydride was added dropwise in 40 minutes at 0° C. followed by stirring for 2 hours. After stirring, the reaction mixture was acidified with 6N-hydrochloric acid to precipitate a crystal. The crystal was recovered by filtration, followed by washing with water and drying to obtain 18.3 g of 6-acetoxy-2-naphthoic acid (Yield: 74.4%).

Then, in a 200 ml-reaction vessel, 17.1 g ($7.43 \times 10^{-2}$M) of 6-acetoxy-2-naphthoic acid and 85 ml of dry benzene were placed. To the mixture, 15.9 g ($6.91 \times 10^{-2}$M) of phosphorus pentachloride was added in 30 minutes at room temperature, followed by stirring for 4 hours at 60° C. After cooling, the solvent of the reaction mixture was distilled off to provide oily 6-acetoxy-2-naphthoyl chloride.

Step ii)

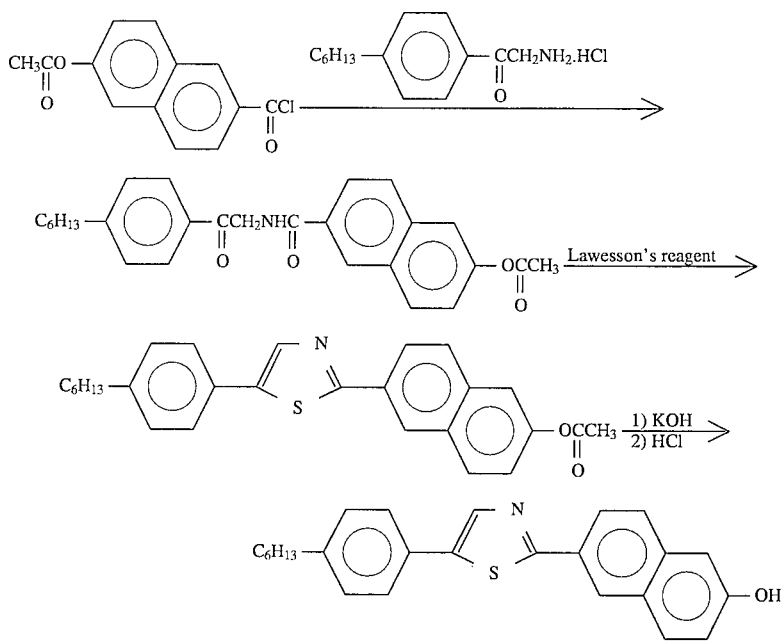

In a 300 ml-reaction vessel, 19.0 g (7.44×10⁻² mol) of 4-hexylphenacylamine hydrochloride prepared in Example 43 and 95 ml of dry pyridine were placed. To the mixture, a solution of the above-prepared 6-acetoxy-2-naphthoyl chloride in 50 ml of dry benzene was added dropwise in 35 minutes below 0° C., followed by stirring for 17 hours while gradually cooling to room temperature. After the reaction, the reaction mixture was poured into ice water, followed by extraction with chloroform. The organic layer was washed with water and dried with anhydrous sodium sulfate, followed by distilling-off of the solvent. The residue was purified by silica gel column chromatography (eluent: chloroform/ethyl acetate=25/1) to obtain 14.0 g of 6'-acetoxy-2'-naphthoyl-4-hexylphenacylamine (Yield: 43.7%).

Then, in a 200 ml-reaction vessel, 13.7 g (3.18×10⁻²M) of 6'-acetoxy-2'-naphthoyl-4-hexylphenacylamine, 12.9 g (3.18×10⁻²M) of Lawesson's reagent and 75 ml of toluene were placed, followed by heat-refluxing for 2 hours. After cooling, the reaction mixture was subjected to distilling-off of the solvent to provide a residue. The residue was purified by silica gel column chromatography (eluent: chloroform) to obtain 10.4 g of 2-(6-acetoxy-2-naphthyl)-5-(4-hexylphenyl)thiazole (Yield: 76.1%).

Then, in a 300 ml-reaction vessel, 10.4 g (2.42×10⁻²M) of 2-(6-acetoxy-2-naphthyl)-5-(4-hexylphenyl)-thiazole and 170 ml of 0.5N-solution of potassium hydroxide in ethanol, followed by stirring for 0.5 hour at 60° C. After cooling, the reaction mixture was poured into 400 ml of ice water and acidified with 6N-hydrochloric acid to precipitate a crystal. The crystal was recovered by filtration, washed with water and dissolved in ethanol, followed by treatment with activated carbon. The activated carbon was removed from the above mixture by filtration and the filtrate was condensed, followed by drying to provide a residue. The residue was recrystallized from ethanol to obtain 7.73 g of 2-(6-hydroxy-2-naphthyl)-5-(4-hexylphenyl)thiazole (Yield: 82.6%).

Step iii)

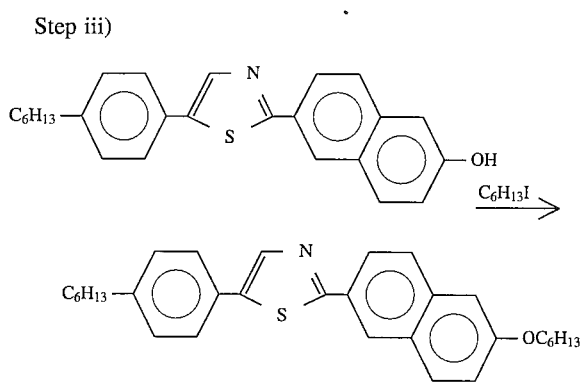

2-(6-hexyloxy-2-naphthyl)-5-(4-hexylphenyl)thiazole was prepared in the same manner as in Example 31 (Yield: 51.0%).

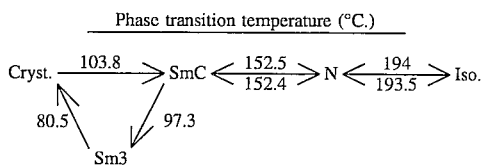

EXAMPLE 48

2-(6-decyloxy-2-naphthyl)-5-(4-hexylphenyl)thiazole (Example Compound No. 1-231) was prepared in the same manner as in Example 47 (Yield: 53.0%).

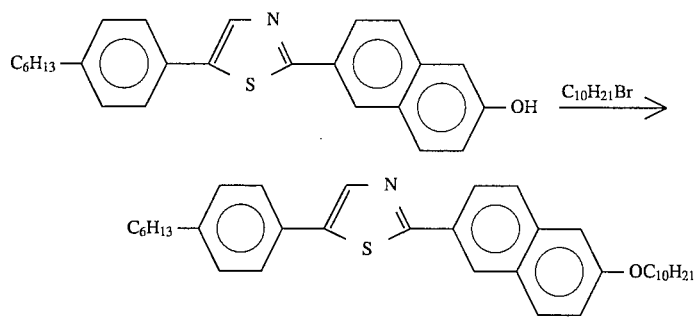

Phase transition temperature (°C.)

Cryst. ⇌82.7 SmC ⇌153.0/149.0 SmA ⇌169.3/168.8 N ⇌181.2/180.5 Iso.
       ↘59.3    ↙78.5
          Sm3

EXAMPLE 49

2-(6-decyloxy-2-naphthyl)-5-hexylthiazole (Example Compound No. 1-237) was synthesized through the following steps i) and ii).

Step i)

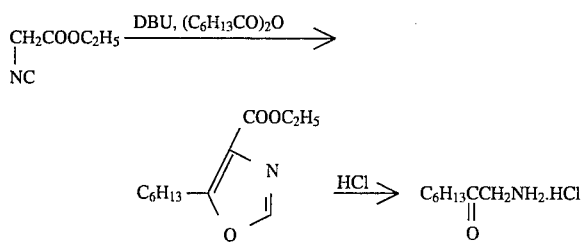

2-oxooctylamine hydrochloride was prepared in the following manner according to a method shown in "J. Org. Chem.", 38, 3571–3575 (1973).

In a 100 ml-three-necked flask, 2.26 g (20,0 mM) of ethylisocyanoacetate and 27 ml of tetrahydrofuran were placed. To the mixture, 2.99 ml (20.0 mM) of 1,8-diazobicyclo[5,4,0]-7-undecene (DBU) was added on an ice water bath under stirring. To the mixture, a solution of 4.84 g (20.0 mM) of heptanoic anhydride in 7 ml of tetrahydrofuran was added dropwise on the ice water bath under stirring, followed by stirring for 4.5 hours at room temperature. The reaction mixture was further left standing for 2 days at room temperature. The resultant reaction mixture was poured into water, followed by extraction with ethyl acetate. The organic layer was dried with anhydrous sodium sulfate and further dried under reduced pressure. The residue was purified by silica gel column chromatography (eluent: toluene/ethyl acetate=100/1) to provide 4.28 g of ethyl 5-hexyloxazole-4-carboxylate (Yield: 95.1%). Then, 2.10 g (9.32 mM) of ethyl 5-hexyloxazole-4-carboxylate and 28.4 ml of 6N-hydrochloric acid were placed in a 100 ml-round-bottomed flask, followed by heat-refluxing for 5 hours under stirring. After the reaction, the reaction mixture was washed two times with ethyl acetate. The water layer was dried under reduced pressure. The residue was recrystallized from a mixture solvent of methanol-isopropyl ether to obtain 0.67 g of 2-oxooctylamine hydrochloride (Yield: 40.0%).

Step ii)

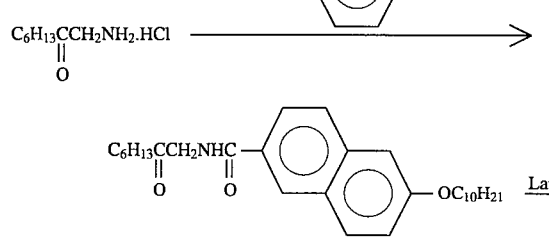

In a 50 ml-three-necked flask, 0.20 g (1.11 mM) of 2-oxooctylamine hydrochloride, 0.46 g (1.33 mM) of 6-decyloxy-2-naphthoyl chloride and 5 ml of dioxane were placed. To the mixture, 1.6 ml of pyridine was added at about 85° C. under heat-stirring, followed by heat-stirring for 30 minutes at 92°–94° C. After the reaction, the reaction mixture was poured into water to precipitate a crystal. The crystal was recovered by filtration and washed with water, followed by recrystallization from a mixture solvent of acetonemethanol to provide 0.41 g of 2-oxooctyl-(6-decyloxy-2-naphthoyl)amine (Yield: 81.2%).

Then, 0.40 g (0.88 mM) of 2-oxooctyl-(6-decyloxy-2-naphthoyl)amine, 0.38 g (0.94 mM) of Lawesson's reagent and 6 ml of tetrahydrofuran were placed in a 30 ml-round-bottomed flask, followed by heat-refluxing for 45 minutes under stirring. After the reaction, the reaction mixture was poured into a solution of 0.27 g of sodium hydroxide in 70 ml of ice water to precipitate a crystal. The crystal was recovered by filtration washed with water and dissolved in toluene, followed by drying with anhydrous sodium sulfate and distilling-off of the solvent under reduced pressure. The residue was purified by silica gel column chromatography (eluent: toluene/hexane=1/1) and recrystallized from a mixture solvent of acetonemethanol to obtain 0.21 g of 2-(6-decyloxy-2-naphthyl)-5-hexylthiazole (Yield: 52.7%).

Phase transition temperature (°C.)

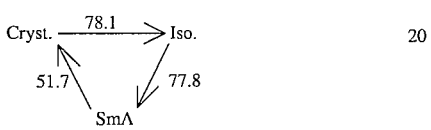

EXAMPLE 50

2-(4-nanonoyloxyphenyl)-5-octylthiazole (Example Compound No. 1-235) was synthesized through the following reaction schemes in the same manner as in Example 43 by using 2-oxodecylamine hydrochloride prepared in the same manner as in Example 49.

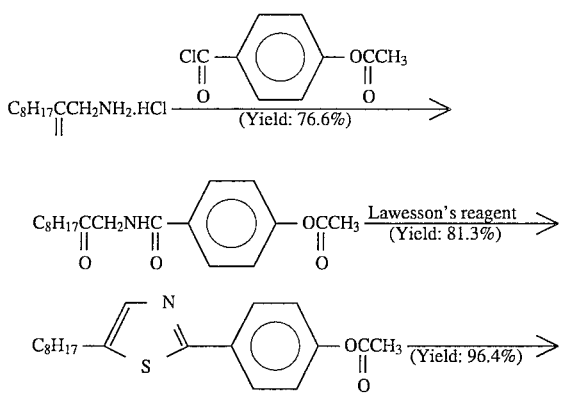

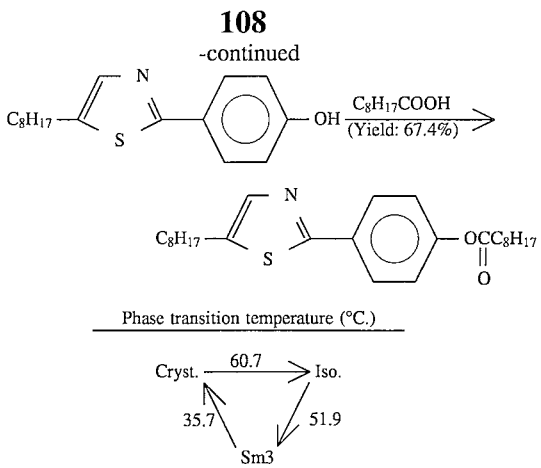

Phase transition temperature (°C.)

EXAMPLE 51

2-(4-hexylphenyl)-5-(trans-4-propylcyclohexyl)thiazole (Example Compound NO. 1-238) was synthesized through the following reaction schemes.

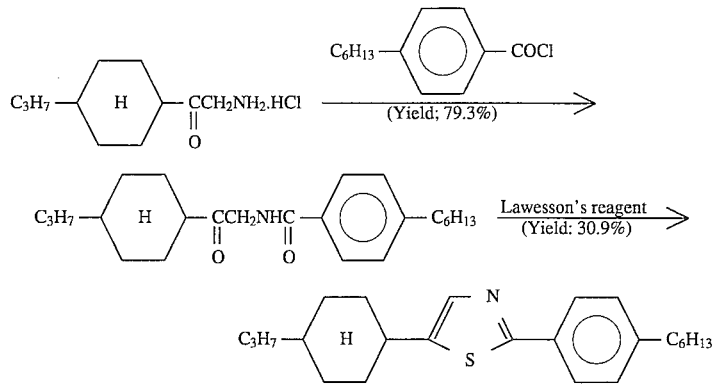

2-(trans-4-propylcyclohexyl)-2-oxoethylamine hydrochloride was prepared in the same manner as in Example 49 by using trans-4-propylcyclohexanecarboxylic anhydride prepared from trans-4-propylcyclohexanecarboxylic acid prepared in the same manner as in a method shown in "Org. Syn. Coll.", vol. 3, 28.

Then, 2-(4-hexylphenyl)-5-(trans-4-propylcyclohexyl)thiazole was prepared from 2-(trans-4-propylcyclohexyl)-2-oxoethylamine according to the above reaction schemes.

Phase transition temperature (°C.)

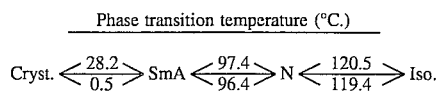

EXAMPLE 52

2-(4-octyloxyphenyl)-5-(trans-4-propylcyclohexyl)thiazole (Example Compound No. 1-240) was prepared in the same manner as in Example 51.

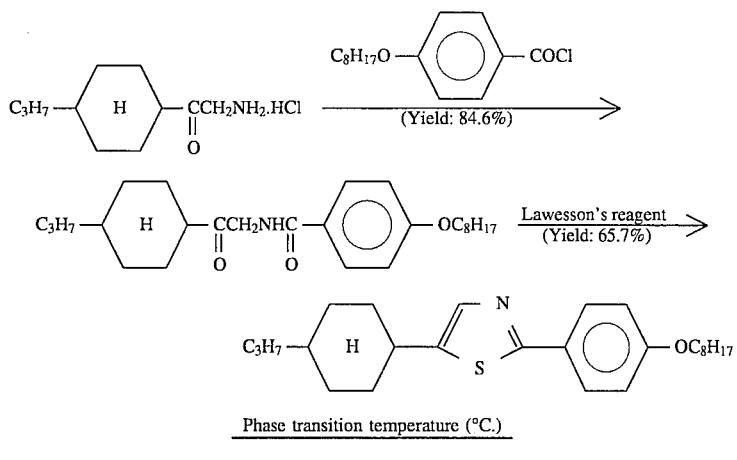

Phase transition temperature (°C.)

$$\text{Cryst.} \xleftarrow{\phantom{x}66.2\phantom{x}}_{45} \text{N} \xleftarrow{\phantom{x}141\phantom{x}}_{140.3} \text{Iso.}$$

EXAMPLE 53

A liquid crystal composition S was prepared by mixing the following example compounds in the indicated proportions with the liquid crystal composition F prepared in Example 14.

| Ex. Comp. No. | Structural formula | wt. parts |
|---|---|---|
| 1-12 | $C_6H_{13}$—〇—⟨N/S⟩—〇—$C_9H_{19}$ | 2 |
| 1-219 | $C_8H_{17}$—〇—⟨N/S⟩—〇(F)—$OCC_9H_{19}$(=O) | 3 |
| 1-236 | $C_{10}H_{21}CO(=O)$—〇—⟨N/S⟩—$C_8H_{17}$ | 2 |
| Composition F | | 93 |

A ferroelectric liquid crystal device was prepared in the same manner as in Example 12 except that the above liquid crystal composition S was used, and the device was subjected to measurement of optical response time. The results of the measurement are shown below.

|  | 10° C. | 25° C. | 40° C. |
|---|---|---|---|
| Response time (μsec) | 730 | 355 | 192 |

EXAMPLE 54

A liquid crystal composition T was prepared by mixing the following example compounds in the indicated proportions with the liquid crystal composition F prepared in Example 14.

| Ex. Comp. No. | Structural formula | wt. parts |
|---|---|---|
| 1-210 | $C_8H_{17}$—◯—(N/S)=—◯—$C_{10}H_{21}$ | 3 |
| 1-231 | $C_{10}H_{21}O$—◯◯—(N/S)=—◯—$C_6H_{13}$ | 3 |
| 1-247 | $C_4H_9$—◯(N)—(N/S)=—$C_8H_{17}$ | 2 |
| | Composition F | 92 |

A ferroelectric liquid crystal device was prepared in the same manner as in Example 12 except that the above liquid crystal composition T was used, and the device was subjected to measurement of optical response time. The results of the measurement are shown below.

| | 10° C. | 25° C. | 40° C. |
|---|---|---|---|
| Response time (μsec) | 712 | 343 | 188 |

EXAMPLE 55

A liquid crystal composition U was prepared by mixing the following example compounds in the indicated proportions with the liquid crystal composition O prepared in Example 21.

The results of the measurement are shown below.

| | 10° C. | 25° C. | 40° C. |
|---|---|---|---|
| Response time (μsec) | 633 | 329 | 180 |

EXAMPLE 56

A liquid crystal composition V was prepared by mixing the following example compounds in the indicated proportions with the liquid crystal composition O prepared in Example 21.

| Ex. Comp. No. | Structural formula | wt. parts |
|---|---|---|
| 1-227 | $C_6H_{13}O$—◯(F)—(N/S)=—◯—$C_6H_{13}$ | 2 |
| 1-237 | $C_{10}H_{21}O$—◯◯—(N/S)=—$C_6H_{13}$ | 3 |
| 1-239 | $C_8H_{17}$—◯—(N/S)=—◯(H)—$C_8H_{17}$ | 2 |
| | Composition O | 93 |

A ferroelectric liquid crystal device was prepared in the same manner as in Example 12 except that the above liquid crystal composition U was used, and the device was subjected to measurement of optical response time and observation of switching states. In the device, a monodomain with a good and uniform alignment characteristic was observed.

| Ex. Comp. No. | Structural formula | wt. parts |
|---|---|---|
| 1-215 | 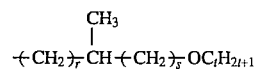 | 3 |
| 1-241 | 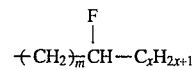 | 2 |
| 1-248 | 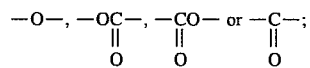 | 2 |
| | Composition O | 93 |

A ferroelectric liquid crystal device was prepared in the same manner as in Example 12 except that the above liquid crystal composition V was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 618 | 321 | 176 |

As is apparent from the results shown in the above Examples 53–56, the ferroelectric liquid crystal devices containing the liquid crystal compositions S, T, U and V showed an improved low-temperature operation characteristic, a high-speed responsiveness, and a decreased temperature dependence of the response speed.

As described hereinabove, according to the present invention, there are provided a mesomorphic compound, a liquid crystal composition containing the compound, and a liquid crystal device using the composition which shows a good switching characteristic, an improved low-temperature operation characteristic and a decreased temperature-dependence of response speed. According to the present invention, there is also provided a display apparatus utilizing the liquid crystal device of the present invention as a display unit, which shows good display characteristics in combination with a light source, a drive circuit, etc.

What is claimed is:

1. A mesomorphic compound represented by the following formula (I):

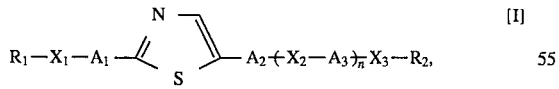 [I]

wherein $R_1$ and $R_2$ independently denote any one of the following groups (i)–(iv):

(i) an n-alkyl group having 4–14 carbon atoms;

(ii)

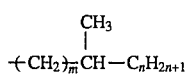

wherein m is an integer of 0–6 and n is an integer of 2–8;

(iii)

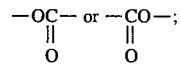

wherein r is an integer of 0–6, s is 0 or 1 and t is an integer of 1–12; and (iv)

$$\text{---}( \text{CH}_2 )_{\overline{m}}\text{CH}\text{---}\text{C}_x\text{H}_{2x+1}$$
$$|$$
$$F$$

wherein m is 0 or 1 and x is an integer of 1–14; $X_1$ and $X_3$ independently denote a single bond, $$-\text{O}-, -\underset{\underset{\text{O}}{\|}}{\text{OC}}-, -\underset{\underset{\text{O}}{\|}}{\text{CO}}- \text{ or } -\underset{\underset{\text{O}}{\|}}{\text{C}}-;$$

$X_2$ denotes a single bond, $$-\underset{\underset{\text{O}}{\|}}{\text{OC}}- \text{ or } -\underset{\underset{\text{O}}{\|}}{\text{CO}}-;$$

$A_1$ and $A_2$ independently denote a single bond,

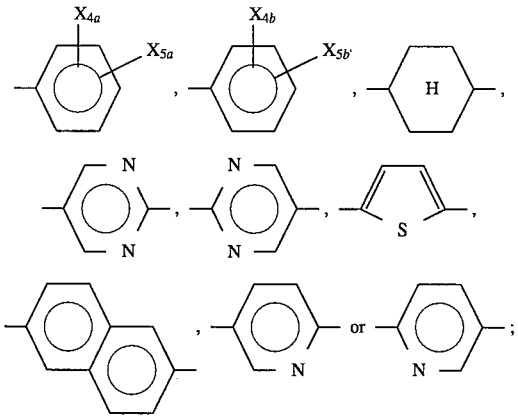

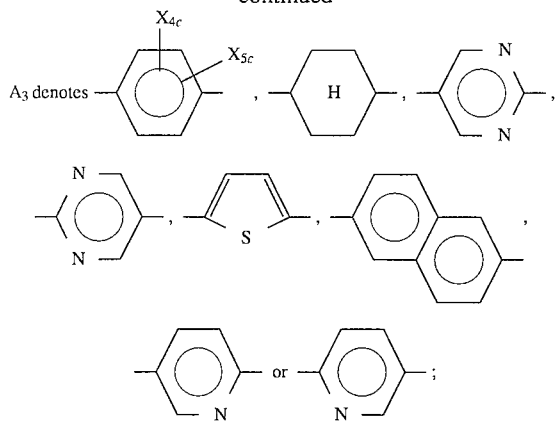

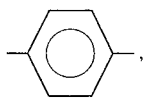

$X_{4a}$, $X_{5a}$, $X_{4b}$, $X_{5b}$, $X_{4c}$ and $X_{5c}$ independently denote hydrogen, fluorine, chlorine, bromine, —$CH_3$, —CN or —$CF_3$; and n is 0 or 1, with proviso that: $X_1$ always denotes a single bond when $A_1$ denotes a single bond, $X_3$ always denotes a single bond when $A_2$ denotes a single bond and n is 0; $A_1$ and $A_2$ cannot be single bonds simultaneously; $X_3$ cannot be —O— when $X_1$ denotes a single bond or —O—, $A_1$ denotes a single bond or

and —$A_2$—($X_2$—$A_3$—$)_n$ denotes

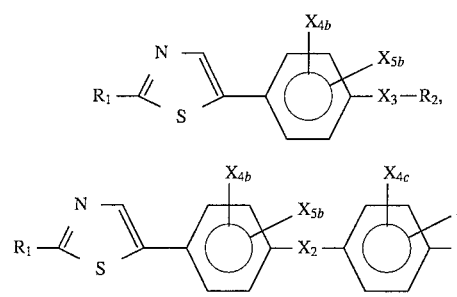

and $X_1$ cannot be a single bond when $A_1$ denotes and $A_2$ denotes a single bond and n is 0.

2. A mesomorphic compound according to claim 1, which is represented by any one of the following formulas (Ia)–(Iq):

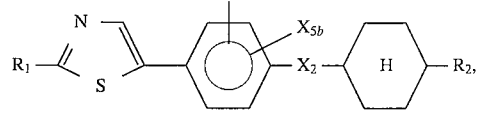 (Ia)

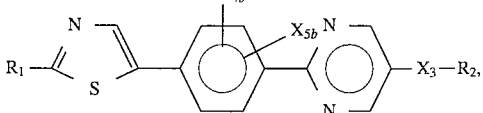 (Ib)

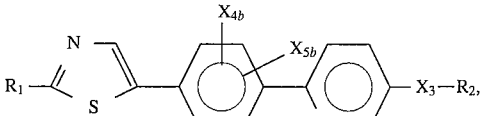 (Ic)

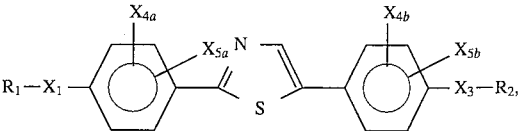 (Id)

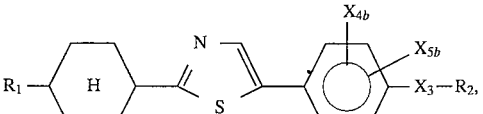 (Ie)

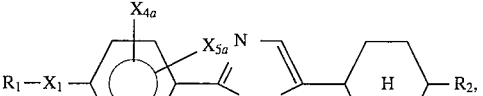 (If)

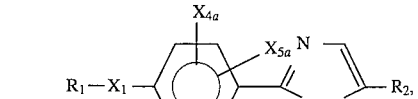 (Ig)

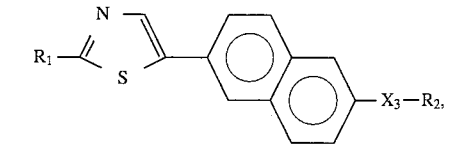 (Ih)

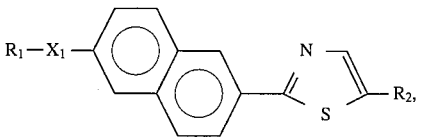 (Ii)

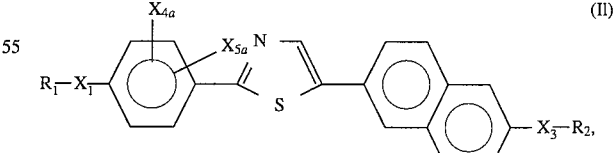 (Ij)

(Ik)

(Il)

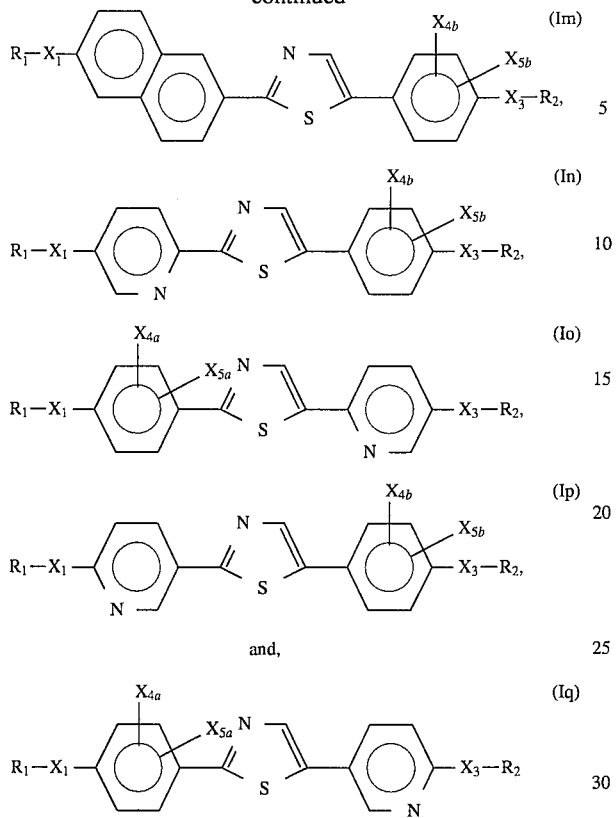

wherein $R_1$ and $R_2$ independently denote any one of the following groups (i)–(iv):

(i) an n-alkyl group having 4–14 carbon atoms;

(ii)

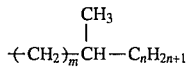

wherein m is an integer of 0–6 and n is an integer of 2–8;

(iii)

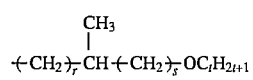

wherein r is an integer of 0–6, s is 0 or 1 and t is an integer of 1–12; and (iv)

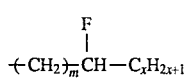

wherein m is 0 or 1 and x is an integer of 1–14;

$X_1$ and $X_3$ independently denote a single bond,

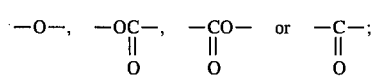

$X_2$ denotes a single bond,

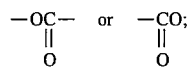

and $X_{4a}$, $X_{5a}$, $X_{4b}$, $X_{5b}$, $X_{4c}$ and $X_{5c}$ independently denote hydrogen, fluorine, chlorine, bromine, —$CH_3$, —CN or —$CF_3$; with proviso that $X_3$ cannot be —O— when $X_{4b}$ and $X_{5b}$ are both hydrogen in the formula (Ia), or when $X_{4a}$, $X_{5a}$, $X_{4b}$ and $X_{5b}$ are all hydrogen in the formula (If); and $X_1$ cannot be a single bond when $X_{4a}$ and $X_{5a}$ are both hydrogen in the formula (Ii).

3. A mesomorphic compound according to claim 1, which is represented by any one of the following formulas (Iaa)–(Ina):

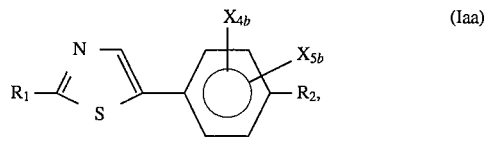

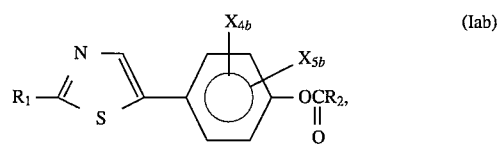

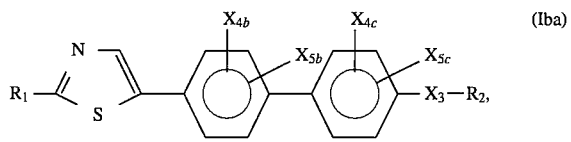

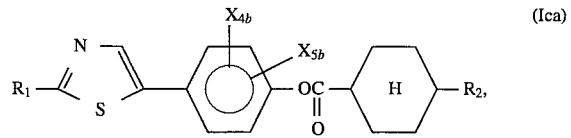

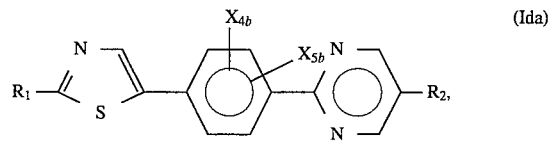

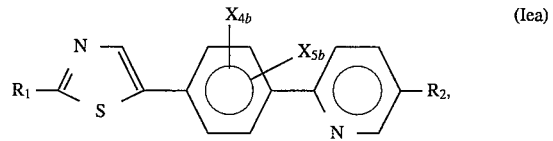

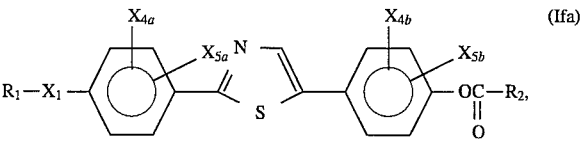

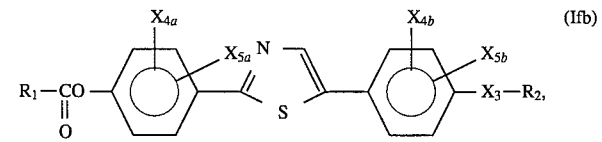

-continued $$X_{4a} \quad X_{5a} \quad N \quad X_{4b} \quad X_{5b}$$
$$R_1 - \text{Ar} = \text{CH-S-CH} = \text{Ar} - R_2 \quad \text{(Ifc)}$$

$$R_1O - \text{Ar} \cdots - R_2 \quad \text{(Ifd)}$$

$$R_1CO-O-\text{Ar}\cdots-R_2 \quad \text{(IIa)}$$

$$R_1O-\text{Ar}\cdots-R_2 \quad \text{(IIb)}$$

$$R_1-\text{thiazole-CH=CH-naphthyl-}X_3-R_2 \quad \text{(Ija)}$$

$$R_1-X_1-\text{naphthyl-thiazole-CH=CH-}R_2 \quad \text{(Ika)}$$

$$R_1-\text{Ar-thiazole-CH=CH-naphthyl-}X_3-R_2 \quad \text{(IIa)}$$

and $$R_1-\text{pyridyl-thiazole-CH=CH-Ar-}X_3-R_2 \quad \text{(Ina)}$$

wherein $R_1$ and $R_2$ independently denote any one of the following groups (i)–(iv):

(i) an n-alkyl group having 4–14 carbon atoms;

(ii)

$$\text{---}(CH_2)_{\overline{m}}\text{CH}\text{---}C_nH_{2n+1}$$
$$\quad\quad\quad\quad\quad | \\ \quad\quad\quad\quad CH_3$$

wherein m is an integer of 0–6 and n is an integer of 2–8;

(iii)

$$\text{---}(CH_2)_{\overline{r}}\text{CH}\text{---}(CH_2)_{\overline{s}}\text{OC}_tH_{2t+1}$$
$$\quad\quad\quad\quad\quad | \\ \quad\quad\quad\quad CH_3$$

wherein r is an integer of 0–6, s is 0 or 1 and t is an integer of 1–12; and (iv)

$$\text{---}(CH_2)_{\overline{m}}\text{CH}\text{---}C_xH_{2x+1}$$
$$\quad\quad\quad\quad\quad | \\ \quad\quad\quad\quad F$$

wherein m is 0 or 1 and x is an integer of 1–14;

$X_1$ and $X_3$ independently denote a single bond, $$-\underset{\underset{O}{\|}}{O}C-, \quad -\underset{\underset{O}{\|}}{C}O- \quad \text{or} \quad -\underset{\underset{O}{\|}}{C}-;$$

$X_{4a}$, $X_{5a}$, $X_{4b}$, $X_{5b}$, $X_{4c}$, and $X_{5c}$ independently denote hydrogen, fluorine, chlorine, bromine, $-CH_3$, $-CN$ or $-CF_3$.

4. A liquid crystal composition comprising at least two mesomorphic compounds, at least one of which is a mesomorphic compound of the formula (I) according to any one of claims 1–2.

5. A liquid crystal composition according to claim 4, which comprises 1–500 wt. parts of a mesomorphic compound of the formula (I) per 100 wt. parts of at least one species of another mesomorphic compound other than the mesomorphic compound of the formula (I).

6. A liquid crystal composition according to claim 4, which comprises 1–500 wt. parts of two or more species of mesomorphic compounds of the formula (I) per 100 wt. parts of at least one species of another mesomorphic compound other than the mesomorphic compound of the formula (I).

7. A liquid crystal composition according to claim 4, which assumes a chiral smectic phase.

8. A liquid crystal device, comprising a pair of electrode plates and a liquid crystal composition according to claim 4 disposed between the electrode plates.

9. A liquid crystal device according to claim 8, which further comprises an insulating alignment control layer.

10. A display apparatus comprising a liquid crystal device according to claim 8, and voltage application means for driving the liquid crystal device.

11. A display apparatus according to claim 10, wherein the liquid crystal device constitutes a display panel wherein the alignment direction of liquid crystal molecules is switched by utilizing ferroelectricity of the liquid crystal composition to effect display.

12. A display method comprising:

providing a liquid crystal composition according to claim 4 having ferroelectricity, and switching the alignment direction of liquid crystal molecules based on the ferroelectricity of the liquid crystal composition to effect display.

13. A display method, comprising:

providing a liquid crystal device according to claim 8, and switching the alignment direction of liquid crystal molecules to effect display based on the ferroelectricity of the liquid crystal composition contained in the liquid crystal device.

14. A liquid crystal composition according to claim 4, which comprises at least one species of another mesomorphic compound of the following formula (III):

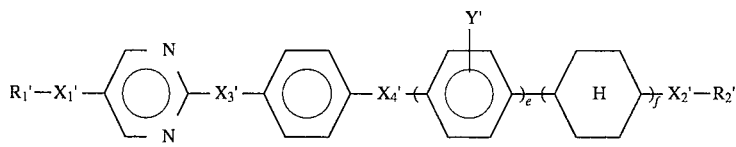 (III)

wherein $R'_1$ and $R'_2$ independently denote any one of the following groups (i) to (vii):

i) a linear alkyl group having 1–15 carbon atoms;

ii)

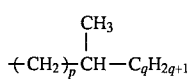

wherein p denotes an integer of 0–5 and q denotes an integer of 1–11;

iii)

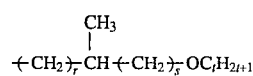

wherein r denotes an integer of 0–6, s denotes 0 or 1, and t denotes an integer of 1–14;

(iv)

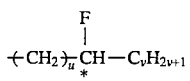

wherein u denotes 0 or 1 and v denotes an integer of 1–16;

v)

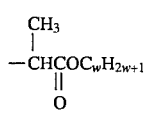

wherein w denotes an integer of 1–15;

vi)

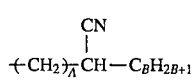

wherein A denotes an integer of 0–2 and B denotes an integer of 1–15; and vii)

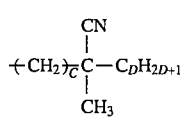

wherein C denotes an integer of 0–2 and D denotes an integer of 1–15;

e denotes 0 or 1 and f denotes 0 or 1 with proviso that e+f=0 or 1; Y' denotes H, halogen, $CH_3$ or $CF_3$; $X_1'$ and $X_2'$ respectively denote a single bond,

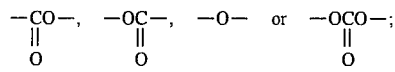

and $X_3'$ and $X_4'$ respectively denote a single bond,

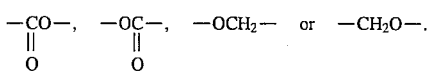

15. A liquid crystal composition according to claim 4, which comprises at least one species of another mesomorphic compound of the following formula (IV):

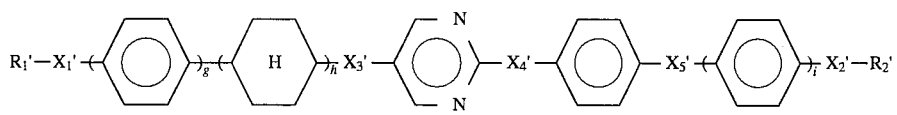 (IV)

wherein $R_1'$ and $R_2'$ independently denote any one of the following groups (i) to (vii):

i) a linear alkyl group having 1–15 carbon atoms;

ii)

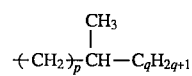

wherein p denotes an integer of 0–5 and q denotes an integer of 1–11;

iii)

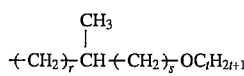

wherein r denotes an integer of 0–6, s denotes 0 or 1, and t denotes an integer of 1–14;

iv)

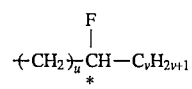

wherein u denotes 0 or 1 and v denotes an integer of 1–16;

v)

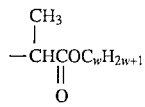

wherein w denotes an integer of 1–15;

vi)

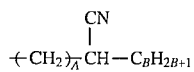

wherein A denotes an integer of 0–2 and B denotes an integer of 1–15; and vii)

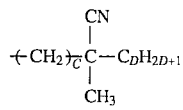

wherein C denotes an integer of 0–2 and D denotes an integer of 1–15;

g and h respectively denote 0 or 1 with proviso that g+h=1; i denotes 0 or 1; $X_1'$ and $X_2'$ respectively denote a single bond, $$-CO-,\quad -OC-,\quad -O-\quad or\quad -OCO-;$$
$$\phantom{-CO}\|\phantom{,\quad}\|\phantom{OC-,\quad -O-\quad or\quad}\|$$
$$\phantom{-CO-,}O\phantom{\quad}O\phantom{C-,\quad -O-\quad or\quad -OC}O$$

and $X_3'$, $X_4'$ and $X_5'$ respectively denote a single bond, $$-CO-,\quad -OC-,\quad -CH_2O-\quad or\quad -OCH_2-.$$

16. A liquid crystal composition according to claim 4, which comprises at least one species of another mesomorphic compound of the following formula (V):

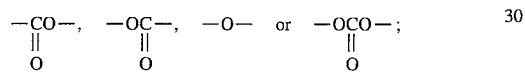 (V)

wherein $R'_1$ and $R'_2$ independently denote any one of the following groups (i) to (vii):

i) a linear alkyl group having 1–15 carbon atoms;

ii)

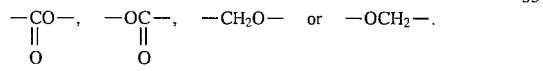

wherein p denotes an integer of 0–5 and q denotes an integer of 1–11;

iii)

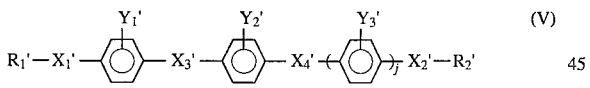

wherein r denotes an integer of 0–6, s denotes 0 or 1, and t denotes an integer of 1–14;

iv)

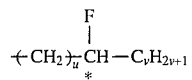

wherein u denotes 0 or 1 and v denotes an integer of 1–16;

v)

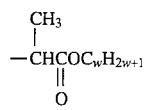

wherein w denotes an integer of 1–15;

vi)

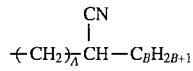

wherein A denotes an integer of 0–2 and B denotes and integer of 1–15; and vii)

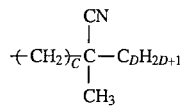

wherein C denotes an integer of 0–2 and D denotes and integer of 1–15;

j denotes 0 or 1; $Y_1'$, $Y_2'$ and $Y_3'$ respectively denote H, halogen, $CH_3$ or $CF_3$; $X_1'$ and $X_2'$ respectively denote a single bond,

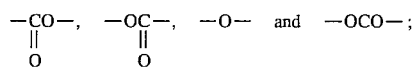

and $X_3'$ and $X_4'$ respectively denote a single bond,

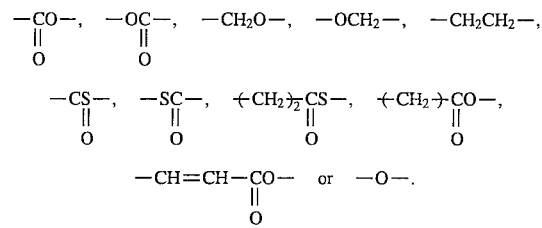

17. A liquid crystal composition according to claim 4, which comprises at least one species of another mesomorphic compound of the following formula (VI):

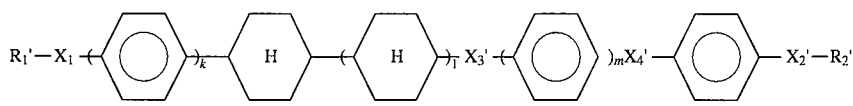

wherein $R'_1$ and $R'_2$ independently denote any one of the following groups (i) to (vii):

i) a linear alkyl group having 1–15 carbon atoms;

ii)

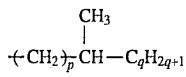

wherein p denotes an integer of 0–5 and q denotes and integer of 1–11;

iii)

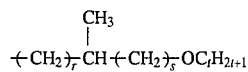

wherein r denotes an integer of 0–6, s denotes 0 or 1, and t denotes an integer of 1–14;

iv)

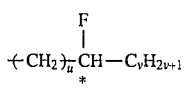

wherein u denotes 0 or 1 and v denotes an integer of 1–16;

v)

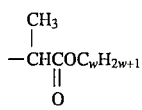

wherein w denotes an integer of 1–15;

vi)

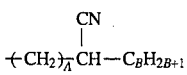

wherein A denotes an integer of 0–2 and B denotes an integer of 1–15; and vii)

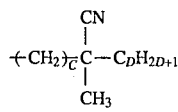

wherein C denotes an integer of 0–2 and D denotes an integer of 1–15;

k, l and m respectively denote 0 or 1 with proviso that k+l+m=0, 1 or 2; $X_1'$ and $X_2'$ respectively denote a single bond,

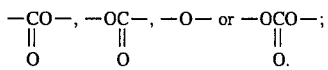

and $X_3'$ and $X_4'$ respectively denote a single bond,

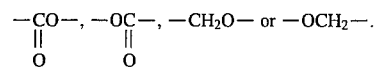

18. A liquid crystal composition according to claim 4, which comprises at least one species of another mesomorphic compound of the following formula (VII):

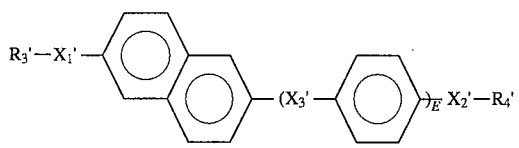

wherein $R'_3$ and $R_4'$ independently denote any one of the following groups (i) to (vii):

(i) a linear alkyl group having 1–15 carbon atoms;

(ii)

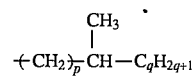

wherein p denotes an integer of 0–5 and q denotes an integer of 1–11;

(iii)

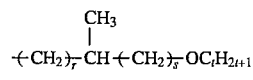

wherein r denotes an integer of 0–6, s denotes 0 or 1, and t denotes an integer of 1–14;

iv)

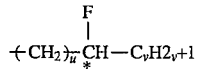

wherein u denotes 0 or 1 and v denotes an integer of 1–16;

v)

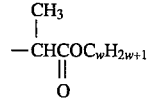

wherein w denotes an integer of 1–15;

vi)

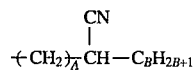

wherein A denotes an integer of 0–2 and B denotes an integer of 1–15; and vii)

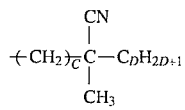

wherein C denotes an integer of 0–2 and D denotes an integer of 1–15;

wherein E denotes 0 or 1; $X_1'$ and $X_2'$ respectively denote a single bond,

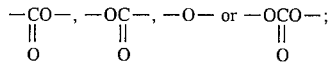

and $X_3'$ denotes a single bond,

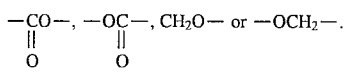

19. A liquid crystal composition according to claim 4, which comprises at least one species of another mesomorphic compound of the following formula (VIII):

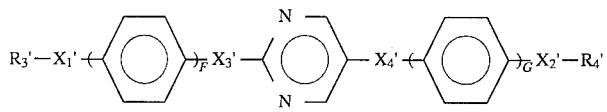

(VIII)

wherein $R'_3$ and $R'_4$ independently denote any one of the following groups (i) to (vii):

i) a linear alkyl group having 1–15 carbon atoms;
ii)

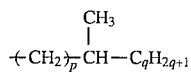

wherein p denotes an integer of 0–5 and q denotes an integer of 1–11;
iii)

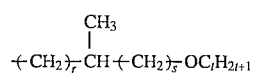

wherein r denotes an integer of 0–6, s denotes 0 or 1, and t denotes an integer of 1–14;
iv)

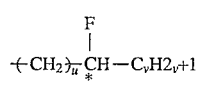

wherein u denotes 0 or 1 and v denotes an integer of 1–16;

v)

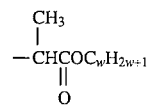

wherein w denotes an integer of 1–15;

vi)

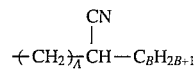

wherein A denotes an integer of 0–2 and B denotes an integer of 1–15; and vii)

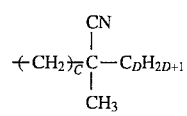

wherein C denotes an integer of 0–2 and D denotes and integer of 1–15;

F and G respectively denote 0 or 1; $X_1'$ and $X_2'$ respectively denote a single bond,

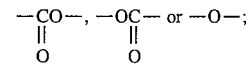

and $X_3'$ and $X_4'$ respectively denote a single bond,

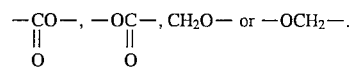

20. A liquid crystal composition according to claim 4, which comprises at least one species of another mesomorphic compound of the following formula (IX):

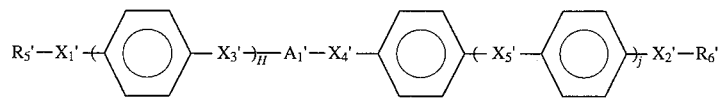

(IX)

wherein $R'_5$ and $R'_6$ independently denote any one of the following groups (i) to (vi):

i) a linear alkyl group having 1–15 carbon atoms;
ii)

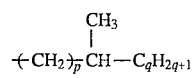

wherein p denotes an integer of 0–5 and q denotes and integer of 1–11;

iii)

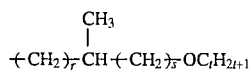

wherein r denotes an integer of 0–6, s denotes 0 to 1, and t denotes an integer of 1–14;

iv)

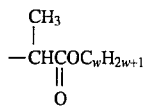

wherein w denotes an integer of 1–15;

v)

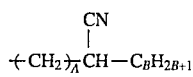

wherein A denotes an integer of 0–2 and B denotes and integer of 1–15; and vi)

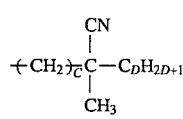

wherein C denotes an integer of 0–2 and D denotes an integer of 1–15;

H and J respectively denote 0 or 1 with proviso that H+J=0 or 1; $X_1'$ and $X_2'$ respectively denote a single bond, $$-\underset{\underset{O}{\|}}{C}O-, \quad -O\underset{\underset{O}{\|}}{C}-, \quad \text{or} \quad -O-;$$

$A_1'$ denotes

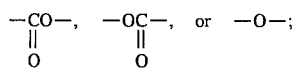

and $X_3'$ and $X_4'$ respectively denote a single bond, $$-\underset{\underset{O}{\|}}{C}O-, \quad -O\underset{\underset{O}{\|}}{C}-, \quad -CH_2O- \quad \text{or} \quad -OCH_2O-.$$

21. A liquid crystal composition according to claim 4, which comprises at least one species of another mesomorphic compound of the following formula (X):

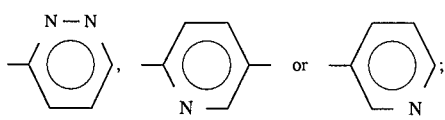 (X)

wherein $R'_5$ and $R'_6$ independently denote any one of the following groups (i) to (vi):

i) a linear alkyl group having 1–15 carbon atoms;

ii)

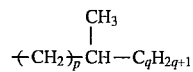

wherein p denotes an integer of 0–5 and q denotes and integer of 1–11;

iii)

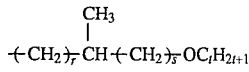

wherein r denotes an integer of 0–6, s denotes 0 or 1, and t denotes an integer of 1–14;

iv)

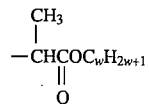

wherein w denotes an integer of 1–15;

v)

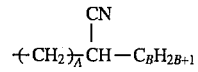

wherein A denotes an integer of 0–2 and B denotes an integer of 1–15; and (vi)

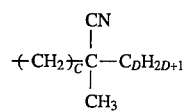

wherein C denotes an integer of 0–2 and D denotes an integer of 1–15;

$X_1'$ and $X_2'$ respectively denote a single bond, $$-\underset{\underset{O}{\|}}{C}O, \quad -O\underset{\underset{O}{\|}}{C}-, \quad \text{or} \quad -O-;$$

$A_1'$ denotes

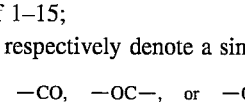

and $X_3'$ and $X_4'$ respectively denote a single bond, $$-\underset{\underset{O}{\|}}{C}O-, \quad -O\underset{\underset{O}{\|}}{C}-, \quad CH_2O- \quad \text{or} \quad -OCH_2-.$$

22. A liquid crystal composition according to claim 4, which comprises at least one species of another mesomorphic compound of the following formula (XI):

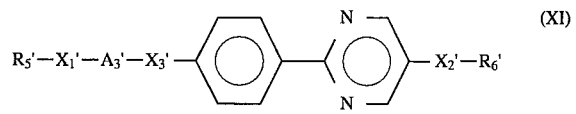 (XI)

wherein $R'_5$ and $R'_6$ independently denote any one of the following groups (i) to (vi):

i) a linear alkyl group having 1–15 carbon atoms;

ii)
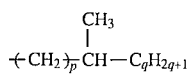

wherein p denotes an integer of 0–5 and q denotes an integer of 1–11;

iii)
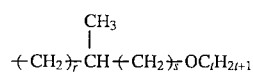

wherein r denotes an integer of 0–6, s denotes 0 or 1, and t denotes an integer of 1–14;

iv)
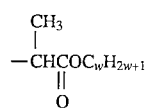

wherein w denotes an integer of 1–15;

v)
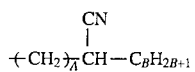

wherein A denotes an integer of 0–2 and B denotes an integer of 1–15; and vi)
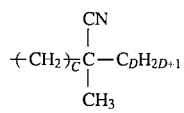

wherein C denotes an integer of 0–2 and D denotes an integer of 1–15;

$X_1'$ and $X_2'$ respectively denote a single bond,

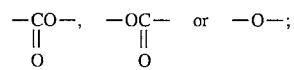

$A_3'$ denotes

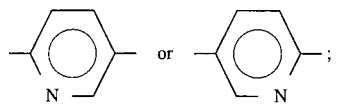

and $X_3'$ denotes a single bond,

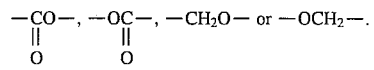

* * * * *

UNITED STATES PATENT AND TRADEMARK OFFICE
CERTIFICATE OF CORRECTION

PATENT NO. : 5,595,685

DATED : January 21, 1997

INVENTOR(S): TAKAO TAKIGUCHI ET AL.

It is certified that error appears in the above-identified patent and that said Letters Patent is hereby corrected as shown below:

Title page:
[56] REFERENCES CITED

Other Publications, "Zaschke et al., "Journal Prake. Chemie." vol. 321, pp. 643-654" should read --Zaschke et al., "Journal F. Prake. Chemie.", Vol. 321, No. 4, pp. 643-654--.
Other Publications, "J. Practical Chemistry, vol. 321, No. 4 (1979) 643-54." should be deleted.

[57] ABSTRACT

Line 50, "cyclohexyl," should read --cyclohexyl;--.

COLUMN 1

Line 7, "abandoned" should read --abandoned,--.

COLUMN 2

Line 5, "is" should read --are--.
Line 9, "has" should read --have--.
Line 32, "electric" should read --electric field--.

UNITED STATES PATENT AND TRADEMARK OFFICE
CERTIFICATE OF CORRECTION

PATENT NO. : 5,595,685

DATED : January 21, 1997

INVENTOR(S): TAKAO TAKIGUCHI ET AL.

It is certified that error appears in the above-identified patent and that said Letters Patent is hereby corrected as shown below:

COLUMN 4

Lines 20-22, " 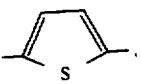 " should read

-- 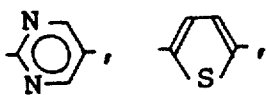 , --.

COLUMN 5

Lines 29-32, " 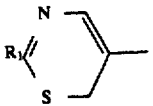 " should read

-- 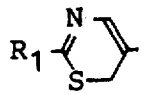 --.

COLUMN 7

Line 58, "and" (second occurrence) should read --are--.
Line 60, "In the above," should be a new paragraph.

COLUMN 11

Line 65, "J. Prake. Chem.", 321," should read
   --"Journal F. Prake. Chemie.", Vol. 321, No. 4,
   pp. 643-654--.

UNITED STATES PATENT AND TRADEMARK OFFICE
CERTIFICATE OF CORRECTION

PATENT NO. : 5,595,685

DATED : January 21, 1997

INVENTOR(S) : TAKAO TAKIGUCHI ET AL.

It is certified that error appears in the above-identified patent and that said Letters Patent is hereby corrected as shown below:

COLUMN 12

Line 19, "[Iia]" should read --[IIa]--.
Line 34, "disclose" should read --disclosure--.

COLUMN 13

Line 62, "$X_2$is" should read --$X_2$ is--.

COLUMN 14

Line 25, "Specific examples" should be a new paragraph.

COLUMN 24

Lines 7-9 "-COOC$_8$H$_{17}$" should read --COC$_8$H$_{17}$--
                               
           O                                        O

COLUMN 36

Line 22, "-X$_5$'-" should read --X$_5$-- --.
Line 28, "and" should read --or--.

COLUMN 41

Line 7, "-R$_2$'," should read -- -O-R$_2$',--.

UNITED STATES PATENT AND TRADEMARK OFFICE
CERTIFICATE OF CORRECTION

PATENT NO. : 5,595,685

DATED : January 21, 1997

INVENTOR(S): TAKAO TAKIGUCHI ET AL.

It is certified that error appears in the above-identified patent and that said Letters Patent is hereby corrected as shown below:

COLUMN 52

Line 55, "FIG." should read --FIGS.--.

COLUMN 53

Line 29, "44" should read --44,--.
Line 30, "(1911)" should read --(1911).--.

COLUMN 54

Line 12, "(4-methoxyphenyl)tiazole," should read
--(4-methoxyphenyl)thiazole,--.

COLUMN 55

Line 29, "(4-nonanoyloxyphenylthiazole" should
read --(4-nonanoyloxyphenyl)thiazole--.

COLUMN 57

Line 67, "(4-methoxyphenyl)tiazole," should read
--(4-methoxyphenyl)thiazole,--.

COLUMN 61

Line 3, "Iso" should read --Iso.--.

UNITED STATES PATENT AND TRADEMARK OFFICE
CERTIFICATE OF CORRECTION

PATENT NO. : 5,595,685

DATED : January 21, 1997

INVENTOR(S): TAKAO TAKIGUCHI ET AL.

It is certified that error appears in the above-identified patent and that said Letters Patent is hereby corrected as shown below:

COLUMN 64

Line 51, "second" should read --seconds--.

COLUMN 67

Line 3, "1-155" should read 1-55--.

COLUMN 73

Lines 48-50, "$C_6H_{13}O-$" with double bond to O should read --$C_6H_{13}C-$ with double bond to O--.

COLUMN 90

Line 55, "$S_{Th}^{55}A$" should read --SmA--.

COLUMN 92

Line 21, "hours" should read --hours at--.
Line 46, "Iso" should read --Iso.--.

COLUMN 97

Line 49, "cooling" should read --warming--.

UNITED STATES PATENT AND TRADEMARK OFFICE
CERTIFICATE OF CORRECTION

PATENT NO. : 5,595,685

DATED : January 21, 1997

INVENTOR(S) : TAKAO TAKIGUCHI ET AL.

It is certified that error appears in the above-identified patent and that said Letters Patent is hereby corrected as shown below:

COLUMN 98

Line 15, "$_2$M)" should read --$^2$M)--.
    Line 25, "ethanol," should read --ethanol
      were placed,--.

COLUMN 100

Line 56, "cooling" should read --warming--.
    Line 65, "hours." should read --hour.--.

COLUMN 101

Line 6, "ethanol," should read --ethanol
      were placed,--.

COLUMN 103

Line 33, "cooling" should read --warming--.
    Line 53, "ethanol," should read --ethanol
      were placed,--.

COLUMN 107

Line 10, "filtration" should read --filtration,--.

COLUMN 117

Line 25, "and," should read --and--.

UNITED STATES PATENT AND TRADEMARK OFFICE
CERTIFICATE OF CORRECTION

PATENT NO. : 5,595,685

DATED : January 21, 1997

INVENTOR(S) : TAKAO TAKIGUCHI ET AL.

It is certified that error appears in the above-identified patent and that said Letters Patent is hereby corrected as shown below:

COLUMN 119

Line 48, "$-R_2.$" should read -- $-R_2$ --.

COLUMN 120

Lines 12-16, " 

$X_{4a'}$ "

should read

-- 

and $X_{4a'}$ --

Line 22, "1-2." should read --1-3.--.

COLUMN 121

Line 8, "$R'_1$ and $R'_2$" should read --$R_1'$ and $R_2'$--.

COLUMN 123

Line 47, "$R'_1$ and $R'_2$" should read --$R_1'$ and $R_2'$--.

UNITED STATES PATENT AND TRADEMARK OFFICE
CERTIFICATE OF CORRECTION

PATENT NO. : 5,595,685

DATED : January 21, 1997

INVENTOR(S): TAKAO TAKIGUCHI ET AL.

It is certified that error appears in the above-identified patent and that said Letters Patent is hereby corrected as shown below:

COLUMN 124

Line 35, "and" (last occurrence) should read --an--.

COLUMN 125

Lines 1-3, "  " should read

-- 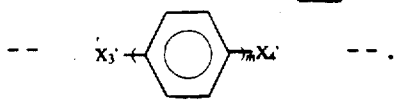 --.

Line 6, "R'$_1$ and R'$_2$" should read --R$_1$' and R$_2$'--.
Line 15, "and" (last occurrence) should read --an--.
Lines 63-66, "-OCO-;
O. "

should read

-- -OCO-;
O   --.

COLUMN 126

Line 22, "R'$_3$" should read --R$_3$'--.
Line 58, "v)" should be deleted.

UNITED STATES PATENT AND TRADEMARK OFFICE
CERTIFICATE OF CORRECTION

PATENT NO. : 5,595,685

DATED : January 21, 1997

INVENTOR(S): TAKAO TAKIGUCHI ET AL.

It is certified that error appears in the above-identified patent and that said Letters Patent is hereby corrected as shown below:

COLUMN 127

Line 10, "wherein" should be deleted.
Line 32, "$R'_3$ and $R'_4$" should read --$R_3'$ and $R_4'$--.

COLUMN 128

Line 32, "and" (last occurrence) should read --an--.
Line 55, "$R'_5$ and $R'_6$" should read --$R_5'$ and $R_6'$--.
Line 65, "and" (last occurrence) should read --an--.

COLUMN 129

Line 64, "$R'_5$ and $R'_6$" should read --$R_5'$ and $R_6'$--.

COLUMN 130

Line 7, "and" (last occurrence) should read --an--.
Line 47, "$A_1'$" should read --$A_2'$--.

UNITED STATES PATENT AND TRADEMARK OFFICE
CERTIFICATE OF CORRECTION

PATENT NO. : 5,595,685

DATED : January 21, 1997

INVENTOR(S) : TAKAO TAKIGUCHI ET AL.

It is certified that error appears in the above-identified patent and that said Letters Patent is hereby corrected as shown below:

<u>COLUMN 131</u>

Line 1, "$R'_5$ and $R'_6$" should read --$R_5'$ and $R_6'$--.

Signed and Sealed this

Tenth Day of February, 1998

Attest:

BRUCE LEHMAN

*Attesting Officer*     *Commissioner of Patents and Trademarks*